United States Patent
Chu et al.

(10) Patent No.: US 7,629,467 B2
(45) Date of Patent: Dec. 8, 2009

(54) DIPHENYL SUBSTITUTED CYCLOALKANES, COMPOSITIONS CONTAINING SUCH COMPOUNDS AND METHODS OF USE

(75) Inventors: Lin Chu, Scotch Plains, NJ (US); Mark T. Goulet, Westfield, NJ (US); Feroze Ujjainwalla, Scotch Plains, NJ (US); Linda Chang, Wayne, NJ (US); Richard Frenette, Laval (CA); Yves Girard, Ile-Bizard (CA); Michel Therien, Laval (CA); Dwight Macdonald, L'lle-Bizard (CA); John H. Hutchinson, LaJolla, CA (US)

(73) Assignees: Merck & Co., Inc., Rahway, NJ (US); Merck Frosst Canada Ltd, Quebec (CA)

( * ) Notice: Subject to any disclaimer, the term of this patent is extended or adjusted under 35 U.S.C. 154(b) by 287 days.

(21) Appl. No.: 10/565,604

(22) PCT Filed: Jul. 20, 2004

(86) PCT No.: PCT/US2004/023334

§ 371 (c)(1),
(2), (4) Date: Jan. 23, 2006

(87) PCT Pub. No.: WO2005/009951

PCT Pub. Date: Feb. 3, 2005

(65) Prior Publication Data

US 2006/0211677 A1      Sep. 21, 2006

Related U.S. Application Data

(60) Provisional application No. 60/489,693, filed on Jul. 24, 2003.

(51) Int. Cl.
| | | |
|---|---|---|
| *C07D 215/06* | (2006.01) | |
| *C07D 215/12* | (2006.01) | |
| *C07D 215/16* | (2006.01) | |
| *A61K 31/4375* | (2006.01) | |

(52) U.S. Cl. .................................. 546/152; 514/311

(58) Field of Classification Search .................. 546/152
See application file for complete search history.

(56) References Cited

U.S. PATENT DOCUMENTS

| | | | | |
|---|---|---|---|---|
| 5,107,041 | A | * | 4/1992 | Abe et al. ..................... 585/20 |
| 5,216,052 | A | | 6/1993 | Nesvadba |
| 5,691,351 | A | | 11/1997 | Kolasa |
| 6,087,513 | A | * | 7/2000 | Liao et al. ................... 549/524 |
| 6,753,429 | B2 | | 6/2004 | Theodoridis et al. |
| 6,756,400 | B2 | | 6/2004 | Chinn |

OTHER PUBLICATIONS

Vippagunta, et al. Advanced Drug Delivery Reviews 48 (2001) 3-26.*
Hepatitis [online] [retrieved on Apr. 22, 2009] and retrieved from URL; http://www.nlm.nih.gov/medlineplus/hepatitis.html.*
Viral Hepatitis [online] [retrieved on Apr. 22, 2009] and retrieved from URL; http://www.ucsfhealth.org/adult/medical_services/liver/viral/conditions/viralhep/treatments.html.*

* cited by examiner

*Primary Examiner*—Rebecca L Anderson
*Assistant Examiner*—Shawquia Young
(74) *Attorney, Agent, or Firm*—Mollie M. Yang; Valerie J. Camara

(57) ABSTRACT

The instant invention provides compounds of formula: (I) which are 5-lipoxygenase activating protein inhibitors: formula (I). Compounds of formula (I) are useful as anti-atherosclerotic, anti-asthmatic, anti-allergic, anti-inflammatory and cyto-protective agents.

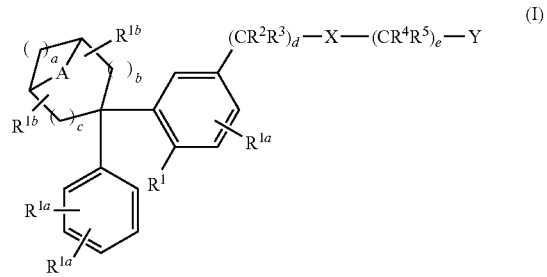

10 Claims, No Drawings

DIPHENYL SUBSTITUTED CYCLOALKANES, COMPOSITIONS CONTAINING SUCH COMPOUNDS AND METHODS OF USE

CROSS REFERENCE TO RELATED APPLICATIONS

This application is a 35 U.S.C. § 371 filing from International Application No. PCT/US2004/23334, filed Jul. 20, 2004, which claims the benefit under 35 U.S.C. 119(e) of U.S. Provisional Application No. 60/489,693, filed Jul. 24, 2003.

FIELD OF THE INVENTION

The instant invention involves compounds that inhibit 5-lipoxygenase activating protein (FLAP), compositions containing such compounds and methods of treatment using such compounds for the treatment and prevention of atherosclerosis and related diseases and conditions.

BACKGROUND OF THE INVENTION

Inhibition of leukotriene biosynthesis has been an active area of pharmaceutical research for many years. Leukotrienes are potent contractile and inflammatory mediators derived through the oxygenation of arachidonic acid by 5-lipoxygenase.

One class of leukotriene biosynthesis inhibitors are those known to act through inhibition of 5-lipoxygenase (5-LO). In general, 5-LO inhibitors have been sought for the treatment of allergic rhinitis, asthma and inflammatory conditions including arthritis. One example of a 5-LO inhibitor is the marketed drug zileuton, which is indicated for the treatment of asthma. More recently, it has been reported that 5-LO may be an important contributor to the atherogenic process; see Mehrabian, M. et al., Circulation Research, 2002 Jul. 26, 91(2):120-126.

A new class of leukotriene biosynthesis inhibitors (now known as FLAP inhibitors) distinct from 5-LO inhibitors is described in Miller, D. K. et al., Nature, vol. 343, No. 6255, pp. 278-281, 18 Jan. 1990. These compounds inhibit the formation of cellular leukotrienes but have no direct effect on soluble 5-LO activity. These compounds were used to identify and isolate the inner nuclear membrane 18,000 dalton protein 5-lipoxygenase-activating protein (FLAP). In cells, arachidonic acid is released from membrane phospholipids by the action of cytosolic phospholipase 2. This arachidonic acid is transferred to nuclear membrane bound 5-lipoxygenase by FLAP. The presence of FLAP in cells is essential for the synthesis of leukotrienes. Additionally, based on studies described in Helgadottir, A., et al., Nature Genetics, vol 36, no. 3 (March 2004) 233-239, it is believed that the gene encoding 5-lipoxygenase activating protein confers risk for myocardial infarction and stroke in humans.

Despite significant therapeutic advances in the treatment and prevention of atherosclerosis and ensuing atherosclerotic disease events, such as the improvements that have been achieved with HMG-CoA reductase inhibitors, further treatment options are clearly needed. The instant invention addresses that need by providing compounds, compositions and methods for the treatment or prevention of atherosclerosis as well as related conditions.

SUMMARY OF THE INVENTION

The instant invention relates to compounds of formula I which are FLAP inhibitors, methods for their preparation, and methods and pharmaceutical formulations for using these compounds in mammals, especially humans. This invention provides compounds of structural formula I:

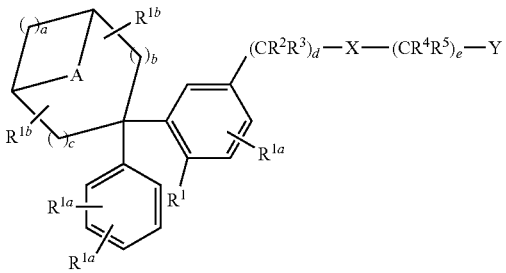

and the pharmaceutically acceptable salts, esters and solvates thereof. This invention also involves the use of compounds described herein to slow or halt atherogenesis. Therefore, one object of the instant invention is to provide a method for treating atherosclerosis, which includes halting or slowing the progression of atherosclerotic disease once it has become clinically evident, comprising administering a therapeutically effective amount of a compound of formula I to a patient in need of such treatment. Another object is to provide methods for preventing or reducing the risk of developing atherosclerosis and atherosclerotic disease events, comprising administering a prophylactically effective amount of a compound of Formula I to a patient who is at risk of developing atherosclerosis or having an atherosclerotic disease event.

The compounds of Formula I are also useful as anti-asthmatic, anti-allergic, anti-inflammatory and cytoprotective agents. They are also useful in treating angina, cerebral spasm, glomerular nephritis, hepatitis, endotoxemia, uveitis, and allograft rejection. The instant invention provides methods of treatment comprising administering a therapeutically effective amount of a compound of Formula I to a patient in need of the above-described treatments.

A further object is to provide the use of FLAP inhibitors of formula I in combination with other therapeutically effective agents, including other anti-atherosclerotic drugs. These and other objects will be evident from the description contained herein.

DETAILED DESCRIPTION OF THE INVENTION

The instant invention provides a compound represented by structural formula I

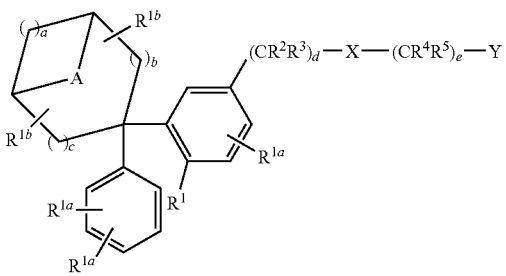

and the pharmaceutically acceptable salts, esters and solvates thereof wherein:

"a" is an integer selected from 1, 2 and 3; and b and c are each integers independently selected from 0, 1 and 2;

"A" represents a methylene or ethylene group;

each $R^{1a}$ is independently selected from the group consisting of: —H, —F, —Cl, —Br, —$C_{1-6}$alkyl, —CN, —OH, —$OC_{1-16}$ alkyl, -fluoro$C_{1-6}$ allyl, -fluoro$C_{1-6}$ alkoxy, —N($R^a$)$_2$, —$C_{1-6}$alkylN($R^a$)$_2$, —NHC(O)$C_{1-4}$alkyl, —C(O)NH$C_{1-4}$alkyl and —C(O)N($C_{1-4}$alkyl)$_2$;

each $R^{1b}$ is independently selected from the group consisting of: —H, —F, —$C_{1-6}$ alkyl, —OH, —$OC_{1-6}$ alkyl, -fluoro$C_{1-6}$alkyl, -fluoro$C_{1-6}$alkoxy, —N($R^a$)$_2$ and —$C_{1-6}$alkylN($R^a$), or one $R^{1b}$ group can represent oxo and the other is as previously defined;

$R^1$ represents —H or is selected from the group consisting of:

a) halo, —OH, —$CO_2R^a$, —C(O)$NR^aR^b$, —C(O)-Hetcy$^1$, —N($R^a$)$_2$, —S(O)$_2NR^aR^b$, —$NO_2$, —$SO_2NR^bC(O)R^a$, —$NR^bSO_2R^a$, —$NR^bC(O)R^a$, —C(O)$SO_2NR^aR^b$, —$NR^bC(O)NR^aR^b$, —$NR^bCO_2R^a$, —OC(O)$NR^aR^b$, —C(O)$NR^bN$-$R^aR^b$, —CN, —S(O)$_pR^a$ and —$OSO_2R^a$, b) —$C_{1-10}$alkyl, —$C_{2-10}$alkenyl, —$C_{2-10}$alkynyl, —O$C_{1-10}$allyl, —$OC_{3-10}$alkenyl and —$OC_{3-10}$alkynyl, said groups being optionally substituted with: —OH, —$CO_2R^a$, —C(O)$NR^aR^b$, —C(O)N($R^a$)$C_{1-6}$alkenyl, —C(O)N($R^a$)$C_{1-6}$alkynyl, —C(O)-Hetcy$^1$, —N($R^a$)$_2$, —S(O)$_2NR^aR^b$, —$SO_2NR^bC(O)R^a$, —$NR^bSO_2R^a$, —$NR^bC(O)R^a$, —C(O)$SO_2NR^aR^b$, $NR^bC(O)NR^aR^b$, —$NR^bCO_2R^a$, —OC(O)$NR^aR^b$, —C(O)$NR^bNR^aR^b$, —S(O)$_pR^a$, Aryl, HAR, -Hetcy$^1$, and up to 5 fluoro groups, wherein Hetcy$^1$ is selected from azetidinyl, pyrrolidinyl, piperidinyl, piperazinyl, morpholinyl and γ-lactam;

c) Aryl or HAR optionally substituted with 1-2 members selected from the group consisting of: —F, —Cl, —Br, —$C_{1-6}$alkyl, —CN, —OH, —$OC_{1-6}$alkyl, -fluoro$C_{1-6}$alkyl, -fluoro$C_{1-6}$alkoxy, —$NH_2$, —NH$C_{1-4}$alkyl, —N($C_{1-4}$alkyl)$_2$, —$C_{1-6}$aklkylNH$_2$, —$C_{1-6}$alkyl-NH$C_{1-4}$alkyl, —$C_{1-6}$alkylN($C_{1-4}$alkyl)$_2$, —$C_{1-6}$alkyl-CN, —NHC(O)$C_{1-4}$alkyl, —C(O)NH$C_{1-4}$alkyl and —C(O)N($C_{1-4}$alkyl)$_2$;

"d" and "e" are each integers independently selected from 0, 1, 2 and 3, such that the sum of d plus e is 1-6;

each p independently represents an integer selected from 0, 1 and 2;

X represents a bond, or is selected from the group consisting of —O—, —S(O)$_p$— and —$NR^a$—;

$R^2$, $R^3$, $R^4$ and $R^5$ are each independently selected from the group consisting of —H, —$C_{1-6}$ alkyl, —$OC_{1-6}$alkyl, —OH, -fluoro, -fluoro$C_{1-6}$alkyl, -fluoro$C_{1-6}$alkoxy, —N($R^a$)$_2$, and 0-1 of $CR^2R^3$ and 0-1 of $CR^4R^5$ can represent a group selected from carbonyl, thiocarbonyl, C=$NR^a$ and a 3-7 membered cycloalkyl ring, provided that when X represents —S(O)$_p$—, and p is 1 or 2, the $CR^2R^3$ and $CR^4R^5$ groups adjacent to X represent moieties other than carbonyl, thiocarbonyl and C=$NR^a$ and further provided that when X is —O— or —$NR^a$—, at least one of $CR^2R^3$ and $CR^4R^5$ adjacent to X represents a moiety other than carbonyl, thiocarbonyl and C=$NR^a$;

Y is selected from the group consisting of Aryl, HAR and Hetcy, wherein each is optionally mono-substituted or di-substituted with $R^{1a}$;

each $R^a$ is independently selected from the group consisting of —H and:

(a) —$C_{10}$alkyl, —$C_{3-10}$alkenyl, or —$C_{3-10}$alkynyl, optionally substituted with 1-3 fluoro groups or 1-2 members selected from the group consisting of: —OH, —$OC_{1-6}$alkyl, —CN, —$NH_2$, —NH$C_{1-4}$alkyl, and —N($C_{1-4}$alkyl)$_2$;

(b) Aryl or Ar—$C_{1-6}$alkyl-, the aryl portions being optionally substituted with 1-2 of —$C_{1-6}$ alkyl, —CN, —OH, —$OC_{1-6}$ alkyl, -fluoro$C_{1-6}$ alkyl, -fluoro$C_{1-6}$ alkoxy, —$C_{1-6}$alkylNH$_2$, —$C_{1-6}$alkylNH$C_{1-4}$alkyl, —$C_{1-6}$alkylN($C_{1-4}$alkyl)$_2$, —$NH_2$, —NH$C_{1-4}$alkyl, —N($C_{1-4}$alkyl)$_2$, —NHC(O)$C_{1-4}$alkyl, —C(O)NH$C_{1-4}$alkyl, —C(O)N($C_{1-4}$alkyl)$_2$, —$CO_2$H and —$CO_2C_{1-6}$alkyl groups, and 1-3-F, —Cl or —Br groups;

and the alkyl portion of Ar—$C_{1-6}$alkyl- being optionally substituted with —OH, —$OC_{1-6}$alkyl, —$NH_2$, —NH$C_{1-4}$alkyl, —N($C_{1-4}$alkyl)$_2$, and 1-3 fluoro groups;

(c) Hetcy or Hetcy-$C_{1-6}$alkyl-, each being optionally substituted on carbon with 1-2 members selected from the group consisting of: —F, —OH, —$CO_2$H, —$C_{1-6}$alkyl, —$CO_2C_{1-6}$alkyl, —$OC_{1-6}$alkyl, —$NH_2$, —NH$C_{1-4}$alkyl, —N($C_{1-4}$alkyl)$_2$, —NHC(O)$C_{1-4}$alkyl, oxo, —C(O)NH$C_{1-4}$alkyl and —C(O)N($C_{1-4}$alkyl)$_2$; and optionally substituted on nitrogen when present with —$C_{1-6}$alkyl or —$C_{1-6}$acyl; and the alkyl portion of Hetcy-$C_{1-6}$alkyl- being optionally substituted with 1-2 of: —F, —OH, —$OC_{1-6}$alkyl, —$NH_2$, —NH$C_{1-4}$alkyl and —N($C_{1-4}$alkyl)$_2$;

(d) HAR or HAR-$C_{1-6}$alkyl-, said HAR and HAR portion of HAR-$C_{1-6}$alkyl- being substituted with 1-2 members selected from the group consisting of: —F, —Cl, —Br, —$C_{1-6}$ alkyl, —CN, —OH, —$OC_{1-6}$ alkyl, -fluoro$C_{1-6}$alkyl, -fluoro$C_{1-6}$alkoxy $NH_2$, —NH$C_{1-4}$alkyl, —N($C_{1-4}$alkyl)$_2$, —NHC(O)$C_{1-4}$alkyl, —C(O)NH$C_{1-4}$alkyl, —C(O)N($C_{1-4}$alkyl)$_2$, —$CO_2$H, —$CO_2C_{1-6}$alkyl; and the alkyl portion of HAR-$C_{1-6}$alkyl- being optionally substituted with 1-2 of: —F, —OH, —$OC_{1-6}$alkyl, —$NH_2$, —NH$C_{1-4}$alkyl and —N($C_{1-4}$alkyl)$_2$;

each $R^b$ is independently selected from the group consisting of: —H, —$NH_2$, and —$C_{1-10}$alkyl optionally substituted with members selected from the group consisting of 1-3 fluoro groups and 1-2 of —OH, —$OC_{1-6}$alkyl, —$NH_2$, —NH$C_{1-4}$alkyl and —N($C_{1-4}$alkyl)$_2$;

and when present in the same moiety, (a) $R^a$ and $R^b$, (b) two $R^a$ groups or (c) two $R^b$ groups can be taken in combination with the atom or atoms to which they are attached and any intervening atoms and represent a 4-7 membered ring containing 0-3 heteroatoms selected from O, S(O)$_p$ and N, and the 4-7 membered ring may be optionally substituted with a member selected from the group consisting of —$C_{1-6}$alkyl, —$C_{2-6}$acyl and oxo.

The invention is described herein in detail using the terms defined below unless otherwise specified. "Alkyl", as well as other groups having the prefix "alk", such as alkoxy, alkanoyl and the like, means carbon chains which may be linear, branched or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl and is intended to be included within the meaning of "alkyl"; if no number of atoms is specified, 3-10 carbon atoms are intended, forming 1-3 carbocyclic rings that are fused; 3-6 carbons in a monocyclic alkyl ring is preferred. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Alkenyl" means carbon chains which contain at least one carbon-carbon double bond, and which may be linear or branched or combinations thereof, and includes chains having 3-10 carbons, and more particularly 3-6 carbons. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof, and includes chains having 3-10 carbons, and more particularly 3-6 carbons. Examples of alkynyl include ethynyl, propargyl, 3-methyl-1-pentynyl, 2-heptynyl and the like.

"Aryl" (Ar) means mono- and bicyclic aromatic rings containing 6-12 carbon atoms. Examples of aryl include phenyl, naphthyl, indenyl and the like.

"Acyl" refers to an alkyl group as defined above linked through a carbonyl group. A preferred example is acetyl, $CH_3C(O)-$.

"Heteroaryl" (HAR) means a mono- or fused aromatic or partially unsaturated ring or ring system containing up to two rings, with each ring containing 5 to 6 atoms, and containing at least one heteroatom selected from O, S and N. Examples include the following:

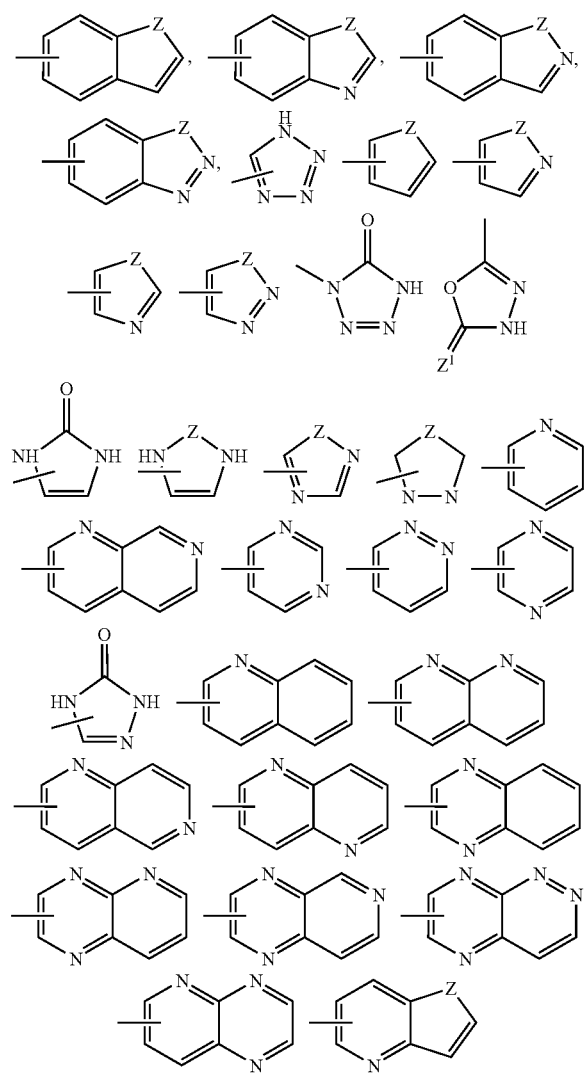

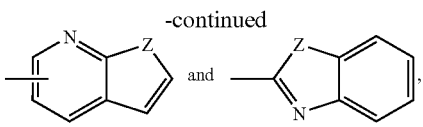

wherein Z represents O, S or NH; and $Z^1$ represents O or S.

Heteroaryl also includes aromatic heterocyclic groups fused to heterocycles that are non-aromatic or partially aromatic, and aromatic heterocyclic groups fused to cycloalkyl rings. The term also includes partially unsaturated monocyclic rings that are not aromatic, such as 2- or 4-pyridones attached through the nitrogen or N-substituted-(1H,3H)-pyrimidine-2,4-diones (N-substituted uracils). Heteroaryl also includes such groups in charged form, e.g., pyridinium. Substituents, when present, may be on any available carbon in the ring; suitable substituents may also be on available nitrogens in the ring.

"Heterocyclyl" (Hetcy) means mono- and bicyclic saturated rings and ring systems containing at least one heteroatom selected from N, S and O, each of said ring having from 3 to 10 atoms in which the point of attachment may be carbon or nitrogen. Examples of "heterocyclyl" include azetidinyl, pyrrolidinyl, piperidinyl, piperazinyl, morpholinyl, γ-lactam, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils). Heterocyclyl moreover includes such moieties in charged form, e.g., piperidinium. Substituents, when present, may be on any available carbon in the ring; suitable substituents may also be on available nitrogens in the ring. "Hetcy$^1$" is a subset of Hetcy and is defined in formula I above. Within the moiety $-C(O)$-Hetcy$^1$, Hetcy$^1$ is N-linked to $-C(O)-$, for example:

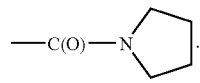

All other occurrences of Hetcy$^1$ in formula I can be linked to the structure via carbon or nitrogen in the Hetcy$^1$ ring.

"Halogen" (Halo) includes fluorine, chlorine, bromine and iodine, preferably F and Cl, more preferably F. Halo $C_{1-6}$alkyl, halo$C_{1-6}$alkoxy and the like mean alkyl, alkoxy and the like substituted with at least one halo group up to perhalo. Fluoroalkyl and fluoroalkoxy mean alkyl and alkoxy groups that are substituted with 1-6 fluoro groups. Perferably 1-4 halo or fluoro groups are present on the alkyl or alkoxy moiety. The preferred haloalkyl is $-CF_3$. The preferred haloalkoxy is $-OCF_3$.

Reference to the compounds of this invention as those of "formula I," "formula Ia," "formula Ib" and "formula Ic" is intended herein to encompass compounds falling within the scope of each of these structural formulas including pharmaceutically acceptable salts and esters thereof where such salts and esters are possible. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like, and particularly citric, fumaric, hydrobromic, hydrochloric, maleic, phosphoric, sulfuric, and tartaric acids.

Pharmaceutically acceptable esters of available hydroxy or carboxylic acid groups can optionally be formed as well. Examples of pharmaceutically acceptable esters include, but are not limited to, —$C_{1-4}$ alkyl and —$C_{1-4}$ alkyl substituted with phenyl-, dimethylamino- and acetylamino.

The compounds of formula I may contain one or more asymmetric centers, and can thus occur as racemates, racemic mixtures, single enantiomers, diastereoisomeric mixtures and individual diastereoisomers. The present invention includes all such isomers, as well as salts and solvates of such racemates, mixtures, enantiomers and diastereoisomers. Furthermore, some of the crystalline forms of compounds of the present invention may exist as polymorphs and as such are intended to be included in the present invention. In addition, some of the compounds of the instant invention may form solvates with water or common organic solvents. Such solvates and hydrates are likewise encompassed within the scope of this invention. Some of the compounds described herein contain olefinic double bonds. The invention includes both E and Z geometric isomers. Some of the compounds decribed herein may exist as tautomers, e.g., keto-enol tautomers. Individual tautomers as well as mixtures thereof are included in the present invention.

Compounds of structural formula I may be separated into their individual diastereoisomers by, e.g., fractional crystallization from suitable solvents, e.g., methylene chloride/hexanes or EtOAc/hexanes, or via chiral chromatography using an optically active stationary phase. Absolute stereochemistry may be determined by X-ray crystallography of crytalline products or crystalline intermediates which are derivatized, if necessary, with a reagent containing a stereogenic center of known configuration. Alternatively, any stereoisomer of a compound of the general formula I may be obtained by stereospecific synthesis using optically pure starting materials or reagents of known absolute configuration.

One aspect of the invention relates to compounds within the scope of formula I having structural formula Ia:

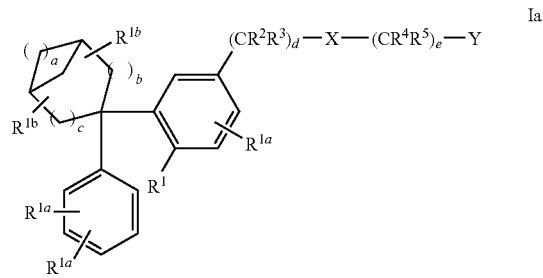

and the pharmaceutically acceptable salts, esters and solvates thereof, wherein "a" is an integer selected from 1, 2 and 3; and b and c are each integers independently selected from 0, 1 and 2; provided that the sum of "a"+b+c is from 1 to 5, so that a 5-9 membered bicyclic ring system is provided. Within this aspect of the invention, "A" as shown in formula I represents a methylene group, and all other variables are as originally defined in formula I. More particularly, a further aspect of the invention relates to a compound of formula Ia wherein "a" is 1 or 2, one of b and c is 0 (zero) and the other is 1, such that a 6-7 membered bicyclic ring system is provided. "A", as shown in formula I, represents a methylene group, and all other variables are as originally defined in formula I.

Yet another aspect of the invention relates to compounds within the scope of formula I having formula Ib:

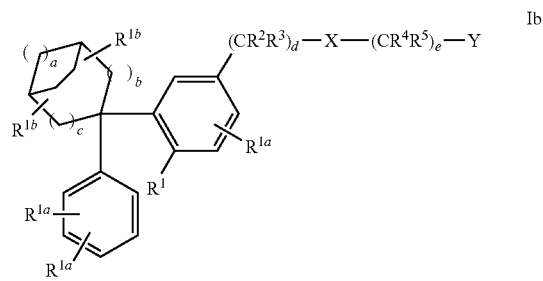

and the pharmaceutically acceptable salts, esters and solvates thereof wherein: "a" is an integer selected from 2 and 3; and b and c are integers independently selected from 0 and 1; provided that the sum of "a"+b+c is from 2 to 4, so that a 7-9 membered bicyclic ring system is provided. Within this aspect of the invention, "A", as shown in formula I, represents an ethylene group, and all other variables are as originally defined in formula I.

More particularly, a further aspect of the invention relates to a compound of formula Ib wherein "a" is 2, and b and c are integers independently selected from 0 and 1, such that a 7-9 membered ring is provided. Again, as shown in formula I, "A" represents an ethylene group, and all other variables are as originally defined in formula I.

Even more particularly, another aspect of the invention relates to compounds of formula Ib wherein "a" represents 2, b represents 1 and c represents 0 or 1. Within this aspect of the invention, as shown in formula I, "A" represents an ethylene group, and all other variables are as originally defined in formula I.

Another aspect of the invention relates to compounds within the scope of formula I having structural formula Ic:

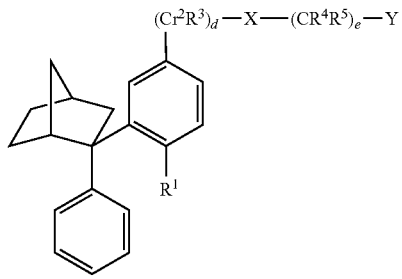

wherein d is 0 (zero); e is 1; X is —O—; $R^4$ and $R^5$ are both —H; Y is selected from the group consisting of

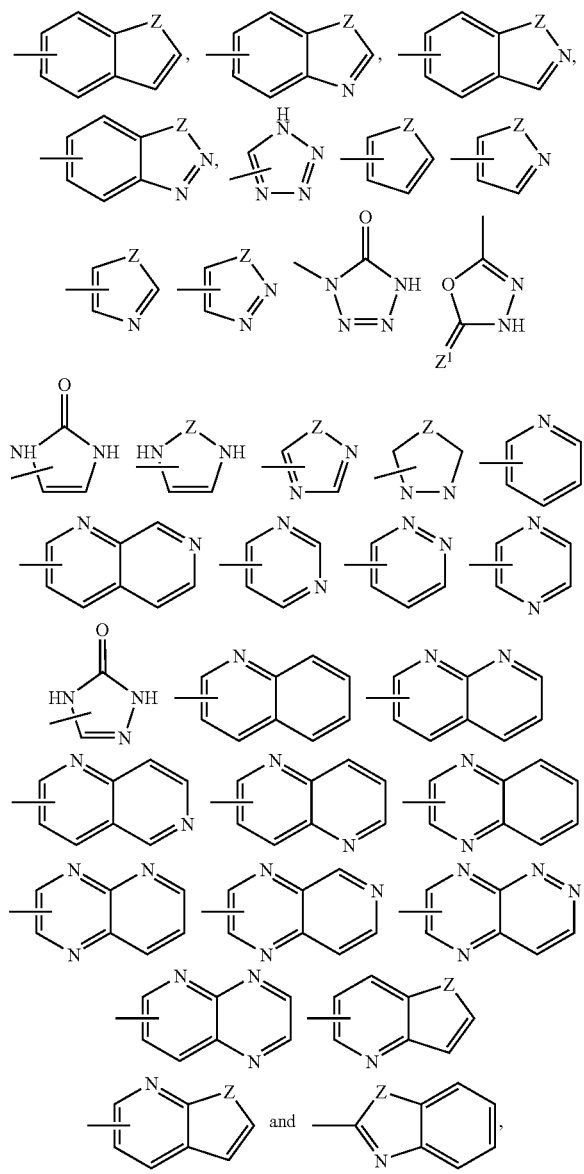

wherein Z represents O, S or NH; and $Z^1$ represents O or S;

and more particularly Y is selected from:

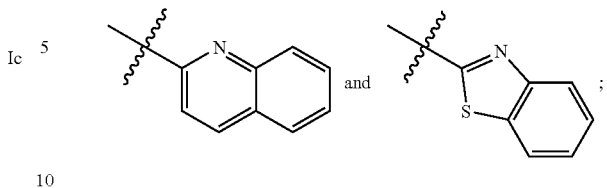

and $R^1$ is selected from the group consisting of:
a) —OC(O)$NR^aR^b$, and —C(O)$NR^aR^b$;
b) $C_{1-3}$alkyl substituted with a member selected from: —C(O)—$NR^aR^b$ and —C(O)-$Hetcy^1$;
and c) HAR optionally substituted with 1-2 members selected from the group consisting of: —F, —Cl, —$C_{1-6}$alkyl, —CN, —OH, —$OC_{1-6}$ alkyl, -fluoro$C_{1-6}$ alkyl, -fluoro $C_{1-6}$alkoxy, —$NH_2$, —$NHC_{1-4}$alkyl, —$N(C_{1-4}$alkyl$)_2$, —$C_{1-6}$alkyl$NH_2$, —$C_{1-6}$alkyl-$NHC_{1-4}$alkyl, —$C_{1-6}$alkylN$(C_{1-4}$alkyl$)_2$, —$C_{1-6}$alkyl-CN, —NHC(O)$C_{1-4}$alkyl, —C(O)NH$C_{1-4}$alkyl and —C(O)N($C_{1-4}$allyl$)_2$;

and more particularly, when $R^1$ is HAR, HAR is selected from:

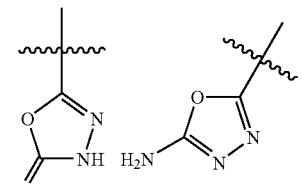

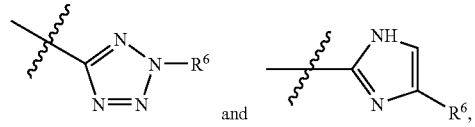

wherein $R^6$ is selected from —H, —$C_{1-3}$alkyl, —$C_{3-6}$cycloalkyl, —F and —Cl; and wherein all remaining variables are as originally defined in formula I.

In a sub-set of this aspect of formula Ic, $R^a$ is selected from:
(a) —$C_{1-4}$-alkyl and $C_{3-6}$cycloalkyl, each optionally substituted with 1-3 fluoro groups or a member selected from the group consisting of: —$OC_{1-6}$alkyl, —CN, —$NH_2$, —NH $C_{1-4}$alkyl and —N($C_{1-4}$alkyl$)_2$,
(b) $Hetcy^1$ and
(c) pyridinyl;

$R^b$ is —H; and wherein all remaining variables are as defined in formula Ic.

Another aspect of the invention relates to compounds of formula I wherein of the three $R^{1a}$ groups shown in the generic structural drawing of formula I, two $R^{1a}$ groups represent —H and one $R^{1a}$ group is selected from the group consisting of: —F, —Cl, —$C_{1-6}$ alkyl, —CN, —$OC_{1-6}$ alkyl, -fluoro$C_{1-6}$ alkyl, -fluoro$C_{1-6}$alkoxy, —$N(R^a)_2$, —$C_{1-6}$alkylN$(R^a)_2$, —NHC(O)$C_{1-4}$alkyl, —C(O)NH $C_{1-4}$alkyl and —C(O)N($C_{1-4}$alkyl$)_2$. Within this aspect of the invention, all other variables are as originally defined in formula I. A further aspect of the invention relates to compounds of formula I wherein all three $R^{1a}$ groups shown in the generic structural drawing of formula I are —H. Within this aspect of the invention, all other variables are as originally defined in formula I.

In another aspect of the invention, a compound of formula I is disclosed wherein one $R^{1b}$ represents —H and the other $R^{1b}$ is selected from the group consisting of: —H, —F, —$C_{1-6}$alkyl, —OH, —$OC_{1-6}$ alkyl, -fluoro$C_{1-6}$alkyl, -fluoro$C_{1-6}$alkoxy, —$N(R^a)_2$ and —$C_{1-6}$alkyl$N(R^a)_2$ and oxo. Within this aspect of the invention, all other variables are as originally defined in formula I. More particularly, a further aspect of the invention relates to a compound of formula I wherein both $R^{1b}$ groups represent —H. Within this aspect of the invention, all other variables are as originally defined in formula I.

In another aspect of the invention, a compound of formula I is disclosed wherein $R^1$ represents a member selected from the group consisting of:

a) —$C(O)NR^aR^b$, —C(O)-Hetcy$^1$, —$N(R^a)_2$, —$S(O)_2NR^aR^b$, —$SO_2NR^bC(O)R^a$, —$NR^bSO_2R^a$, —$NR^bC(O)R^a$, —CN, —$S(O)_pR^a$ and —$OSO_2R^a$;

b) —$C_{1-10}$alkyl, —$C_{3-6}$alkenyl, —$C_{3-6}$aklynyl, —O$C_{1-10}$alkenyl, —$OC_{3-6}$alkenyl and —$OC_{3-10}$alkynyl, said groups being optionally substituted with a member selected form the group consisting of: —$CO_2R^a$, —$C(O)NR^aR^b$, —$C(O)N(R^a)C_{1-6}$alkenyl, —$C(O)N(R^a)C_{1-6}$aklynyl, —C(O)-Hetcy$^1$, —$N(R^a)_2$, —$S(O)_2NR^aR^b$, —$SO_2NR^bC(O)R^a$, —$NR^bSO_2R^a$, $NR^bC(O)R^a$, —$S(O)_pR^a$, Aryl, HAR, -Hetcy$^1$, and up to 5 fluoro groups; and c) HAR optionally substituted with 1-2 members selected from the group consisting of: —F, —Cl, —Br, —$C_{1-6}$ alkyl, —CN, —OH, —$OC_{1-6}$ alkyl, -fluoro$C_{1-6}$ alkyl, -fluoro$C_{1-6}$alkoxy, —$NH_2$, —$NHC_{1-4}$alkyl, —$N(C_{1-4}$alkyl$)_2$, —$C_{1-6}$alkyl$NH_2$, —$C_{1-6}$alkyl-$NHC_{1-4}$alkyl, —$C_{1-6}$alkylN$(C_{1-4}$alkyl$)_2$, —$C_{1-6}$alkyl-CN, —$NHC(O)C_{1-4}$alkyl, —$C(O)NHC_{1-4}$alkyl and —$C(O)N(C_{1-4}$alkyl$)_2$. Within this aspect of the invention, all other variables are as originally defined in formula I. A further aspect of the invention relates to compounds of formula I wherein $R^1$ represents a member selected from the group consisting of:

a) —$OC(O)NR^aR^b$, and —$C(O)NR^aR^b$;

b) $C_{1-3}$alkyl substituted with a member selected from: —C(O)—$NR^aR^b$ and —C(O)-Hetcy$^1$;

and c) HAR optionally substituted with 1-2 members selected from the group consisting of: —F, —Cl, —$C_{1-6}$ alkyl, —CN, —OH, —$OC_{1-6}$ alkyl, -fluoro$C_{1-6}$ alkyl, -fluoro$C_{1-6}$alkoxy, —$NH_2$, —$NHC_{1-4}$alkyl, —$N(C_{1-4}$alkyl$)_2$, —$C_{1-6}$alkyl$NH_2$, —$C_{1-6}$alkyl-$NHC_{1-4}$alkyl, —$C_{1-6}$alkylN$(C_{1-4}$alkyl$)_2$, —$C_{1-6}$alkyl-CN, —$NHC(O)C_{1-4}$alkyl, —$C(O)NHC_{1-4}$alkyl and —$C(O)N(C_{1-4}$alkyl$)_2$;

and more particularly, when $R^1$ is HAR, HAR is selected from:

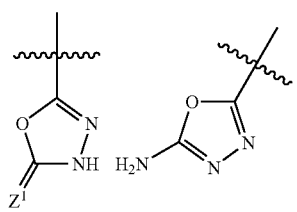

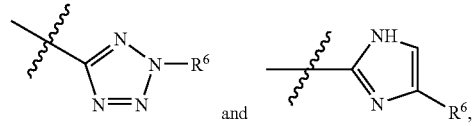

wherein $R^6$ is selected from —H, —$C_{1-3}$alkyl, —$C_{3-6}$cycloalkyl, —F and —Cl; and wherein all remaining variables are as originally defined in formula I.

In another aspect of the invention that is of interest, a compound of formula I is disclosed wherein: d and e are integers independently selected from 0, 1, 2 and 3, provided that the sum of d plus e is 1-3. Within this aspect of the invention, all other variables are as originally defined in formula I.

In another aspect of the invention that is of interest, a compound of formula I is disclosed wherein: X represents a bond, —O or —$S(O)_p$—, and more particularly X is —O—. Within this aspect of the invention, all other variables are as originally defined in formula I.

In another aspect of the invention that is of interest, a compound of formula I is disclosed wherein: $R^2$, $R^3$, $R^4$ and $R^5$ are independently selected from the group consisting of —H, —$C_{1-6}$ alkyl, —$OC_{1-6}$alkyl, —OH, -fluoro, -fluoro$C_1$-alkyl, -fluoro$C_{1-6}$alkoxy and —$N(R^a)_2$. Within this aspect of the invention, all other variables are as originally defined in formula I.

In an aspect of the invention that is of particular interest, a compound of formula I is described wherein: —$(CR^2R^3)_d$—X—$C(R^4R^5)_e$— represents —O—$CH_2$— or —$CH_2CH_2$—. Within this aspect of the invention, d represents 0 (zero); X represents —O— or a bond, e represents 1 or 2, $R^4$ and $R^5$ each represent —H, and all other variables are as originally defined in formula I.

In another aspect of the invention that is of interest, a compound of formula I is described wherein Y is HAR. Within this aspect of the invention, all other variables are as originally defined in formula I.

Another aspect of the invention that is of interest relates to a compound of formula I wherein Y represents HAR selected from the group consisting of:

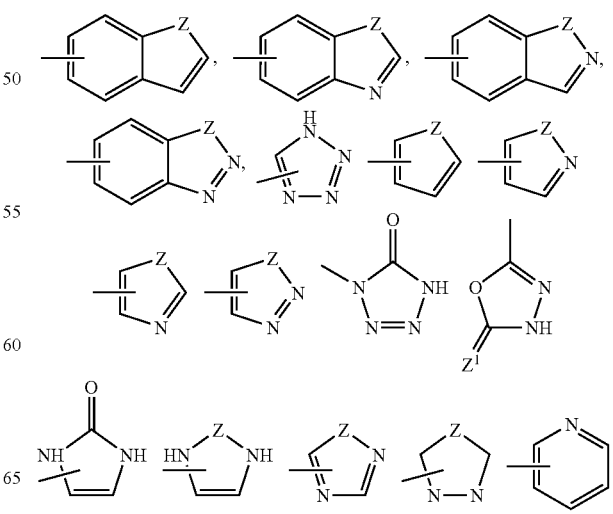

13

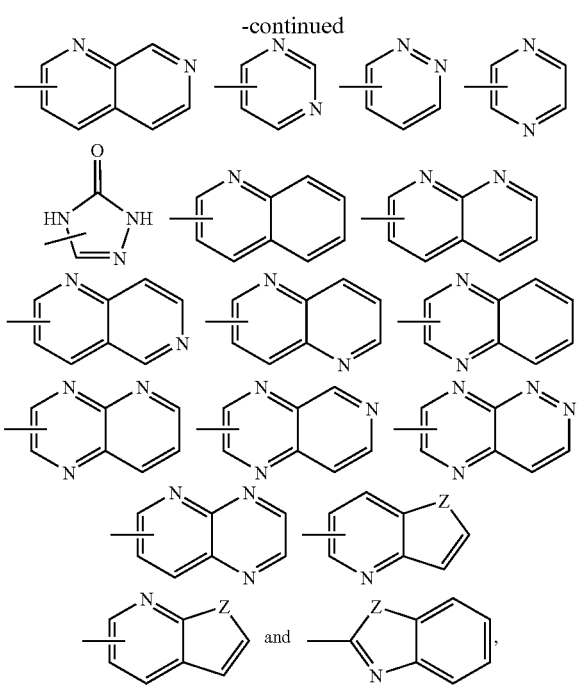

wherein Z represents O, S or NH; and $Z^1$ represents O or S.

Within this aspect of the invention, all other variables are as originally defined in formula I. More particularly, an aspect of the invention that is of interest relates to a compound of formula I wherein Y is HAR selected from the group consisting of:

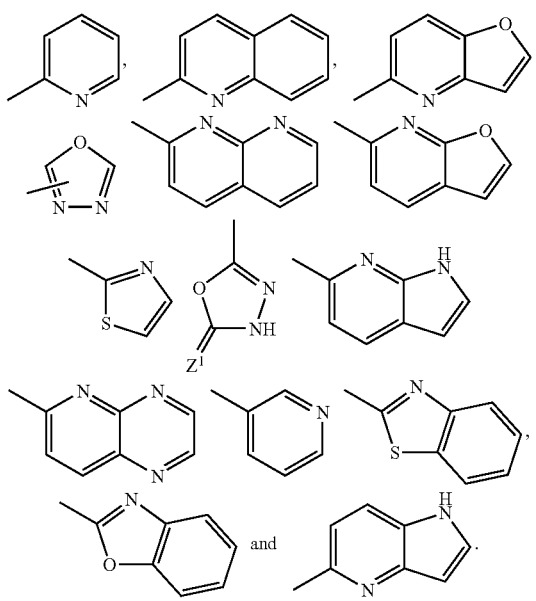

Within this aspect of the invention, all other variables are as originally defined in formula I.

In another aspect of the invention that is of interest, each $R^a$ is independently selected from the group consisting of —H and:

14

(a) —$C_{1-4}$alkyl, $C_{3-6}$cycloalkyl, $C_{3-6}$alkenyl, $C_{3-6}$alkynyl, each optionally substituted with 1-3 fluoro groups or a member selected from the group consisting of: —$OC_{1-6}$alkyl, —CN, —$NH_2$, —$NHC_{1-4}$alkyl and —$N(C_{1-4}$alkyl$)_2$;

(b) Aryl or Ar—$C_{1-6}$alkyl-, the aryl portions being optionally substituted with a member selected from —F, —Cl, —$C_{1-4}$ alkyl, —CN, —$OC_{1-6}$ alkyl, -fluoro$C_{1-4}$ alkyl, -fluoro$C_{1-4}$alkoxy, —$C_{1-4}$alkyl$NH_2$, —$C_{1-4}$alkyl$NHC_{1-4}$ alkyl, —$C_{1-4}$ alkyl$N(C_{1-4}$alkyl$)_2$, —$NH_2$, —$NHC_{1-4}$alkyl, —$N(C_{1-4}$alkyl$)_2$, —$NHC(O)C_{1-4}$alkyl, —$C(O)NHC_{1-4}$alkyl, —$C(O)N(C_{1-4}$alkyl$)_2$, —$CO_2H$, and —$CO_2C_{1-6}$alkyl;

and the alkyl portion of Ar—$C_{1-6}$alkyl- being optionally substituted with —F, —$OC_{1-6}$alkyl, —$NH_2$, —$NHC_{1-4}$alkyl, —$N(C_{1-4}$alkyl$)_2$;

(c) Hetcy or Hetcy-$C_{1-6}$ allyl-, each being optionally substituted on carbon with 1-2 members selected from the group consisting of: —F, —$CO_2H$, —$C_{1-6}$alkyl, —$CO_2C_{1-6}$alkyl, —$OC_{1-6}$alkyl, —$NH_2$, —$NHC_{1-4}$alkyl, —$N(C_{1-4}$alkyl$)_2$, —$NHC(O)C_{1-4}$alkyl, oxo, —$C(O)NHC_{1-4}$alkyl and —$C(O)N(C_{1-4}$alkyl$)_2$; and on nitrogen, when present, with —$C_{1-6}$alkyl or —$C_{1-6}$acyl; and the alkyl portion of Hetcy-$C_{1-6}$alkyl- being optionally substituted with —F, —$OC_{1-6}$alkyl, —$NH_2$, —$NHC_{1-4}$alkyl and —$N(C_{1-4}$alkyl$)_2$;

(d) HAR or HAR-$C_{1-6}$alkyl-, said HAR and HAR portion of HAR-$C_{1-6}$alkyl-optionally substituted with —F, —Cl, —Br, —$C_{1-6}$ alkyl, —CN, —$OC_{1-6}$ alkyl, -fluoro$C_{1-6}$ alkyl, -fluoro$C_{1-6}$ alkoxy$NH_2$, —$NHC_{1-4}$alkyl, —$N(C)_{1-4}$alkyl$)_2$, —$NHC(O)C_{1-4}$alkyl, —$C(O)NHC_{1-4}$alkyl, —$C(O)N(C_{1-4}$alkyl$)_2$, —$CO_2H$, —$CO_2C_{1-6}$alkyl; and the alkyl portion of HAR-$C_{1-6}$alkyl- being optionally substituted with —F, —$OC_{1-6}$alkyl, —$NH_2$, —$NHC_{1-4}$alkyl and —$N(C_{1-4}$alkyl$)_2$. Within this aspect of the invention, all other variables are as originally defined with respect to formula I.

In another aspect of the invention that is of interest, each $R^b$ is selected from the group consisting of —H and —$C_{1-10}$alkyl optionally substituted with 1-3 fluoro groups.

An aspect of the invention that is of particular interest relates to a compound of formula I wherein the bicyclic ring portion:

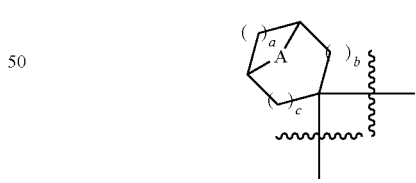

is selected from the group consisting of:

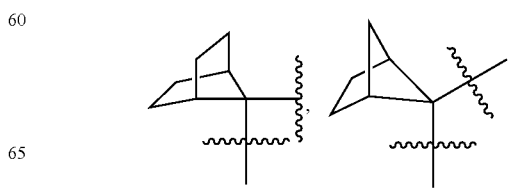

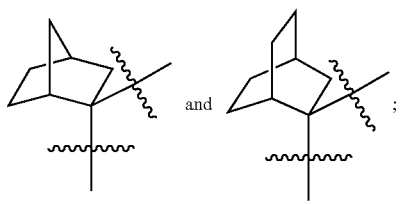

—(CR²R³)$_d$—X—(CR⁴R⁵)$_e$—Y—(R¹ᵃ)$_2$ is selected from the group consisting of:

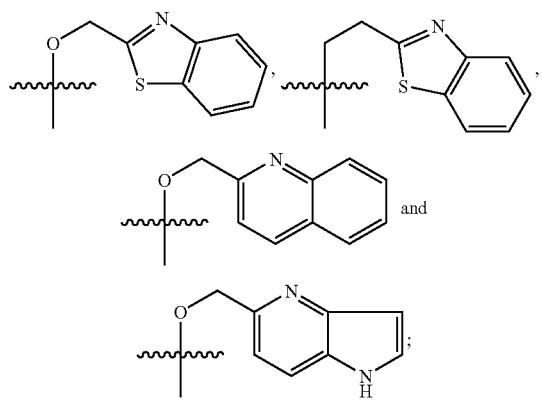

and R¹ is selected from the group consisting of:

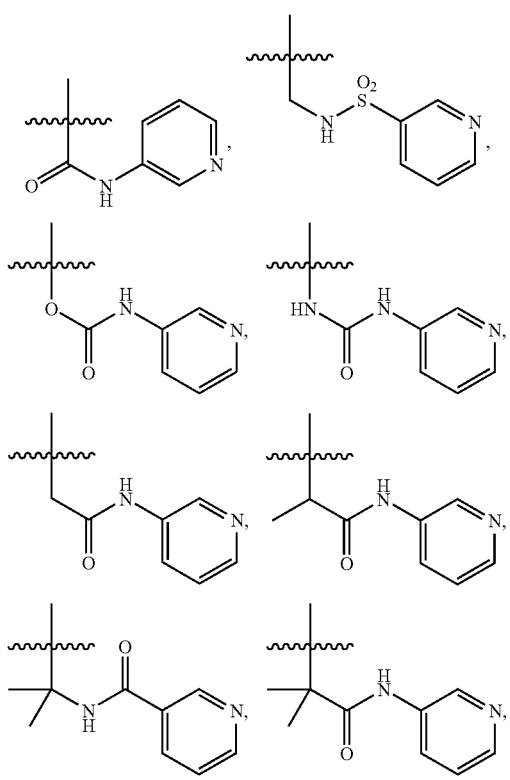

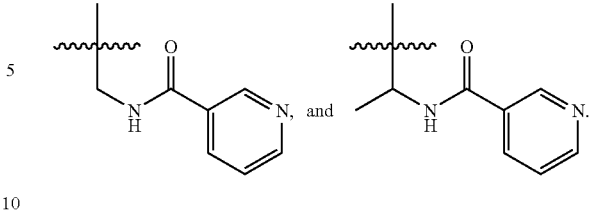

Examples of compounds that fall within the present invention include those shown in the examples contained herein, as well as salts and solvates thereof. When racemic mixtures are shown, the specific enantiomers are also included, as are the salts and solvates of the specific enantiomers.

The compounds of formula I can be used for the treatment of atherosclerosis comprising administering a therapeutically effective amount of a compound of Formula I to a patient in need of such treatment. A further aspect of this invention involves a method for preventing or reducing the risk of developing atherosclerosis, comprising administering a prophylactically effective amount of a compound of formula I to a patient in need of such treatment. Atherosclerosis is characterized by the deposition of atheromatous plaques containing cholesterol and lipids on the innermost layer of the walls of large and medium-sized arteries. Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction, are all clinical manifestations of atherosclerosis and are therefore encompassed by the terms "atherosclerosis" and "atherosclerotic disease."

A FLAP inhibitor may be administered to prevent or reduce the risk of occurrence, or recurrence where the potential exists, of a coronary heart disease event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Accordingly, the instant invention also provides a method for preventing or reducing the risk of a first or subsequent occurrence of an atherosclerotic disease event comprising the administration of a prophylactically effective amount of a FLAP inhibitor to a patient at risk for such an event. The patient may already have atherosclerotic disease at the time of administration, or may be at risk for developing it.

The method of this invention particularly serves to prevent or slow new atherosclerotic lesion or plaque formation, and to prevent or slow progression of existing lesions or plaques, as well as to cause regression of existing lesions or plaques. Accordingly, one aspect of this invention involves a method for halting or slowing the progression of atherosclerosis, including halting or slowing atherosclerotic plaque progression, comprising administering a therapeutically effective amount of a FLAP inhibitor to a patient in need of such treatment. This method also includes halting or slowing progression of atherosclerotic plaques existing at the time the instant treatment is begun (i.e., "existing atherosclerotic plaques"), as well as halting or slowing formation of new atherosclerotic plaques in patients with atherosclerosis.

Another aspect of this invention involves a method for regression of atherosclerosis, including regression of atherosclerotic plaques existing at the time the instant treatment is begun, comprising administering a therapeutically effective amount of a FLAP inhibitor to a patient in need of such treatment. Another aspect of this invention involves a method for preventing or reducing the risk of atherosclerotic plaque rupture comprising administering a prophylactically effective amount of a FLAP inhibitor to a patient in need of such treatment.

The ability of the compounds of Formula I to inhibit biosynthesis of the leukotrienes makes them useful for preventing or reversing the symptomsinduced by the leukotriens in a human subject. Therefore, additional aspects of this invention involve a method for preventing the synthesis, the action, or the release of leukotrienes in a patient which comprises administering to the patient an effective amount of a compound of Formula I; a method for treating a leukotriene-mediated medical condition comprising administering a therapeutically effective amount of a compound of Formula I to a patient need of such treatment; and a method of preventing or reducing the risk for a leukotriene-mediated medical condition comprising administering a prophylactically effective amount of a compound of Formula I to a patient in need of such treatment. This inhibition of the mammalian biosynthesis of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as atopic eczema, and the like, 6) cardiovascular disorders such as angina, formation of atherosclerotic plaques, myocardial ischemia, hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecysitis, 16) multiple selerosis, and 17) proliferation of myoblastic leukemia cells.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also act as inhibitors of tumor metastasis and exhibit cytoprotective action.

The FLAP inhibitors of this invention can also be administered for prevention, amelioration and treatment of glomerulonephritis (see Guasch A., Zayas C.F., Badr K F. (1999), "MK-591 acutely restores glomerular size selectivity and reduces proteinuria in human glomerulonephritis," Kidney Int., 56:261-267); and also for and prevention, amelioration and treatment of kidney damage resulting from diabetes complications (see Valdivielso J M, Montero A., Badr K F., Munger K A. (2003), "Inhibition of FLAP decreases proteinuria in diabetic rats," J. Nephrol., 16(1):85-940.)

In addition, the compounds of this invention can also be used for the treatment of chronic obstructive pulmonary disease (COPD). As described in S. Kilfeather, Chest, 2002, vol 121, 197, airway neutrophilia in COPD patients is believed to be a contributing source of inflammation and is associated with airway remodeling. The presence of neutrophils is mediated in part by $LTB_4$, and treatment with the instant compounds could be used to reduce neutrophilic inflammation in patients with COPD.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like. Two assays can be used to measure cytoprotective ability. These assays are: (A) an ethanol-induced lesion assay and (B) an indomethacin-induced ulcer assay and are described in EP 140,684.

In particular, the compounds of the invention would be useful to reduce the gastric erosion caused by co-administration of a cyclooxygenase-2 selective inhibitor and low-dose aspirin. Cyclooxygenase-2 selective inhibitors are widely used as effective anti-inflammatory drugs with less potential for gastrointestinal complications as compared to traditional, non-selective non-steroidal anti-inflammatory drugs. However, the combined use of a cyclooxygenase-2 selective inhibitor with low-dose aspirin for cardio protection may compromise the gastrointestinal safety of this class of compounds. By virtue of its activity as a 5-lipoxygenase inhibitor, the compounds of the invention would be expected to be gastric protective in this regard. See Fiorucci, et al. FASEB J. 17:1171-1173, 2003. Cyclooxygenase-2 selective inhibitors for use with the invention include but are not limited to rofecoxib (VIOXX®), etoricoxib (ARCOXIA™), celecoxib (CELEBREX®) and valdecoxib (BEXTRA™). A compound of this invention in combination with a cyclooxygenase-2 selective inhibitor could be administered in unit dosage form or separately to a patient on low-dose aspirin therapy. Alternatively, the cyclooxygenase-2 inhibitor could be administered in unit dosage form with low-dose aspirin, in which case a compound of this invention would be administered separately. All three active ingredients in unit dosage form is also encompassed. Conventional dosage amounts of the cyclooxygenase-2 selective inhibitor and aspirin (for cardio protection) may be utilized. For example, rofecoxib could be administered at 12.5 mg, 25 mg or 50 mg once daily. Aspirin could be administered at 81 mg once daily.

In general, FLAP inhibitors can be identified as those compounds which have an $IC_{50}$ in the "FLAP Binding Assay" that is less than or equal to 1 µM, and preferably 500 nM or less.

The term "patient" includes mammals, especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of onset of atherosclerosis.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician.

An effective amount of a FLAP inhibitor in the method of this invention is in the range of about 0.001 mg/kg to about 100 mg/kg of body weight per day, preferably 0.01 mg to about 10 mg per kg, and most preferably 0.1 to 1 mg per kg, in single or divided doses. A single daily dose is preferred but not necessary. On the other hand, it may be necessary to use dosages outside these limits in some cases. As examples, the daily dosage amount may be selected from, but not limited to 25 mg, 50 mg, 75 mg, 100 mg, 125 mg, 150 mg, 200 mg and 250 mg. It will be understood, however, that the specific dose level for any particular patient will depend upon a variety of factors including the age, body weight, general health, sex, diet, time of administration, route of administration, rate of excretion, drug combination and the severity of the patient's condition. A consideration of these factors is well within the purview of the ordinarily skilled clinician for the purpose of determining the therapeutically effective or prophylactically effective dosage amount needed to prevent, counter, or arrest the progress of the condition. It is expected that the FLAP inhibitor will administered chronically on a daily basis for a length of time appropriate to treat or prevent the medical condition relevant to the patient, including a course of therapy lasting months, years or the life of the patient.

In a broad embodiment, any suitable additional active agent or agents, including but not limited to anti-atherosclerotic agents, may be used in combination with the compound of formula I in a single dosage formulation, or may be administered to the patient in a separate dosage formulation, which allows for concurrent or sequential administration of the active agents. One or more additional active agents may be administered with a compound of Formula I. The additional active agent or agents can be lipid modifying compounds or agents having other pharmaceutical activities, or agents that have both lipid-modifying effects and other pharmaceutical activities. Examples of additional active agents which may be employed include but are not limited to HMG-CoA reductase inhibitors, which include statins in their lactonized or dihydroxy open acid forms and pharmaceutically acceptable salts and esters thereof, including but not limited to lovastatin (see U.S. Pat. No. 4,342,767), simvastatin (see U.S. Pat. No. 4,444,784), dihydroxy open-acid simvastatin, particularly the ammonium or calcium salts thereof, pravastatin, particularly the sodium salt thereof (see U.S. Pat. No. 4,346,227), fluvastatin particularly the sodium salt thereof (see U.S. Pat. No. 5,354,772), atorvastatin, particularly the calcium salt thereof (see U.S. Pat. No. 5,273,995), pitavastatin also referred to as NK-104 (see PCT international publication number WO 97/23200) and rosuvastatin, also known as ZD-4522, (CRESTOR®; see U.S. Pat. No. 5,260,440, and Drugs of the Future, 1999, 24(5), pp. 511-513); 5-lipoxygenase inhibitors; cholesterol ester transfer protein (CETP) inhibitors, for example JTT-705 and torcetrapib, also known as CP529,414; HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; niacin; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example pioglitazone and rosiglitazone and, including those compounds included within the structural class known as thiazolidinediones as well as those PPARγ agonists outside the thiazolidine dione structural class; PPARα agonists such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABCA1 gene expression; FXR and LXR ligands including both inhibitors and agonists; bisphosphonate compounds such as alendronate sodium; and cyclooxygenase-2 inhibitors such as rofecoxib and celecoxib.

Still another type of agent that can be used in combination with the compounds of this invention are cholesterol absorption inhibitors. Cholesterol absorption inhibitors block the movement of cholesterol from the intestinal lumen into enterocytes of the small intestinal wall. This blockade is their primary mode of action in reducing serum cholesterol levels. These compounds are distinct from compounds which reduce serum cholesterol levels primarily by mechanisms of action such as acyl coenzyme A—cholesterol acyl transferase (ACAT) inhibition, inhibition of triglyceride synthesis, MTP inhibition, bile acid sequestration, and transcription modulation such as agonists or antagonists of nuclear hormones. Cholesterol absorption inhibitors are described in U.S. Pat. Nos. 5,846,966, 5,631,365, 5,767,115, 6,133,001, 5,886,171, 5,856,473, 5,756,470, 5,739,321, 5,919,672, WO 00/63703, WO /0060107, WO 00/38725, WO 00/34240, WO 00/20623, WO 97/45406, WO 97/16424, WO 97/16455, and WO 95/08532.

An exemplary cholesterol absorption inhibitor is ezetimibe, also known as SCH-58235, which is 1-(4-fluorophenyl)-3(R)-[3(S)-(4-fluorophenyl)-3-hydroxypropyl)]-4 (S)-(4-hydroxyphenyl)-2-azetidinone, described in U.S. Pat. Nos. 5,767,115 and 5,846,966 and shown below as

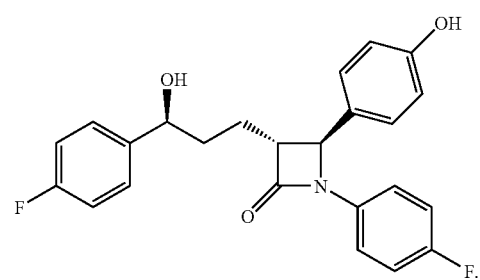

Additional exemplary hydroxy-substituted azetidinone cholesterol absorption inhibitors are specifically described in U.S. Pat. No. 5,767,115, column 39, lines 54-61 and column 40, lines 1-51, represented by the formula

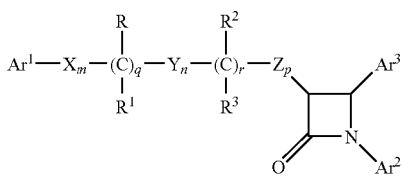

as defined in column 2, lines 20-63. These and other cholesterol absorption inhibitors can be identified according to the assay of hypolipidemic compounds using the hyperlipidemic hamster described in U.S. Pat. No. 5,767,115, column 19, lines 47-65, in which hamsters are fed a controlled cholesterol diet and dosed with test compounds for seven days. Plasma lipid analysis is conducted and data is reported as percent reduction of lipid versus control.

Therapeutically effective amounts of cholesterol absorption inhibitors include dosages of from about 0.01 mg/kg to about 30 mg/kg of body weight per day, preferably about 0.1 mg/kg to about 15 mg/kg. For an average body weight of 70 kg, the dosage level is therefore from about 0.7 mg to about 2100 mg of drug per day, e.g. 10, 20, 40, 100 or 200 mg per day, preferably given as a single daily dose or in divided doses two to six times a day, or in sustained release form. This dosage regimen may be adjusted to provide the optimal therapeutic response when the cholesterol absorption inhibitor is used in combination with a compound of the instant invention.

In the method of treatment of this invention, the FLAP inhibitors may be administered via any suitable route of administration such as orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred.

For oral use, the pharmaceutical compositions of this invention containing the active ingredient may be in forms such as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Oral immediate-release and time-controlled release dosage forms may be employed, as well as enterically coated oral dosage forms. Tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. One example of a time-controlled release device is described in U.S. Pat. No. 5,366,738. They may also be coated by the technique described in U.S. Pat. Nos. 4,256,108; 4,166,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds useful in the method of treatment of the invention may also be administered in the form of a suppository for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier.

A therapeutically effective amount of a compound of Formula I can be used for the preparation of a medicament useful for treating or preventing any of the medical conditions described herein, in dosage amounts described herein. For example, a compound of Formula I can be used for the preparation of a medicament useful for the treatment of asthma, allergies and allergic conditions, inflammation, COPD or erosive gastritis. Additionally, the medicament may be useful for preventing or reducing the risk of developing atherosclerotic disease, halting or slowing the progression of atherosclerotic disease once it has become clinically manifest, and preventing or reducing the risk of a first or subsequent occurrence of an atherosclerotic disease event. The medicament comprised of a compound of Formula I may also be prepared with one or more additional active agents, such as those described herein.

The compounds of structural formula I of the present invention can be prepared according to the procedures of the following Schemes and Examples, using appropriate materials and are further exemplified by the specific examples which follow. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, or potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as HATU, EDC, and PyBOP in an inert solvent such as dichloromethane or DMF in the presence of a auxiliary nucleophile such as HOAT or HOBT. The use of protecting groups for the amine and carboxylic acid functionalities to facilitate the desired reaction and minimize undesired reactions is well documented. Conditions required to add and remove protecting groups are found in standard textbooks such as Greene, T, and Wuts, P. G. M., *Protective Groups in Organic Synthesis*, John Wiley & Sons, Inc., New York, N.Y., 1999. CBZ and BOC are commonly used amino protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, dioxane, methanol, or ethyl acetate.

Abbreviations
  Ar Aryl
  9-BBN 9-Borabicyclo[3.3.1]nonane
  BOC (Boc) tert-butyloxycarbonyl
  Bn benzyl
  Bu butyl
  $^t$Bu tert-butyl
  celite Celite™ diatomaceous earth
  CBZ (Cbz) benzyloxycarbonyl
  DEAD diethyl azodicarboxylate
  Dess-Martin Periodinane 1,1,1-tris(acetyloxy)-1,1-dihydro1,2-benzodoxol-3-(1H)-one
  DIAD diisopropylazodicarboxylate
  DIBAL-H diisobutylaluminum hydride
  DIPEA diisopropylethylamine
  DMAP 4-dimethylaminopyridine
  DMF N,N-dimethylformamide
  dppf 1,1'-Bis(diphenylphosphino)ferrocene
  EDC 1-(3-dimethylaminopropyl)$_3$-ethylcarbodiimide-.HCl
  equiv. equivalent(s)
  ES-MS electron spray ion-mass spectroscopy
  Et ethyl
  EtOAc ethyl acetate
  h hour(s)
  HATU O-(7-azabenzotriazol-1-yl)-1,1,3,3-tetramethyluronium hexafluorophosphate
  HetAr or HAR Heteroaryl
  HOAt 1-hydroxy-7-azabenzotriazole
  HOBt 1-hydroxybenzotriazole hydrate
  HPLC high performance liquid chromatography
  i iso
  LDA lithium diisopropylamide
  LG leaving group Me methyl
min minute(s)
m.p. melting point
MS mass spectrum
Ms methanesulfonyl
NMM N-Methylmorpholine
NMO N-Methylmorpholine-N-oxide
NMP 1-methyl-2-pyrrolidinone
p para
PCC pyridinium chlorochromate
Ph phenyl
Pr propyl
$^i$Pr isopropyl
p-TSA para-toluenesulfonic acid
PyBOP benzotriazol-1-yloxytripyrrolidinephosphonium hexafluorophosphate
Tf trifluoromethanesulfonyl
TFA trifluoroacetic acid
THF tetrahydrofuran Reaction schemes A-M illustrate preferred methods for the syntheses of compounds of the present invention of structural formula I. All substituents are as defined above unless indicated otherwise.

Reaction scheme A illustrates the preferred methods for the synthesis of a ketone of type 1. In general, 1 can be either purchased commercially or synthesized according to literature methods. An alcohol of type 2 or an alkene of type 3 can also be used to prepare 1, using known methods in organic synthesis. For example, 2 can be converted to 1 using a direct oxidation protocol. A preferred method for effecting such a transformation may involve treatment of 2 with any agent capable of oxidizing carbon-oxygen single bonds, such as the Dess-Martin Periodinane, PCC, TPAP or the like. In another method, 3 can also be converted to 1 using a two-step hydroboration-oxidation sequence. In this case, 3 is first treated with a suitable hydroborating agent such as 9-BBN, diborane or the like, to generate the intermediary alkyl borane. The latter species is generally not isolated, but oxidized in situ to 2. The latter can then be converted to 1 using the aforementioned oxidation methods.

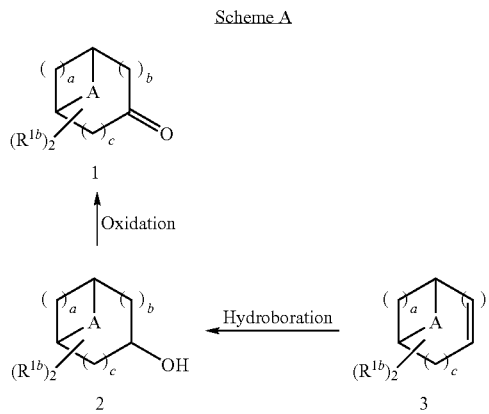

Scheme A

Some useful literature references for the preparation of 1 include: LeBel, N. A., Liesemer, R. N. *J. Am. Chem. Soc.* 1965, 87, 4301; Gibson, T. *J. Org. Chem.* 1972, 37, 700; Nicolaou, K. C., Magolda, R. L., Claremon, D. A., *J. Am. Chem. Soc.* 1980, 102, 1404; Meltzer, P. C.; Blundell, P., Chen, Z., Yong, Y. F., Madras, B. K., *Bioorg. Med. Chem. Let.* 1999, 9, 857.

Reaction scheme B illustrates the preferred method of synthesis of a compound of type 8. In this method, 1 is treated with an organometallic reagent of type 4, capable of transferring an aryl group. Preferred organometallic reagents for this transformation include organomagnesium (Grignard) or organolithium compounds. When Grignard reagents are employed as shown in scheme B, it is customary to conduct the reaction in a suitable ethereal solvent such as diethyl ether, THF or mixtures thereof, at temperatures between –78° C. and the boiling temperature of the solvent. In the case of an organolithium reagent, the reaction can be conducted in a variety of solvents such as diethyl ether or hexanes, at temperatures between –78° C. and room temperature. The Grignard and the organolithium reagents are often purchased commercially, but can be prepared synthetically according to known methods in organic synthesis. The product from this reaction is an alcohol of type 5, which can be arylated in an electrophilic aromatic substitution process called the Friedel-Crafts reaction. Typical conditions for effecting such an arylation include generation of an intermediate tertiary carbocation of type 7, derived from 5, followed by in situ trapping with a suitable aromatic-coupling partner of type 6. Formation of 7 may occur spontaneously in solution or it may be promoted with a reagent capable of ionizing 5, like a protic acid such as p-TSA, or concentrated hydrochloric acid or a suitable Lewis acid. In certain cases, it may be preferable to conduct the reaction in the presence of a free radical scavenger such as 3-mercaptopropionic acid or the like. The reaction is conducted typically in an inert organic solvent, at temperatures between –20° C. and the boiling temperature of the solvent. The product is a compound of type 8, which can be elaborated to compounds of the present invention as described in the subsequent schemes.

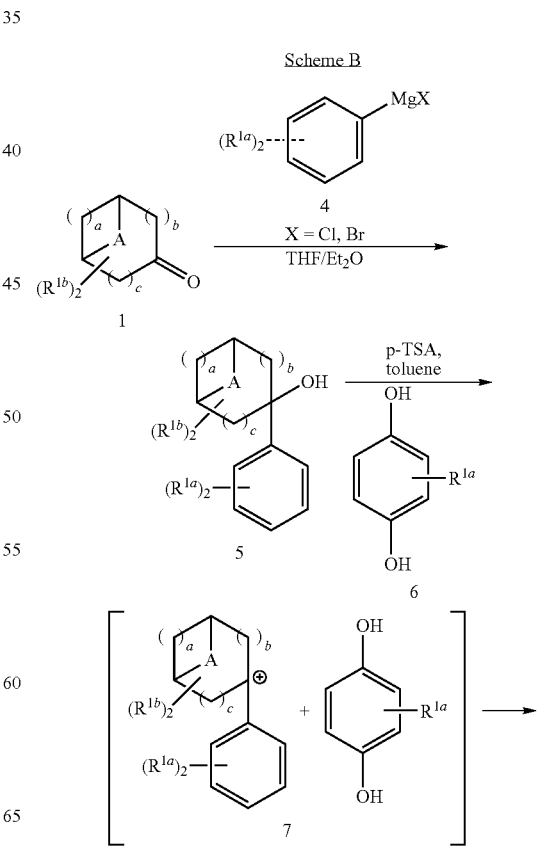

Scheme B

-continued

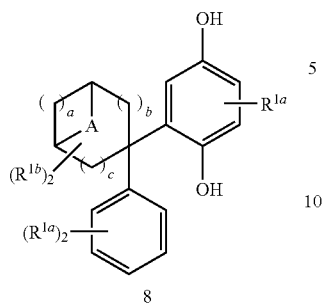

8

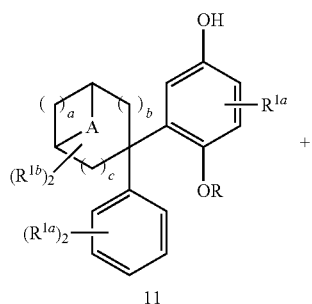

11

Reaction scheme C illustrates the preferred method of synthesis of a compound of structural formula 10 in which it is desirable to first elaborate the more reactive hydroxyl group (1-position) of 8. For example, 8 can be directly alkylated using an alkylating agent of type 9. The reaction is conducted typically in the presence of a suitable base such as potassium carbonate or cesium carbonate, in a polar aprotic solvent such as DMF, in which the substituent LG of 9 is a good leaving group such as halide, mesylate or triflate. The major products from the reaction are the mono-alkylated product of structural formula 10 and the bis-alkylated product of structural formula 12 which can be readily separated by flash chromatography. In some cases, a small amount of the regioisomeric mono-alkylated product of type 11 is also observed. In 10, as in the rest of the following schemes, the OR or other group shown at position 1 is equivalent to $-(CR_2R_3)_d-X-(CR_4R_5)_e-Y-(R^{1a})_2$ of formula I and the 4-position OR or other group, such as in formula 12, is equivalent to $R^1$ of formula I.

Scheme C

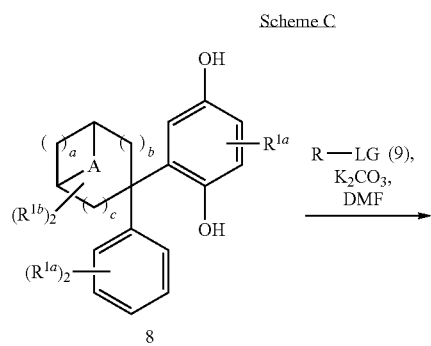

Reaction scheme D illustrates a protecting group strategy for the synthesis of a compound of type 15 in which it is desirable to first elaborate the less reactive hydroxyl group (4-position) of 8. For example, the more reactive hydroxyl group (1-position) of 8 can be selectively protected using a silicon based protecting group approach. In this method, 8 is treated with a suitable silylating agent such as chloro-tert-butyldiphenylsilane, in the presence of imidazole, in a solvent like DMF. The reaction is conducted typically at temperatures between 0° C. and room temperature, for periods of 12-24 h. The product is a silyl ether of type 13, which can be directly alkylated using the conditions described in the discussion for scheme C. The silicon protecting group can be removed by any of the appropriate desilylation methods such as treatment with TBAF in THF or hydrogen fluoride in pyridine and the product of this reaction is a phenol of type 15.

Scheme D

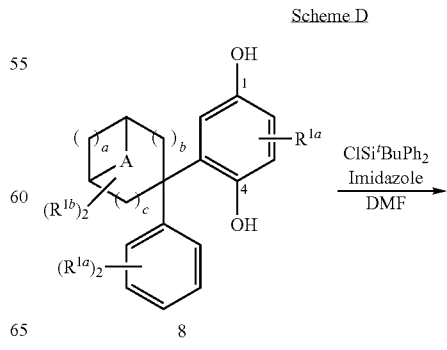

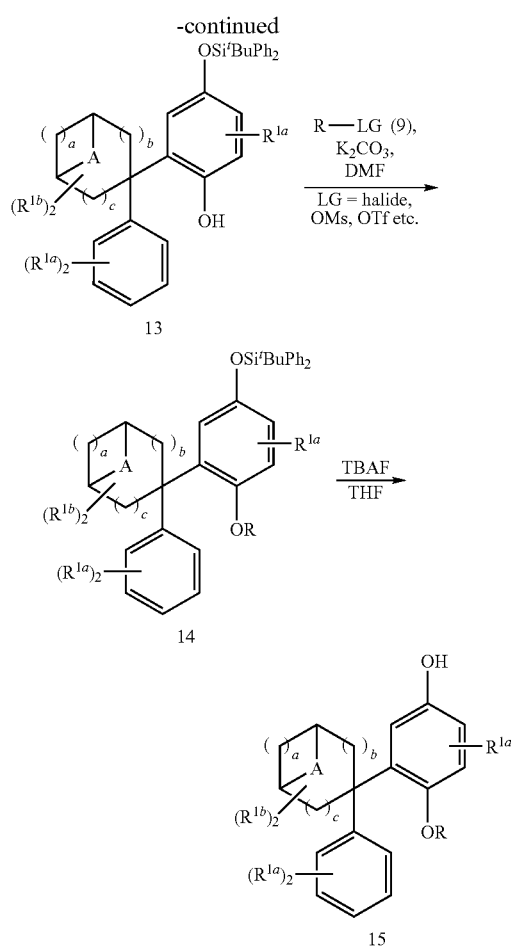

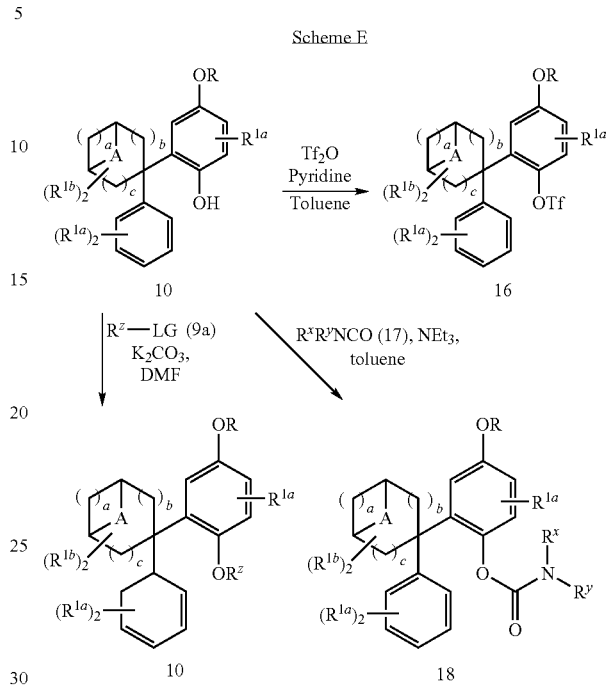

Reaction scheme E illustrates some of the preferred methods of elaboration of 10. For example, 10 can be treated with a triflating agent such as triflic anhydride or the like in the presence of a suitable base such as pyridine or triethylamine in an aprotic solvent like toluene. It is customary to conduct the reaction at temperatures between −78° C. and room temperature, for periods of 1-24 h. The product of the reaction is a triflate of structural formula 16 which can be elaborated by a variety of synthetic methods known to those skilled in organic synthesis, three of which are outlined in schemes F, G and H.

Alternatively, 10 can be treated with an isocyanate of type 17 in the presence of a suitable base such as triethylamine, in an inert solvent like toluene. Typically, 17 can be purchased commercially or prepared synthetically and the product of the reaction is a carbamate of structural formula 18. In certain cases it may be preferable to generate 17 in situ, and this is typically accomplished from an appropriate precursor such as an acyl azide. In an alternative method, 10 can be treated with a suitable carbonyl equivalent such as phosgene, triphosgene or carbonyl diimidazole. After a short period of time, typically between 0.1-1 hour, a primary or secondary amine is added and the product of the reaction is a carbamate of structural formula 18. The reaction sequence is conducted in a suitable inert organic solvent like methylene chloride, at temperatures between 0° C. and room temperature, for periods of 1-24 h.

In yet another example, 10 can be directly alkylated using the conditions described in the discussion of scheme C to afford a derivative of structural formula 19.

Reaction scheme F illustrates the preferred method of synthesis of compounds of structural formula 20, 21 and 22. In this method, 16 is treated with either allyltributylstannane or vinyltributylstannane in the presence of a suitable a palladium catalyst such as [1,1′-bis(diphenylphosphino)-ferrocene] dichloropalladium(II), in an inert organic solvent like DMW or NMP. The reaction is usually conducted at elevated temperatures, typically between 50-100° C., for periods of 2-24 h. In certain cases, it may be essential to use an additive such as lithium chloride to promote the reaction. Often, the reaction times can be significantly reduced if the reaction is conducted under microwave irradiation. The product of the reaction is an alkene of structural formula 20 which can be synthetically elaborated, using a variety of methods known in organic synthesis. For example, 20 can be oxidatively cleaved to afford an aldehyde of type 21, which can be further oxidized to a carboxylic acid derivative of structural formula 22. A preferred method for the oxidative cleavage reaction is the two step process shown in reaction scheme F. Alkene 20 is first oxidized to a vicinal diol using catalytic osmium tetraoxide in the presence of a stoichiometric reoxidant such as NMO, in a solvent system such as acetone-water. The intermediate vicinal diol which forms is generally not isolated, but is in turn subjected to cleavage with sodium periodate in a suitable mixed solvent system like THF-water to afford 21. Both steps in the oxidative cleavage sequence are generally completed during periods of several minutes to a few hours, at temperatures between 0° C. and room temperature. Alternatively, the oxidative cleavage of 20 may also be accomplished using ozone, or by other methods known to those skilled in the art. Aldehyde 21 can then be further oxidized to 22 using a buffered chlorite oxidation system. In this method, 21 is treated with sodium chlorite and monobasic sodium phosphate in the presence of a chlorine scavenger, such as 2-methyl-2-butene. The reaction is conducted typically in a solvent system like n-butanol-water, for periods of 1-6 h, at temperatures between 0° C. and room temperature. Both 21 and 22 can be elaborated in numerous ways known in organic synthesis to furnish other compounds of the present invention.

of structural formula 16a which can be converted to 22 (n=0) using a variety of hydrolytic methods known to those skilled in organic synthesis.

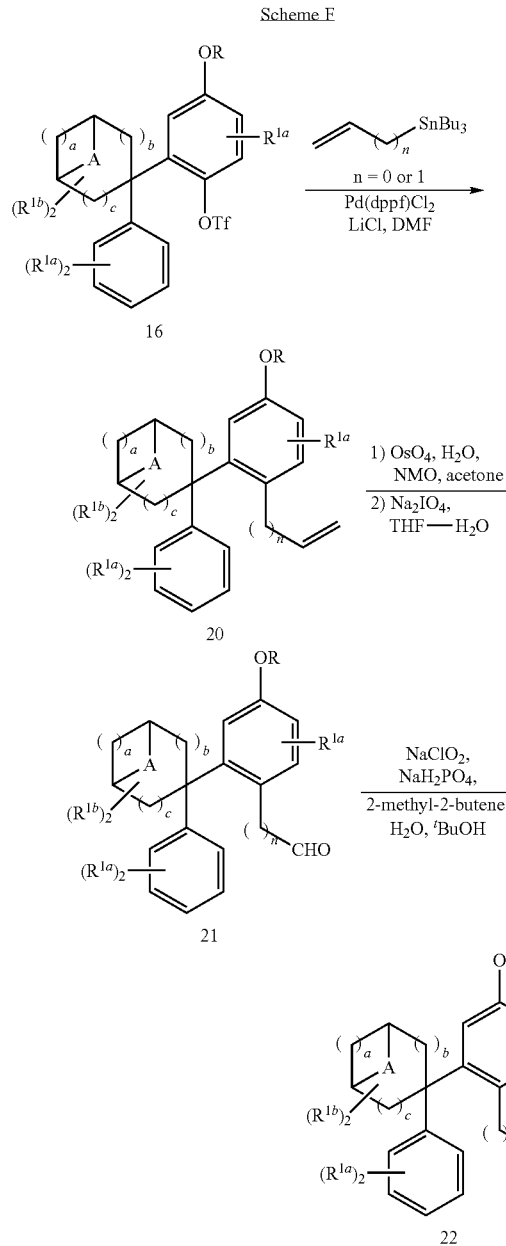

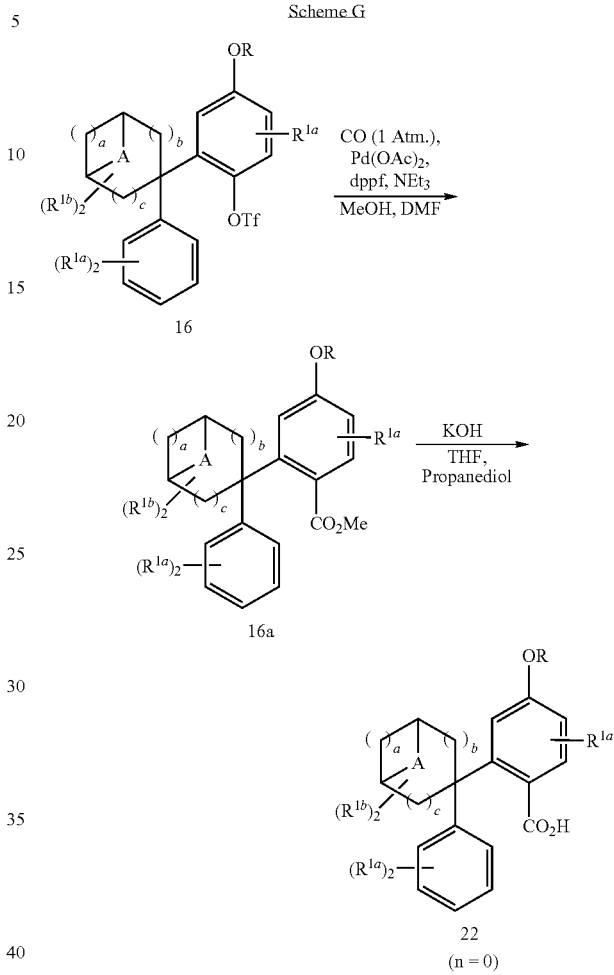

Reaction scheme G illustrates an alternative method of synthesis of compounds of structural formula 22 (n=0). In this method, 16 is treated with methanol in the presence of a suitable palladium catalyst such as [1,1'-bis(diphenylphosphino)-ferrocene]dichloropalladium(II) and a tertiary amine base such as triethylamine, in an inert organic solvent like DMF. The reaction is usually conducted at elevated temperature, typically between 50-100° C., for periods of 6-24 h, under an atmosphere of carbon monoxide. In certain cases it may be preferable to use elevated pressures of carbon monoxide or an additive such as lithium chloride to promote or accelerate the reaction. The product of the reaction is an ester Reaction scheme H illustrates the preferred method of synthesis of compounds of structural formula 24. In this method, commonly referred to as the Suzuki-Miyaura reaction, 16 is treated with an aryl- or heteroaryl-boronic acid of type 23 in the presence of a suitable palladium catalyst such as [1,1'-bis(diphenylphosphino)-ferrocene]dichloropalladium (II) and aqueous sodium carbonate. The reaction is usually performed in a suitable combination of inert organic solvents such as toluene-ethanol, at about 80° C., for a period of 6-24 h and the product is a biaryl of structural formula 24.

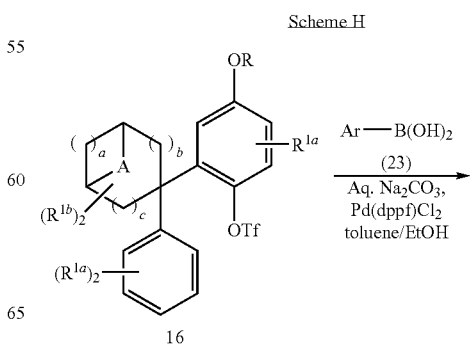

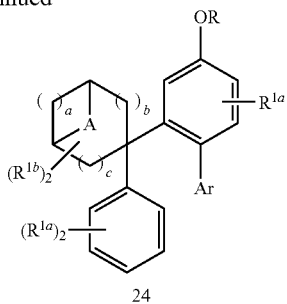

Reaction scheme I illustrates the synthetic methodology in the most general case in which 22 is treated with an amine of type 25 to afford an amide of structural formula 26. The amide bond coupling reaction illustrated in reaction scheme I is conducted in an appropriate inert solvent such as DMF, methylene chloride or the like and may be performed with a variety of reagents suitable for amide coupling reactions such as HATU, EDC or PyBOP. Preferred conditions for the amide bond coupling reaction shown in reaction scheme I are known to those skilled in organic synthesis. Such modifications may include, but are not limited to, the use of basic reagents such as triethylamine, DIPEA, or NMM, or the addition of an additive such as HOAt or HOBt. Alternatively, 25 may be treated with an activated ester or acid chloride derivative of 22, which also affords amides of structural formula 26. The amide bond coupling shown in reaction Scheme I is usually conducted at a temperatures between 0° C. and room temperature, occasionally at elevated temperatures, and the coupling reaction is typically conducted for periods of 1 to 24 h.

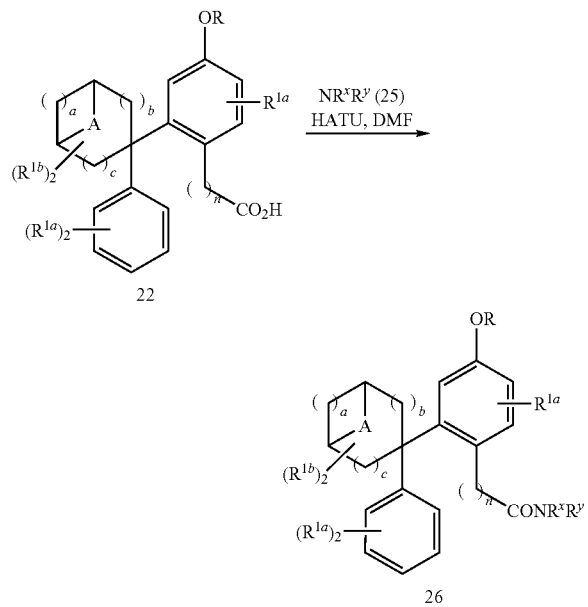

Reaction scheme J illustrates a preferred method of synthesis of a compound of structural formula 28. In this method, 22 is subjected to the Curtius reaction to afford a N-Boc protected amine of structural formula 27. The reaction is performed by reacting 22 with diphenylphosphoryl azide in the presence of a tertiary amine such as triethylamine or DIPEA in a solvent like toluene. The initial product is generally accepted to be the acyl azide, which is rearranged to the isocyanate in a thermal process analogous to the Wolff rearrangement of acyl carbenes. The rearrangment is conducted typically at the reflux temperature of the solvent, for instance 110° C., and the rearrangement is usually completed in periods of 1-5 h. The intermediate isocyanate which forms is generally not isolated, but is in turn subjected to in situ reaction with a suitable alcohol such as tert-butyl alcohol to afford amine of structural formula 27. The N-BOC group can be removed by a suitable deprotection method such as treatment with hydrogen chloride in EtOAc or TFA in methylene chloride. The deprotection is conducted typically at temperatures between 0° C. and room temperature, and the reaction is usually complete in 0.5-3 h. The product amine of structural formula 28 can be used as a coupling partner in reaction Scheme K or synthetically modified using a variety of methods known in organic synthesis to afford other compounds of the present invention.

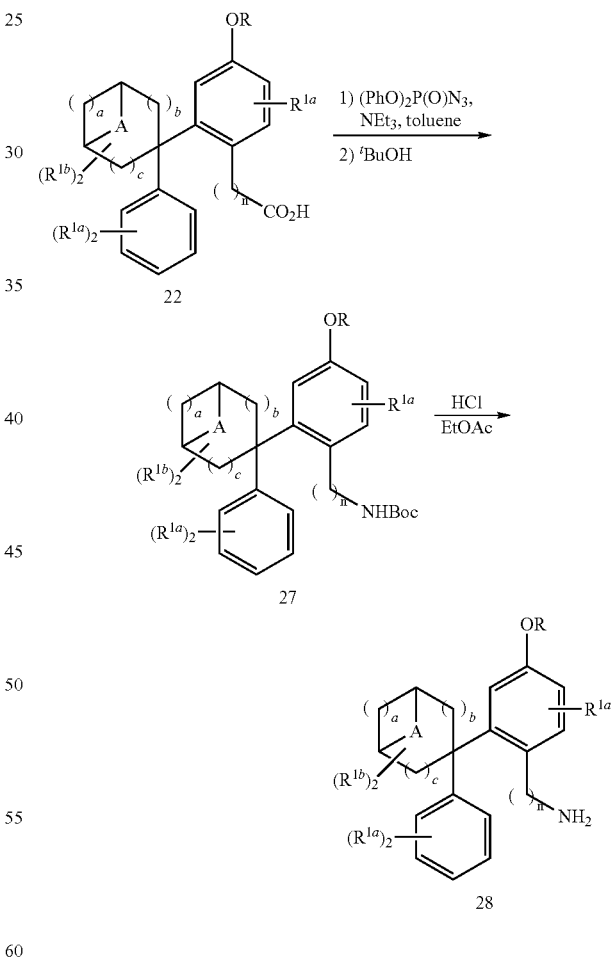

Reaction scheme K illustrates preferred methods for the syntheses of compounds of structural formula 31. For example, 28 can participate in amide bond coupling reactions with a carboxylic acid of type 29 to afford an amide of structural formula 31, using the reagents and conditions described for the generalized amide coupling protocol shown in reaction scheme I. Alternatively, 28 may also be treated with an activated ester or acid chloride derivative of type 30, which also affords 31. Typical conditions for effecting such a transformation include treatment of 28 with 30 in the presence of a tertiary amine base such as triethylamine. It is customary to perform the reaction in an inert organic solvent such as DMP or methylene chloride, at temperatures between 0° C. and the reflux temperature of the solvent, frequently at room temperature and for periods of 1-24 h.

subjected to a reductive amination reaction with an aldehyde or ketone of type 36 using the conditions described in the bottom of reaction scheme L to afford compounds of type 37.

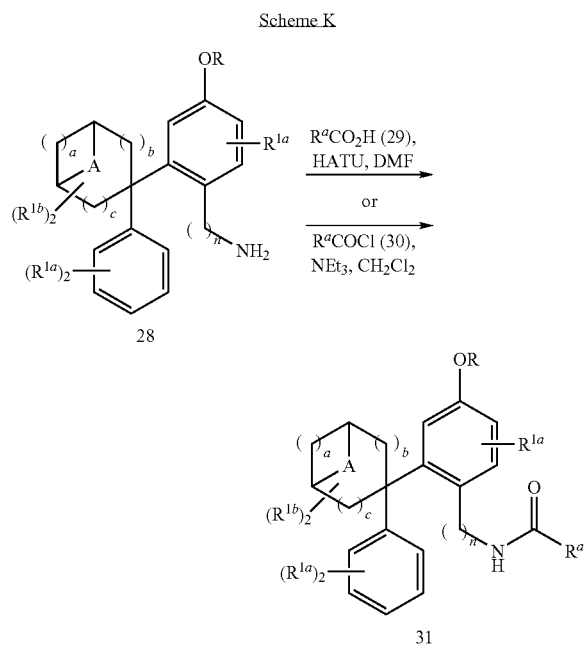

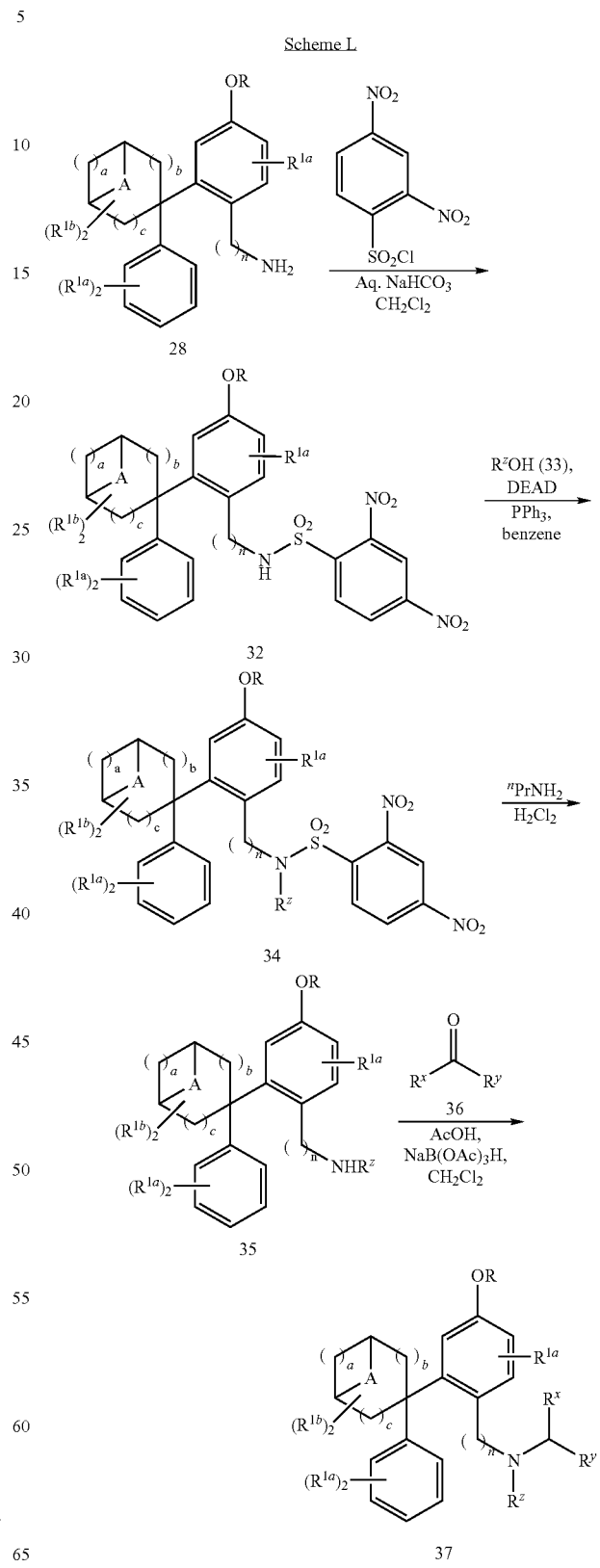

As shown in reaction scheme L, 28 can also be elaborated using the Fukuyama modification of the Mitsunobu reaction (Fukuyama, T.; Jow, C.-K.; Cheung, M. *Tetrahedron Lett.* 1995, 36, 6373-74). For example, 28 may be reacted with an arylsulfonyl chloride such as 2-nitrobenzenesulfonyl chloride, 4-nitrobenzenesulfonyl chloride, or 2,4-dinitrobenzenesulfonyl chloride, and a tertiary amine base such as 2,4,6-collidine, or 2,6-lutidine, in an inert organic solvent such as methylene chloride. The product of this reaction is the sulfonamide of type 32, which can be further modified by reaction with an alcohol of type 33 in the presence of triphenylphosphine and an activating agent such as DEAD, DIAD, or the like. The reaction is performed in a suitable inert organic solvent such as benzene, toluene, THF or mixtures thereof, typically at room temperature, and the reaction is generally complete in 0.5-3 h. The product of this reaction is the dialkylsulfonamide of type 34, which can be desulfonylated by treatment with either a nucleophilic amine like n-propylamine, in a solvent such as methylene chloride, or with mercaptoacetic acid and triethylamine in methylene chloride. In either case, the reaction is conducted typically at room temperature, for periods of 5 minutes to 1 hour. When a 2- or 4-nitrobenzenesulfonyl derivative is employed, the cleavage of the sulfonamide is accomplished with either the combination of thiophenol and potassium carbonate in a solvent like DMF, or with mercaptoacetic acid and lithium hydroxide in DMF. In either case, the reaction is conducted at room temperature, for periods of 1-3 h. The secondary amine product of structural formula 35 can be modified further using a variety of methods known in organic synthesis to provide other compounds of the present invention. For example, 35 may be Scheme M illustrates the preferred method for the resolution of a compound of structural formula 38 in which the bicyclic ring system does not have a plane of symmetry. Generally, the latter, or intermediates en route to their preparation, may be resolved to afford enantiomerically pure compounds such as 39 and 40 by chiral stationary phase liquid chromatography techniques or other suitable methods known in organic synthesis.

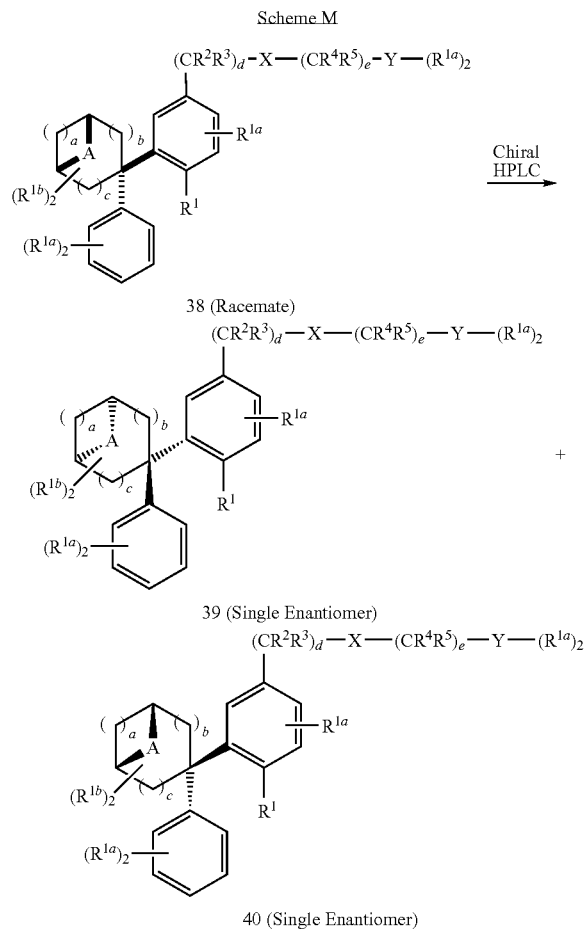

The following examples are provided to illustrate the invention and are not to be construed as limiting the scope of the invention in any manner.

Preparation of Intermediates:

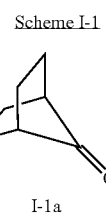

Bicyclo[2.2.1]heptan-7-one (I-1a) was prepared in accordance with Gassman, P. G. *J. Org. Chem.* 1964, 29, 160-163 and references cited therein.

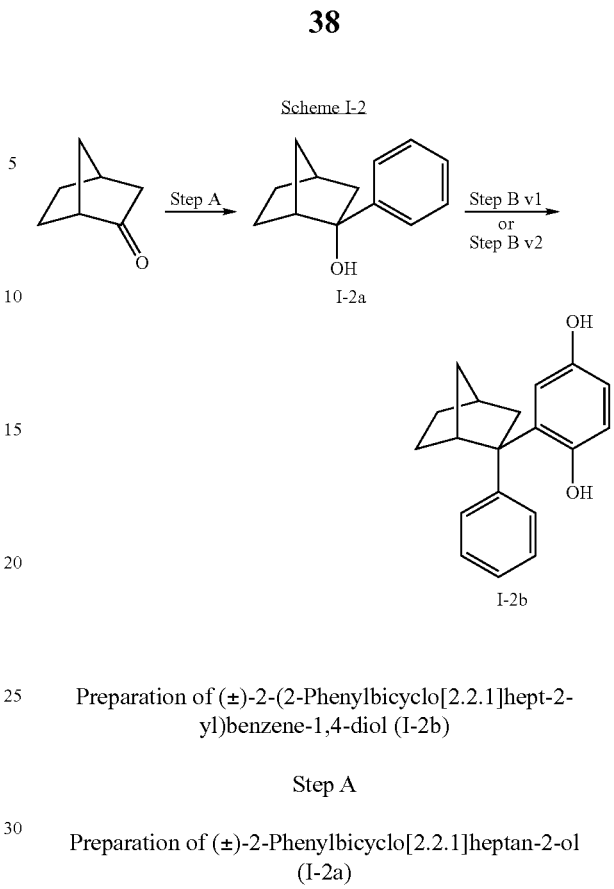

Preparation of (±)-2-(2-Phenylbicyclo[2.2.1]hept-2-yl)benzene-1,4-diol (I-2b)

Step A

Preparation of (±)-2-Phenylbicyclo[2.2.1]heptan-2-ol (I-2a)

To a solution of norcamphor (60.0 g, 0.54 mole) in THF (1 L) at −65° C. was added phenyl magnesium bromide (200 mL of a 3 M solution in ether, 0.60 mole). The temperature was kept between −65° C. and −20° C. during the addition. After completion of addition, the mixture was slowly warmed to room temperature and stirred overnight. The mixture was cooled to 0° C. and saturated aqueous ammonium chloride (200 mL) was added carefully. A solution of 1 N hydrochloric acid was added until the residual salts were dissolved. The mixture was then extracted twice with ether and the combined organic phases were washed successively with water and brine. The organic layer was dried ($MgSO_4$) and concentrated. Flash chromatography of the residue (silica gel; hexane/EtOAc 9:1) provided I-2a as a white solid (95.0 g).

Step B v1

Preparation of (±)-2-(2-Phenylbicyclo[2.2.1]hept-2-yl)benzene-1,4-diol (I-2b)

A solution of hydroquinone (100 g, 0.91 mole) and p-TSA monohydrate (9.00 g, 47.0 mmol) in toluene (1.5 L) was heated at reflux for 15 min with azeotropic removal of water using a Dean-Stark apparatus. A solution of I-2a (85.0 g, 0.45 mol) in toluene (100 mL) was added to the above solution using a dropping funnel and the resulting mixture was stirred at reflux for 3 h. After cooling to room temperature, the reaction mixture was diluted with EtOAc (1 L) and washed with water, brine, dried ($MgSO_4$) and evaporated. During the evaporation of the organic phase, the precipitated hydroquinone was removed by filtration. Flash chromatography of the residue (silica gel; hexane/EtOAc 3:1) provided I-2b as a pink solid (34.0 g), m.p. 179-181° C. Analysis for $C_{19}H_{20}O_2$, cal.: C, 81.40; H, 7.19; found: C, 81.07; H, 7.17.

Step B v2

Preparation of (±)-2-(2-Phenylbicyclo[2.2.1]hept-2-yl)benzene-1,4-diol (I-2b)

Aluminum (III) chloride (1 equiv.) was added to a prestirred solution of hydroquinone (2 equiv.) in dioxane at room temperature. A solution of I-2a in dioxane was then added over approximately 30 min via uniform motorized syringe addition. A second portion of aluminum (III) chloride (1 equiv.) was added and the resulting mixture stirred at room temperature for approximately 15 h. The reaction mixture was poured into a vigorously stirred mixture of ice/2 N HCl (1:1) and extracted three times with EtOAc. The combined organic extracts were washed with water, brine, dried ($Na_2SO_4$) and concentrated. The crude residue can be purified according to the method described above (Step B v1).

Following procedures similar to that described above for intermediate I-2b, the following additional intermediates can be prepared:

TABLE I-1

| Intermediate I-2 | A | b | $R^1$ | $R^2$ | $R^3$ | $R^4$ | Step B |
|---|---|---|---|---|---|---|---|
| c | $CH_2$ | 1 | H | H | Me | H | v2 |
| d | $CH_2$ | 1 | H | Me | H | H | v2 |
| e | $CH_2$ | 1 | H | H | F | H | v2 |
| f | $CH_2$ | 1 | H | H | Cl | H | v2 |
| g | $CH_2$ | 1 | H | Me | F | H | v2 |
| h | $CH_2CH_2$ | 0 | H | H | H | H | v1 |
| i | $CH_2$ | 1 | H | F | H | H | v2 |
| j | $CH_2$ | 1 | F | H | H | H | v2 |
| k | $CH_2$ | 1 | H | OMe | H | H | v2 |
| l | $CH_2$ | 1 | H | H | OMe | H | v1 |
| m | $CH_2$ | 1 | H | Cl | H | Cl | v2 |
| n | $CH_2$ | 1 | H | F | H | F | v2 |
| o | $CH_2$ | 1 | H | Me | H | Me | v2 |
| p | $CH_2$ | 1 | H | $CF_3$ | H | H | v2 |
| q | $CH_2$ | 1 | H | $OCFH_2$ | H | H | |
| r | $CH_2$ | 1 | H | $OCF_2H$ | H | H | |
| s | $CH_2$ | 1 | H | $OCH_2CH_3$ | H | H | |
| t | $CH_2$ | 1 | H | $OCH_2CFH_2$ | H | H | |
| u | $CH_2$ | 1 | H | O—▽ | H | H | |

Scheme I-3

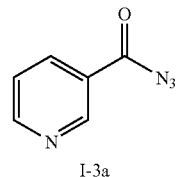

I-3a

Preparation of Nicotinyl azide (I-3a)

To a suspension of nicotinic acid (1.23 g, 10.0 mmol) in DMF (15 mL) was added diphenylphosphoryl azide (2.60 mL, 12.0 mmol) followed by triethylamine (1.67 mL, 12.0 mmol). The mixture was stirred at room temperature for 2.5 h and diluted with water (50 mL). The mixture was extracted three times with EtOAc and the combined organic extracts were washed three times with water, dried ($MgSO_4$) and concentrated. Flash chromatography of the residue (silica gel; hexane/EtOAc 7:3) provided I-3a as a white solid (1.13 g).

Preparation of Examples (The Compounds having Mass Spectral Data in Tables 1-9 were Synthetically Prepared):

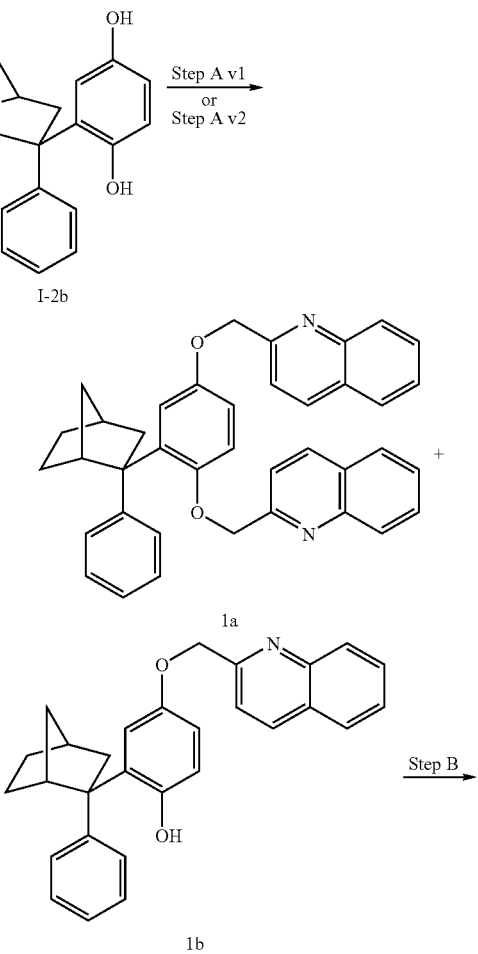

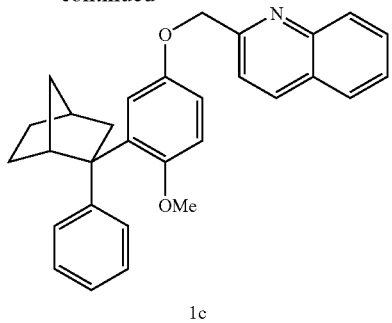

1c

EXAMPLES 1a, 1b AND 1c

Step A v1

Preparation of (±)-2-{[2-(2-Phenylbicyclo[2.2.1]hept-2-yl)-4-(quinolin-2-ylmethoxy)phenoxy]methyl}quinoline (1a) and (±)-2-(2-Phenylbicyclo[2.2.1]hept-2-yl)-4-(quinolin-2-ylmethoxy)phenol (1b)

At room temperature, potassium tert-butoxide (23.1 n-L of a 1 M solution in THF, 23.1 mmol) was added dropwise to a solution of I-2b (6.48 g, 23.1 mmol) in DMF (130 mL). During the course of the addition, the reaction mixture turned from heterogeneous to homogeneous. The resulting solution was aged at room temperature for 20 min. A solution of 2-(chloromethyl)quinoline (3.90 g, 22.0 mmol) in DMF (5 mL) was then added and the resulting mixture stirred at room temperature for 18 h. The reaction mixture was poured into water/1 N hydrochloric acid (300 mL:25 mL) at 0° C. and extracted three times with EtOAc. The combined organic extracts were washed three times with water, dried (MgSO$_4$) and concentrated. Flash chromatography of the residue (silica gel; hexane/EtOAc/triethylamine 48:1:1) provided in order of elution:

The bis-adduct 1a as a solid (2.20 g), m.p. 176-177° C., Analysis for $C_{39}H_{34}N_2O_2$, calc.: C, 83.25; H, 6.09; N, 4.98; found: C, 82.91; H, 6.07; N, 4.86.

The mono-adduct 1b as a solid (3.12 g), m.p. 221-224° C.

Step A v2

Preparation of (±)-2-(2-Phenylbicyclo[2.2.1]hept-2-yl)-4-(quinolin-2-ylmethoxy)phenol (1b)

Potassium iodide (6.92 g, 0.04 mol) and potassium carbonate (5.52 g, 0.04 mmol) were added successively to a stirred solution of I-2b (8.60 g, 0.03 mol) and 2-(chloromethyl)quinoline (7.41 g, 0.04 mol) in DMF (50 mL). After approximately 16 h, the reaction mixture was acidified to pH 6 with 1N hydrochloric acid. The precipitated solids were filtered to furnish the title compound 1b. The aqueous phase was extracted two times with EtOAc, and the combined organic extracts were washed with three times with water, brine, dried (MgSO$_4$) and concentrated in vacuo. Purification of the crude residue by flash chromatography on silica gel (gradient elution; 2-25% EtOAc/hexanes as eluent) furnished an additional amount of the title compound 1b.

Step B

Preparation of (±)-2-{[4-Methoxy-3-(2-phenylbicyclo[2.2.1]hept-2-yl)phenoxy]methyl}quinoline (1c)

To a solution of 1b (200 mg, 0.47 mmol) in DMF (4 mL) was added cesium carbonate (186 mg, 0.57 mmol) followed by methyl iodide (35.0 μL, 0.57 mmol). The mixture was stirred at room temperature for 18 h, diluted with water (20 mL) and extracted three times with EtOAc. The combined organic extracts were washed three times with water, dried (MgSO$_4$) and concentrated. The residue (210 mg) was triturated with a 1:1 mixture of hexane/ether to provide 1c as a solid (113 mg), m.p. 138-139° C.

Following procedures similar to that described above for Examples 1a-c, the following compounds were prepared:

TABLE 1

| Ex. #1 | R | Melting Point | Parent Ion m/z $(MH)^+$ |
|---|---|---|---|
| d | ⁓⁓⁓–Me | 138-139° C. | |
| e | ⁓⁓⁓–CN | 144-145° C. | |
| f | ⁓⁓⁓–N(Me)Me | 137-138° C. | |
| g | ⁓⁓⁓–CO$_2$Me | 158-159° C. | |
| h | ⁓⁓⁓–CO$_2$H | 191-193° C. | |
| i | ⁓⁓⁓–CO$_2$Me | 150-152° C. | |
| j | ⁓⁓⁓–CO$_2$H | 118-121° C. | |

TABLE 1-continued
| Ex. #1 | R | Melting Point | Parent Ion m/z (MH)+ |
|---|---|---|---|
| k | benzyl | 160-161° C. | |
| l | (pyridin-2-yl)methyl | 145-146° C. | |
| m | (pyridin-3-yl)methyl | 149-150° C. | |
| n | (pyridin-4-yl)methyl | 157-158° C. | |
| o | 2-phenylethyl | | 526 |
| p | 2-(pyridin-2-yl)ethyl | | 527 |
| q | 2-(pyridin-3-yl)ethyl | | 527 |
| r | -(CH2)3-NMe2 | | 507 |
| s | -(CH2)3-pyrrolidin-1-yl | | 519 |
TABLE 1-continued
| Ex. #1 | R | Melting Point | Parent Ion m/z (MH)+ |
|---|---|---|---|
| t | -(CH2)2-(2-oxopyrrolidin-1-yl) | | 533 |
| u | -(CH2)3-(2-oxopyrrolidin-1-yl) | | 547 |
| v | -(CH2)2-S(O)2-phenyl | | 590 |
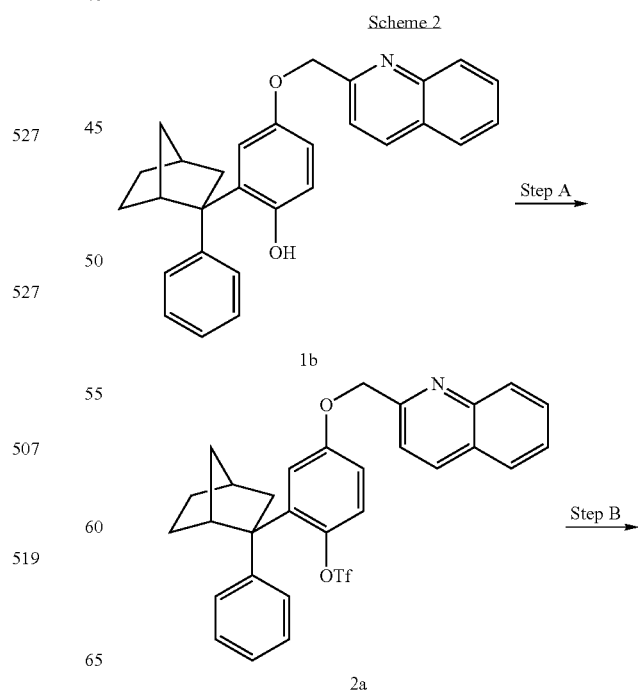
Scheme 2

-continued

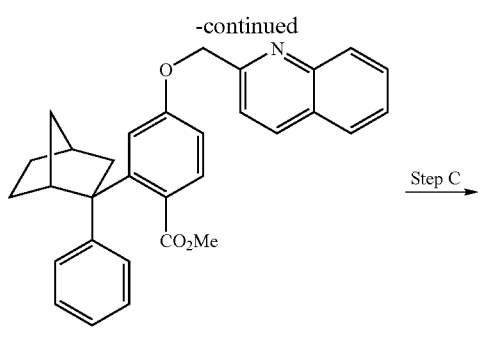

2b

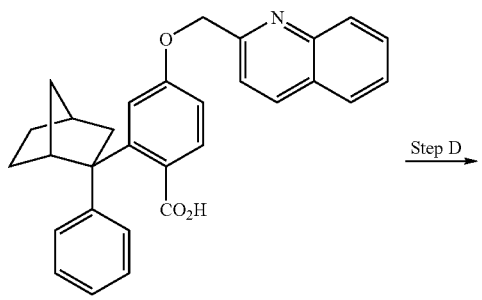

2c

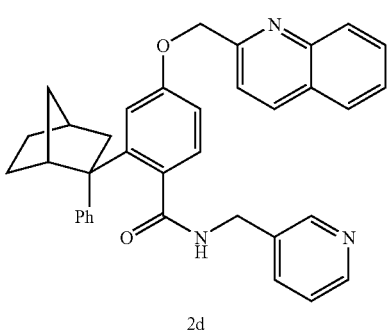

2d

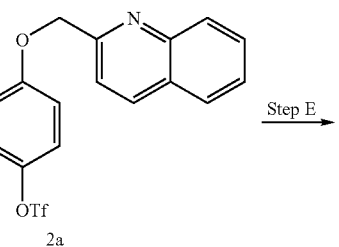

2a also,

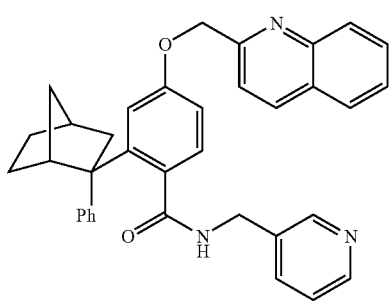

2d

Step C →

Step D →

Step E →

EXAMPLES 2a, 2b, 2c AND 2d

Step A

Preparation of (±)-2-(2-Phenylbicyclo[2.2.1]hept-2-yl)-4-(quinolin-2-ylmethoxy)phenyl trifluoromethanesulfonate (2a)

A solution of 1b (500 mg, 1.19 mmol) in pyridine (5 mL) was diluted with toluene (5 mL) and cooled to 0° C. To this mixture was added dropwise trifluoromethanesulfonic anhydride (0.20 mL, 1.19 mmol). The resulting mixture was stirred at room temperature for 18 h. A second portion of trifluoromethanesulfonic anhydride (0.06 mL, 0.36 mmol) was added and after approximately 4 h, the reaction mixture was diluted with water and extracted three times with EtOAc. The combined organic extracts were washed with water, dried (MgSO$_4$) and concentrated. Flash chromatography of the residue (silica gel; hexane/EtOAc 9:1) gave a solid (533 mg) that was triturated with hexane to provide 2a as a solid (402 mg), m.p. 131-132° C.

Step B

Preparation of (±)-Methyl 2-(2-phenylbicyclo[2.2.1]hept-2-yl)-4-(quinolin-2-ylmethoxy)benzoate (2b)

To a solution of 2a (280 mg, 0.50 mmol) in DMF (4.8 mL) and methanol (4.8 mL) were added successively palladium (II) acetate (12.0 mg, 0.05 mmol), dppf (54.0 mg, 0.10 mmol) and triethylamine (0.15 mL, 1.10 mmol). The reaction mixture was saturated with carbon monoxide and then heated to 80° C. under a carbon monoxide atmosphere (balloon) for 18 h. After cooling to room temperature, the reaction mixture was poured into water (20 mL) and extracted three times with EtOAc. The combined organic extracts were washed three times with water, dried (MgSO$_4$) and concentrated. Flash chromatography of the residue (silica gel; hexane/EtOAc 9:1) give a solid (122 mg) that was triturated with ether/hexane to provide 2b as a solid (62 mg), m.p. 106-107° C.

Step C

Preparation of (±)-2-(2-Phenylbicyclo[2.2.1]hept-2-yl)-4-(quinolin-2-ylmethoxy)benzoic acid (2c)

To a solution of 2b (67.0 mg, 0.14 mmol) in THF (3 mL) and 1,2-propanediol (3 mL) was added aqueous potassium hydroxide (0.40 mL of a 8 M solution in water, 3.20 mmol). The mixture was stirred at 110° C. for 18 h and then cooled to room temperature. The reaction mixture was diluted with water, acidified with 1 N hydrochloric acid and extracted three times with EtOAc. The combined organic extracts were washed with water, dried (MgSO$_4$) and concentrated. Flash chromatography of the residue (silica gel; dichloromethane/methanol/concentrated aqueous ammonium hydroxide (85:15:1) gave a solid (48.0 mg) that was triturated with ether/hexane to provide 2c as a solid (38 mg), m.p. 205-210° C. (dec.).

$^1$HNMR (300 MHz, acetone-d$_6$): δ 0.80-0.90 (m, 1H), 1.15-1.50 (m, 4H), 1.70 (d, 1H), 1.90-2.00 (m, 1H), 2.25 (br s, 1H), 2.75 (dd, 1H), 2.90 (br s, 1H), 5.55 (s, 2H), 6.95 (dd, 1H), 7.00-7.15 (m, 5H), 7.60-7.65 (m, 3H), 7.75-7.85 (m, 2H), 8.00 (d, 1H), 8.08 (d, 1H), 8.40 (d, 1H).

Step D

Preparation of (±)-2-(2-Phenylbicyclo[2.2.1]hept-2-yl)-N-(pyridin-3-ylmethyl)-4-(quinolin-2-yl-methoxy)benzamide (2d)

DIPEA (3.0 equiv.) is added to a stirred solution of 2c (1.0 equiv.), 3-(aminomethyl)pyridine (1.0 equiv.) and HATU (1.5 equiv.) in DMF at ambient temperature. After completion of reaction, the reaction mixture is poured into water and extracted three times with EtOAc. The combined organic extracts are washed with water, brine, dried (Na$_2$SO$_4$) and concentrated in vacuo. The crude residue can be purified according to the method described in Step E.

Step E

Preparation of (±)-2-(2-Phenylbicyclo[2.2.1]hept-2-yl)-N-(pyridin-3-ylmethyl)-4-(quinolin-2-yl-methoxy)benzamide (2d)

To a solution of 2a (200 mg, 0.38 mmol) in DMF (3.4 mL) were added successively palladium (II) acetate (8.40 mg, 0.04 mmol), dppf (42.0 mg, 0.08 mmol) and 3-(aminomethyl)pyridine (0.15 mL, 1.50 mmol). The reaction mixture was saturated with carbon monoxide and then heated to 80° C. under a carbon monoxide atmosphere (balloon) for 18 h. After cooling to room temperature, the reaction mixture was poured into water (20 mL) and extracted three times with EtOAc. The combined organic extracts were washed three times with water, dried (MgSO$_4$) and concentrated. Flash chromatography of the residue (silica gel; EtOAc) gave a solid (23.0 mg) that was triturated with ether to provide 2d as a solid (15.0 mg), m.p. 179-181° C.

Following procedures similar to that described above for Examples 2a-d, the following compounds can be prepared:

TABLE 2

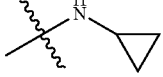

| Ex. #2 | R | Parent Ion m/z (MH)$^+$ |
|---|---|---|
| e | 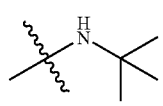 | 489 |
| f | 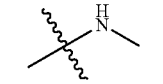 | 505 |
| g | 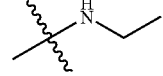 | 463 |

TABLE 2-continued

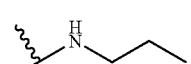

| Ex. #2 | R | Parent Ion m/z (MH)$^+$ |
|---|---|---|
| h | 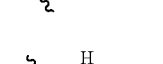 | 477 |
| i |  | 491 |
| j | 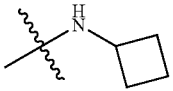 | 491 |
| k |  | 503 |
| l | 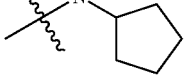 | 517 |
| m | 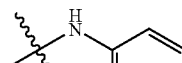 | 525 |
| n |  | 539 |
| o | 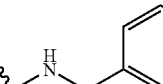 | 487 |
| p | | 526 |
| q | | 526 |

TABLE 2-continued
[Structure: norbornyl-phenyl-substituted benzene with O-CH2-quinoline group and C(=O)R group, Ph substituent]
| Ex. #2 | R | Parent Ion m/z (MH)+ |
|---|---|---|
| r | -NH-(4-pyridyl) | 526 |
| s | -NH-CH2-(2-pyridyl) | 540 |
| t | -N(CH3)2 | 477 |
| u | -N(Et)2 | 505 |
| v | -N(CH3)(Et) | 491 |
| w | -N(CH3)(iPr) | 505 |
| x | -N-pyrrolidinyl | 503 |
| y | -N-piperidinyl | 517 |
| z | -N-morpholinyl | — |
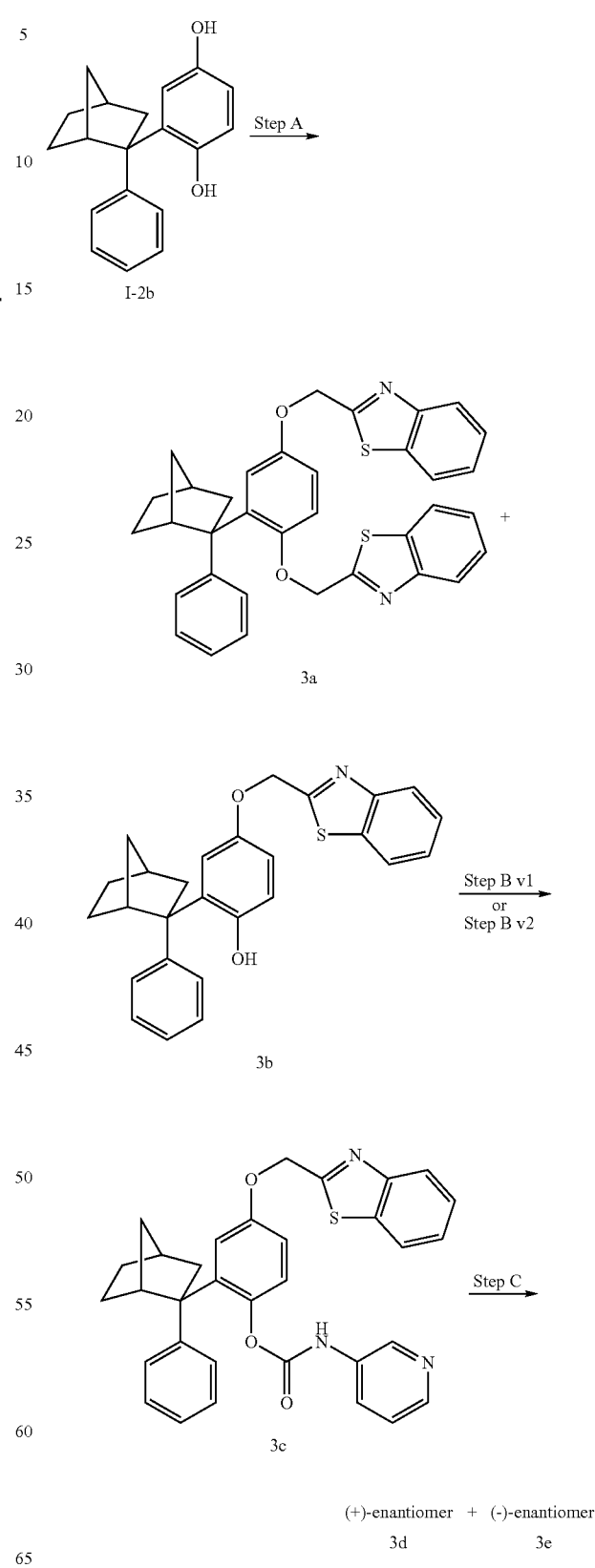
Scheme 3

EXAMPLES 3a, 3b, 3c, 3d AND 3e

Step A

Preparation of (±)-2-{[4-(1,3-Benzothiazolyl-2-yl-methoxy)-2-(2-phenylbicyclo[2.2.1]hept-2-yl)phenoxy]methyl}-1,3-benzothiazole (3a) (±)-4-(1,3-Benzothiazol-2-ylmethoxy)-2-(2-phenylbicyclo[2.2.1]hept-2-yl)phenol (3b)

At room temperature, potassium tert-butoxide (5.00 mL of a 1.0 M solution in THF, 5.00 mmol) was added dropwise to a solution of I-2b (1.40 g, 5.00 mmol) in DMF (30 mL). During the course of the addition, the reaction mixture turned from heterogeneous to homogeneous. After 25 min a solution of 2-(chloromethyl)-1,3-benzothiazole [(920 mg, 5.00 mmol), prepared in accordance with Mylari, B. L. et al. *Synth. Commun.* 1989, 19, 2921-24] in DMF (2 mL) was added and the resulting mixture stirred at room temperature for 18 h. The reaction mixture was poured into 25% aqueous ammonium acetate (100 mL) and extracted three times with EtOAc. The combined organic extracts were washed three times with water, dried (MgSO$_4$) and concentrated. Flash chromatography of the residue (silica gel; toluene/EtOAc 19:1) provided the bis-adduct 3a as a beige solid (280 mg), m.p. 165-167° C. Analysis for C$_{35}$H$_{30}$N$_2$O$_2$S, calc.: C, 77.46; H, 5.57; N, 5.16; found: C, 77.59; H, 5.70; N, 5.40.

Further elution with hexane/EtOAc/triethylamine (70:30:4) provided the mono-adduct 3b as a foam (503 mg).

$^1$HNMR (500 MHz, acetone-d$_6$): δ 0.90-1.00 (m, 1H), 1.20-1.28 (m, 1H), 1.28-1.40 (m 2H), 1.40-1.52 (m, 1H), 1.72 (d, 1H), 1.98-2.05 (m, 1H), 2.30 (br s, 1H), 2.60 (dd, 1H), 3.10 (d, 1H), 3.80 (br s, 1H), 5.55 (s, 2H), 6.60 (d, 1H), 6.75 (dd, 1H), 7.05 (t, 1H), 7.05-7.15 (m, 2H), 7.15-7.60 (m, 2H), 7.40 (s, 1H), 7.48 (t, 1H), 7.55 (t, 1H), 8.05 (d, 1H), 8.10 (d, 1H).

Step B v1

Preparation of (±)-4-(1,3-Benzothiazol-2-yl-methoxy)-2-(2-phenylbicyclo[2.2.1]hept-2-yl)phenyl pyridin-3-ylcarbamate (3c)

A solution of nicotinyl azide (89.0 mg, 0.60 mmol) in toluene (3 mL) was heated at reflux for 30 min to form the corresponding isocyanate derivative in situ. To this solution was added solid 3b (170 mg, 0.40 mmol) followed by DIPEA (104 μL, 0.60 mmol). The resulting mixture was refluxed for 3 h, cooled to room temperature and evaporated. Flash chromatography of the residue (silica gel; EtOAc/acetic acid 1:0 to 39:1) provided 3c as a foam (138 mg). Analysis for C$_{33}$H$_{29}$N$_3$O$_3$S, calc.: C, 72.37; H, 5.34; N, 7.67; found: C, 71.98; H, 5.45; N, 7.79

$^1$HNMR (500 MHz, acetone-d$_6$): δ 0.80-0.90 (m, 1H), 1.20-1.40 (m, 2H), 1.40-1.52 (m, 2H), 1.75 (d, 1H), 1.88 (dt, 1H), 2.32 (br s, 1H), 2.75 (d, 1H), 3.05 (br s, 1H), 5.68 (s, 2H), 6.95-7.08 (m, 6H), 7.22-7.30 (m, 2H), 7.50 (t, 1H), 7.55-7.60 (m, 2H), 7.80 (d, 1H), 8.05 (d, 1H), 8.12 (d, 1H), 8.25 (d, 1H), 8.60 (s, 1H), 8.95 (br s, 1H).

Step B v2

Preparation of (±)-4-(1,3-Benzothiazol-2-yl-methoxy)-2-(2-phenylbicyclo[2.2.1]hept-2-yl)phenyl pyridin-3-ylcarbamate (3c)

Triphosgene (0.4 equiv.), followed by pyridine (1.5 equiv.) were added sequentially to a stirred solution of 3b in methylene chloride at approximately 0° C. After approximately 45 min, 3-aminopyridine (4 equiv.) was added followed by triethylamine (5 equiv.). After approximately 15 min, the reaction mixture was warmed to room temperature and stirred for 2 h. The reaction was quenched with saturated aqueous ammonium chloride, poured into water and extracted three times with EtOAc. The combined organic extracts were washed with brine, dried (Na$_2$SO$_4$) and concentrated in vacuo. The crude residue can be purified according to the method described above (Step B v1).

Step C

Preparation of (+) 4-(1,3-Benzothiazol-2-ylmethoxy)-2-(2-phenylbicyclo[2.2.1]hept-2-yl)phenyl pyridin-3-ylcarbamate (3d) and (−) 4-(1,3-Benzothiazol-2-ylmethoxy)-2-(2-phenylbicyclo[2.2.1]hept-2-yl) phenyl pyridin-3-ylcarbamate (3e)

Enantiomers 3d and 3e were prepared by the following resolution procedure. A solution of 3c (90.0 mg) in hexane/2-propanol (16 mL, 4:1) was injected (2×8 mL) onto a Chiralpak® (available from Chiral Technologies, Inc., Exton, Pa.) semi-preparative (250×20 mm) HPLC column (eluting with hexane/2-propanol 4:1 at 10 mL/min with UV detection at 270 nm). The enantiomers were separated with the faster eluting enantiomer 3d having a retention time of ~33 min and the slower eluting enantiomer 3e having a retention time of ~45 min. The eluants were concentrated to provide the enantiomers 3d (foam, 28.0 mg, α$_D$+139.6° (c=1, chloroform)) and 3e (foam, 29.0 mg, α$_D$−137.2°(c=1, chloroform)).

Following procedures similar to that described above for Examples 3a-e, the following compounds can be prepared as either single enantiomers or racemic mixtures:

TABLE 3

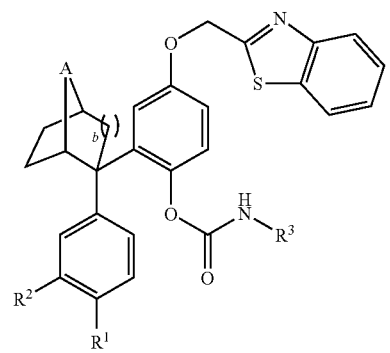

| Ex. #3 | A | b | R$^1$ | R$^2$ | R$^3$ | Parent Ion m/z (M + 1) | Step B |
|---|---|---|---|---|---|---|---|
| f | CH$_2$ | 1 | Me | H | 3-pyridyl | 562 | v2 |
| g | CH$_2$ | 1 | H | Me | 3-pyridyl | 562 | v2 |
| h | CH$_2$ | 1 | F | H | 3-pyridyl | 566 | v2 |
| i | CH$_2$ | 1 | Cl | H | 3-pyridyl | 582 | v2 |
| j | CH$_2$ | 1 | F | Me | 3-pyridyl | 580 | v1 |
| k | CH$_2$ | 1 | H | H | Me | 485 | v2 |
| l | CH$_2$ | 1 | H | H | Et | 499 | v2 |
| m | CH$_2$ | 1 | H | H | i-Pr | 513 | v2 |
| n | CH$_2$ | 1 | H | H | cyclopropyl | 511 | v2 |
| o | CH$_2$ | 1 | Cl | H | cyclopropyl | 545 | v2 |
| p | CH$_2$ | 1 | F | Me | cyclopropyl | 543 | v2 |
| q | CH$_2$ | 1 | H | H | Ph | 547 | v2 |
| r*** | CH$_2$CH$_2$ | 0 | H | H | 3-pyridyl | 548 | v2 |

***Compound is achiral

Scheme 4
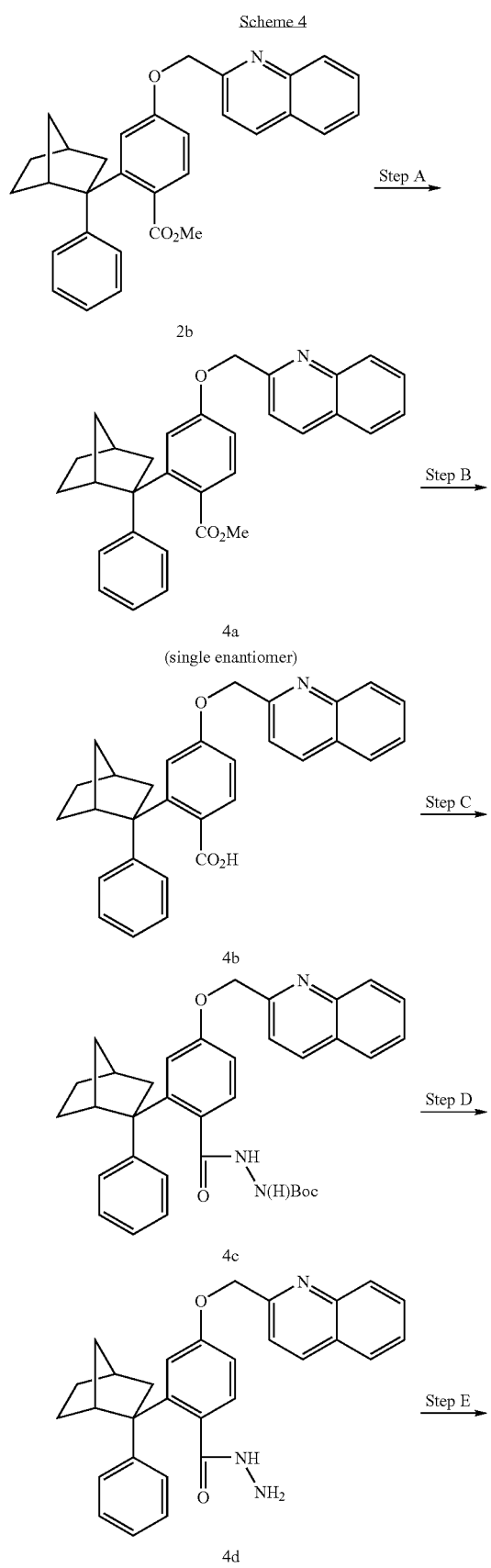
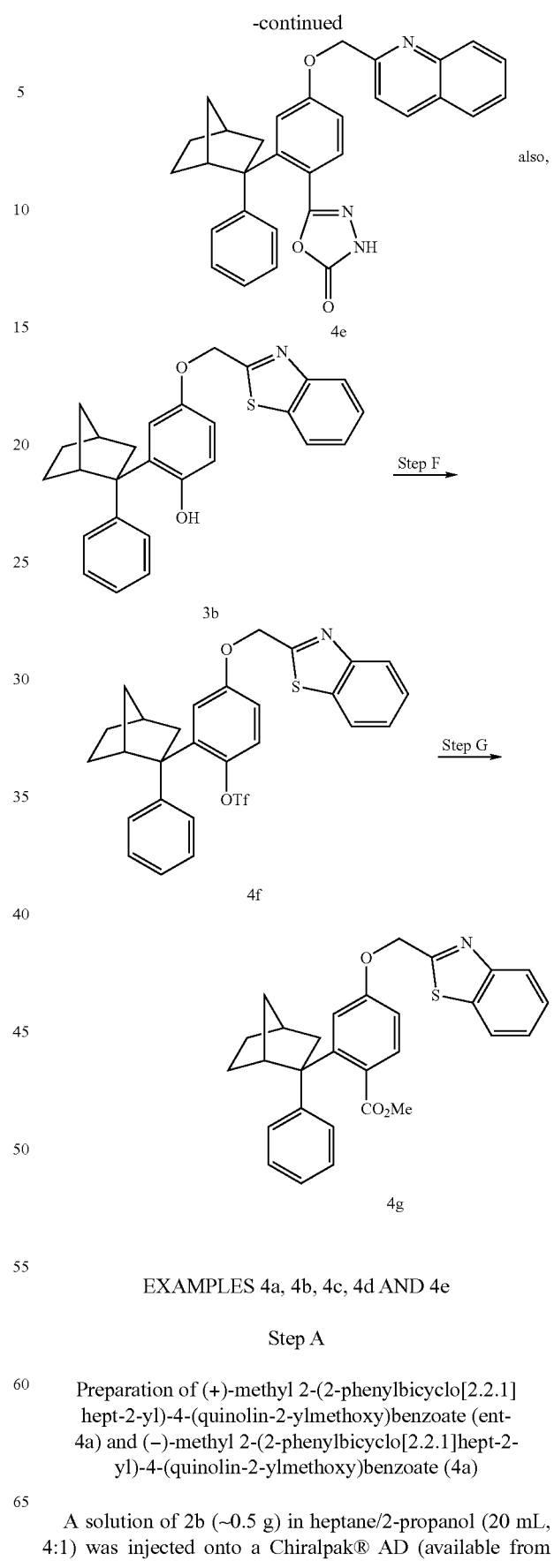
EXAMPLES 4a, 4b, 4c, 4d AND 4e
Step A
Preparation of (+)-methyl 2-(2-phenylbicyclo[2.2.1]hept-2-yl)-4-(quinolin-2-ylmethoxy)benzoate (ent-4a) and (−)-methyl 2-(2-phenylbicyclo[2.2.1]hept-2-yl)-4-(quinolin-2-ylmethoxy)benzoate (4a)
A solution of 2b (~0.5 g) in heptane/2-propanol (20 mL, 4:1) was injected onto a Chiralpak® AD (available from Chiral Technologies, Inc., Exton, Pa.) preparative HPLC column (250×100 mm, 20% 2-propanol/iso-octane as eluent at 250 mL/min, 300 nm UV detection). The enantiomers were separated with the faster eluting enantiomer 4a having a retention time of 11.26 min and the slower eluting enantiomer having a retention time of 14.75 min. The separated fractions were concentrated to provide the faster eluting enantiomer 4a (foam, (−) CD deflection) and the slower eluting enantiomer ent-4a (foam, (+) CD deflection).

Step B

Preparation of (−)-2-(2-phenylbicyclo[2.2.1]hept-2-yl)-4-(quinolin-2-ylmethoxy)benzoic acid (4b)

Aqueous potassium hydroxide (10.5 mL of an 8 M solution in water, 84.3 mmol) was added to a stirred solution of 4a (1.70 g, 3.67 mmol) in THF (30 mL) and 1,2-propanediol (30 mL). The mixture was heated to 110° C. for 18 h and then cooled to room temperature. The reaction mixture was diluted with water, acidified to pH 6 with 1 N hydrochloric acid and extracted three times with EtOAc. The combined organic extracts were washed with water, brine, dried ($Na_2SO_4$) and concentrated in vacuo to give 4b which was used without purification in the subsequent reaction.

Step C

Preparation of (−)-tert-butyl-2-[2-(2-phenylbicyclo [2.2.1]hept-2-yl)-4-(quinolin-2-ylmethoxy)benzoyl] hydrazinecarboxylate (4c)

DIPEA (1.53 mL, 8.78 mmol.) was added to a stirred solution of 4b (1.76 mmol), t-butyl carbazate (1.16 g, 8.78 mmol) and HATU (1.34 g, 3.52 mmol) in DMF (20 mL) at ambient temperature. After approximately 18 h, the reaction mixture was poured into saturated aqueous sodium bicarbonate and extracted three times with EtOAc. The combined organic extracts were washed with water, brine, dried ($Na_2SO_4$) and concentrated in vacuo. Purification of the crude residue by flash chromatography on silica gel (gradient elution; 0-35% EtOAc/hexanes as eluent) furnished the title compound 4c, m/z (ES) 564 $(MH)^+$.

Step D

Preparation of (−)-2-(2-phenylbicyclo[2.2.1]hept-2-yl)-4-(quinolin-2-ylmethoxy)benzohydrazide (4d)

Cold hydrogen chloride/EtOAc (10 mL; saturated solution) was added to a stirred solution of 4c (0.99 g, 1.76 mmol) in methylene chloride (5 mL) at room temperature. After approximately 1 h, the reaction mixture was concentrated in vacuo and the crude residue partitioned between saturated aqueous sodium bicarbonate and methylene chloride. The organic phase was separated, and the aqueous phase was re-extracted twice with methylene chloride. The combined organic extracts were washed with brine, dried ($Na_2SO_4$) and concentrated in vacuo to afford 4d as a white powder (m/z (ES) 464 $(MH)^+$) which was used without further purification in the subsequent reaction.

Step E

Preparation of (−)-5-[2-(2-phenylbicyclo[2.2.1]hept-2-yl)-4-(quinolin-2-ylmethoxy)phenyl]-1,3,4-oxadiazol-2(3H)-one (4e)

Phosgene (751 μL of a ~20% w/v solution in toluene, 1.42 mmol) was added dropwise via syringe to a stirred solution of 4d (365 mg, 0.79 mmol) in methylene chloride (20 mL) at −78° C. After approximately 45 minutes, the reaction mixture was poured into saturated aqueous sodium bicarbonate and extracted three times with methylene chloride. The combined organic extracts were washed with brine, dried ($Na_2SO_4$) and concentrated in vacuo. The crude residue was purified by preparative reversed phase HPLC on YMC Pack Pro C18 stationary phase (gradient elution; 0-75% acetonitrile/water as eluent, 0.1% TFA as modifier). Lyophilization of the purified fractions afforded the title compound 4e, m/z (ES) 490 $(MH)^+$.

Step F

Preparation of 4-(1,3-benzothiazol-2-ylmethoxy)-2-(2-phenylbicyclo[2.2.1]hept-2-yl)phenyltrifluoromethanesulfonate (4f)

Performed as described for Example 2a (Step A, Scheme 2)

Step G

Preparation of (±)-Methyl 4-(1,3-benzothiazol-2-ylmethoxy)-2-(2-phenylbicyclo[2.2.1]hept-2-yl)benzoate (4g)

trans-Di-μ-acetatobis[2-(di-o-tolylphosphino)benzyl]dipalladium(II) (328 mg, 0.35 mmol) and rac-2,2'-bis(diphenylphosphino)-1,1'-binaphthyl (500 mg, 0.80 mmol) were added to a stirred solution of 4f in DMF (3.5 mL), which had been degassed by the passage of a gentle stream of argon for 15 min. The mixture was evacuated and purged with argon three times. Methanol (3.5 mL) and triethylamine (0.24 mL, 1.80 mmol) were added and the resulting mixture was evacuated and purged with carbon monoxide three times. After stirring at room temperature for 30 min, the reaction mixture was heated to 80-85° C. After 16 h, the reaction mixture was cooled to room temperature, poured into water (5 mL) and extracted three times with EtOAc. The combined organic extracts were washed with water, brine, dried ($MgSO_4$) and concentrated in vacuo. Purification of the crude residue by flash chromatography on silica gel (gradient elution, 0-6% EtOAc/hexanes as eluent) gave the title compound 4g as a white foam. $R_f$: 0.30 (4:1 hexane:EtOAc). m/z (ES) 470 $(MH)^+$.

Following procedures similar to that described above for Examples 4a-g the following compounds can be prepared as either single enantiomers or racemic mixtures:

TABLE 4

| Ex. #4 | A | b | R¹ | R² | R³ | R⁴ | Parent Ion m/z (MH)⁺ |
|---|---|---|---|---|---|---|---|
| h* | CH₂ | 1 | H | H | benzothiazol-2-yl | −CH(CH₃)C(O)OH | 456 |
| i* | CH₂ | 1 | H | H | benzothiazol-2-yl | −CH(CH₃)C(O)NHNH₂ | 470 |
| j* | CH₂ | 1 | H | H | benzothiazol-2-yl | 5-(2-oxo-2,3-dihydro-1,3,4-oxadiazolyl) | 496 |
| k** | CH₂ | 1 | H | OMe | quinolin-2-yl | 5-(2-oxo-2,3-dihydro-1,3,4-oxadiazolyl) | 520 |
| aa*** | CH₂CH₂ | 0 | H | H | quinolin-2-yl | 5-(2-oxo-2,3-dihydro-1,3,4-oxadiazolyl) | |
| ab*** | CH₂CH₂ | 0 | H | H | benzothiazol-2-yl | 5-(2-oxo-2,3-dihydro-1,3,4-oxadiazolyl) | |

*Prepared as racemic mixture;
**Prepared as single enantiomer;
***Compound is achiral

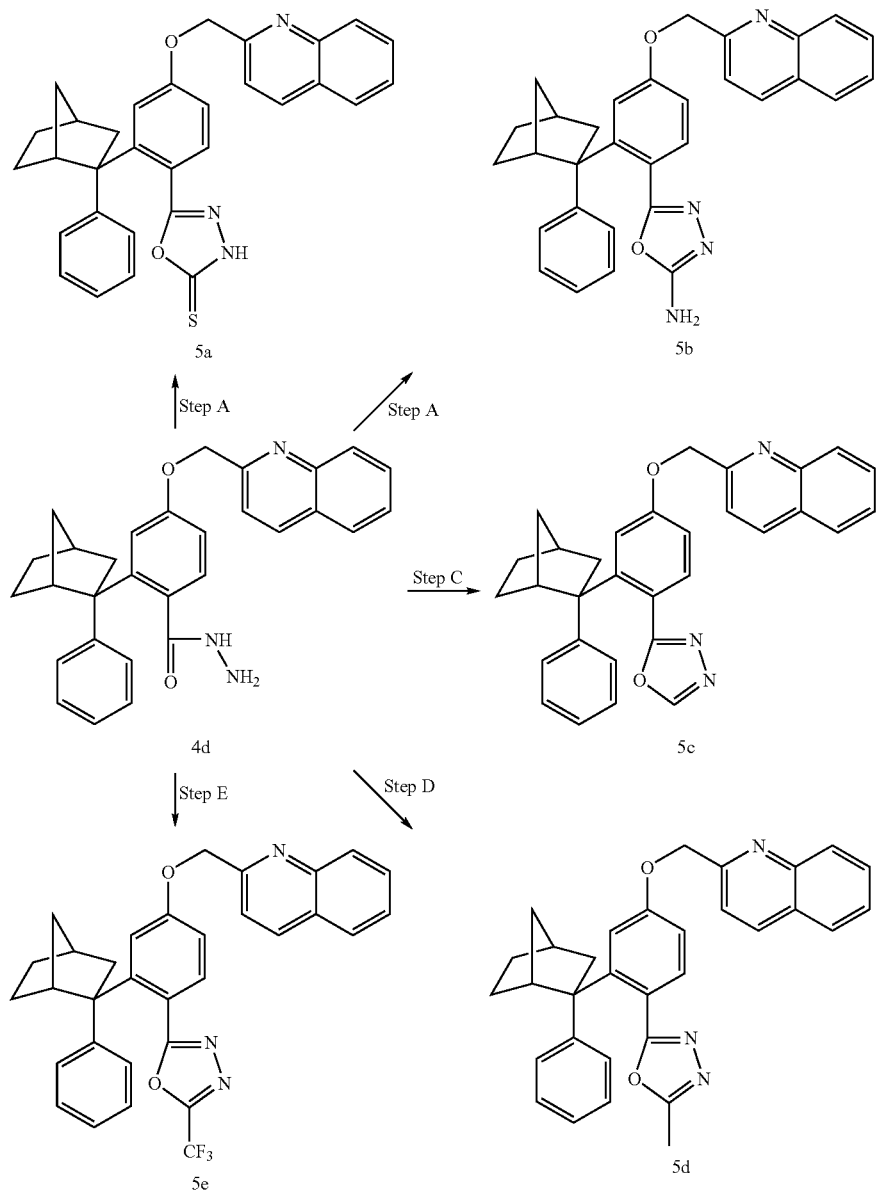

Scheme 5

EXAMPLES 5a, 5b, 5c, 5d AND 5e

Step A

Preparation of 5-[2-(2-phenylbicyclo[2.2.1]hept-2-yl)-4-(quinolin-2-ylmethoxy)phenyl]-1,3,4-oxadiazole-2(3H)-thione (5a)

Thiophosgene (10.0 µL, 0.13 mmol) was added to a stirred solution of 4d (0.11 mmol) in THF (900 µL) at −78° C. After approximately 45 min, the reaction mixture was poured into saturated aqueous sodium bicarbonate and extracted three times with methylene chloride. The combined organic extracts were washed with brine, dried (Na$_2$SO$_4$) and concentrated in vacuo. The crude residue was purified by preparative reversed phase HPLC on YMC Pack Pro C18 stationary phase (gradient elution; 0-75% acetonitrile/water as eluent, 0.1% TPA as modifier). Lyophilization of the purified fractions afforded the title compound 5a, m/z (ES) 506 (MH)$^+$.

Step B

Preparation of 5-[2-(2-phenylbicyclo[2.2.1]hept-2-yl)-4-(quinolin-2-ylmethoxy)phenyl]-1,3,4-oxadiazol-2-amine (5b)

A solution of sodium bicarbonate (10.0 mg, 0.12 mmol) in water (267 µL) was added dropwise via syringe to a stirred solution of 4d (0.108 mmol) in dioxane (1.0 mL) at room temperature. A suspension of cyanogen bromide (13.0 mg, 0.12 mmol) in dioxane (120 µL) was added in 4 equal portions at 1 minute intervals. After approximately 45 min, the reaction mixture was poured into saturated aqueous sodium bicarbonate and extracted three times with methylene chloride.

The combined organic extracts were washed with brine, dried (Na$_2$SO$_4$) and concentrated in vacuo. The crude residue was purified by preparative reversed phase HPLC on YMC Pack Pro C18 stationary phase (gradient elution; 0-75% acetonitrile/water as eluent, 0.1% TiFA as modifier). Lyophilization of the purified fractions afforded the title compound 5b, m/z (ES) 489 (MH)$^+$.

Step C

Preparation of 2-{[4-(1,3,4-oxadiazol-2-yl)-3-(2-phenylbicyclo[2.2.1]hept-2-yl)phenoxy]methyl}quinoline (5c)

A catalytic amount of p-TSA (~3 mg) was added to a stirred suspension of 4d HCl salt (54.6 mg, 0.10 mmol) in triethylorthoformate (600 µL) at room temperature. After 30 min, 1N hydrochloric acid (600 µL) was added, and the resulting solution was aged for an additional 45 min. The reaction mixture was poured into saturated aqueous sodium bicarbonate and extracted three times with EtOAc. The combined organic extracts were washed with brine, dried (Na$_2$SO$_4$) and concentrated in vacuo. The crude residue was purified by preparative reversed phase HPLC on YMC Pack Pro C18 stationary phase (gradient elution; 0-75% acetonitrile/water as eluent, 0.1% TFA as modifier). Lyophilization of the purified fractions afforded the title compound Sc, m/z (ES) 474 (MH)$^+$.

Step D

Preparation of 2-{[4-(5-methyl-1,3,4-oxadiazol-2-yl)-3-(2-phenylbicyclo[2,2,1]hept-2-yl)phenoxy]methyl}quinoline (5d)

Acetyl chloride (10.0 µL, 0.14 mmol) was added to a stirred solution of 4d (50.0 mg, 0.11 mmol) and triethylamine (38.0 µL, 0.27 mmol) in THB (900 µL) at room temperature. After approximately 18 h, the reaction mixture was poured into saturated aqueous sodium bicarbonate and extracted three times with methylene chloride. The combined organic extracts were washed with brine, dried (Na$_2$SO$_4$) and concentrated in vacuo. The crude intermediary acylhydrazide was treated with thionyl chloride (~1 mL, excess), and the resulting mixture was aged for approximately 18 h. The reaction mixture was poured carefully into cold saturated aqueous sodium bicarbonate and extracted three times with methylene chloride. The combined organic extracts were washed with brine, dried (Na$_2$SO$_4$) and concentrated in vacuo. The crude residue was purified by preparative reversed phase HPLC on YMC Pack Pro C18 stationary phase (gradient elution; 20-100% acetonitrile/water as eluent, 0.1% TFA as modifier). Lyophilization of the purified fractions afforded the title compound 5d, m/z (ES) 488 (MH)$^+$.

Step E

Preparation of 2-({3-(2-phenylbicyclo[2.2.1]hept-2-yl)-4-[5-(trifluoromethyl)-1,3,4oxadiazol-2-yl]phenoxy}methyl)guinoline (5e)

Trifluoroacetic anhydride (22.0 µL, 0.16 mmol) was added to a stirred solution of 4d (50.0 mg, 0.11 mmol) and triethylamine (38.0 µL, 0.27 mmol) in methylene chloride (1.8 mL) at room temperature. After approximately 18 h, the reaction mixture was poured into saturated aqueous sodium bicarbonate and extracted three times with methylene chloride. The combined organic extracts were washed with brine, dried (Na$_2$SO$_4$) and concentrated in vacuo. The crude intermediary acylhydrazide was treated with thionyl chloride (~1.5 ml, excess) and the resulting mixture was aged for approximately 18 h. The reaction mixture was poured carefully into cold saturated aqueous sodium bicarbonate and extracted three times with EtOAc. The combined organic extracts were washed with water, brine, dried (Na$_2$SO$_4$) and concentrated in vacuo. Purification of the crude residue by flash chromatography on silica gel (gradient elution; 0-25% EtOAc/hexanes as eluent) furnished the title compound 5e, m/z (ES) 542 (MH)$^+$.

Following procedures similar to that described above for Examples 5a-e, the following compounds can be prepared as either single enantiomers or racemic mixtures:

TABLE 5

| Ex. #5 | A | b | R$^1$ | R$^2$ | R$^3$ | R$^4$ | Parent Ion m/z (MH)$^+$ |
|---|---|---|---|---|---|---|---|
| f* | CH$_2$ | 1 | H | H | 2-benzothiazolyl | 5-amino-1,3,4-oxadiazol-2-yl | 495 |

TABLE 5-continued
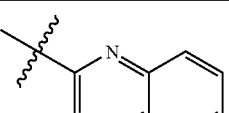
| Ex. #5 | A | b | R¹ | R² | R³ | R⁴ | Parent Ion m/z (MH)⁺ |
|---|---|---|---|---|---|---|---|
| g** | CH₂ | 1 | H | OMe | 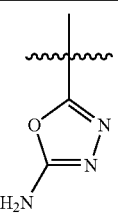 | 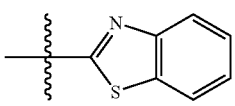 | 519 |
| h* | CH₂ | 1 | H | H | 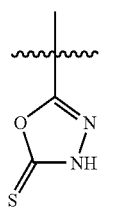 | 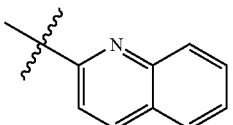 | 512 |
| i | CH₂ | 1 | H | OMe | 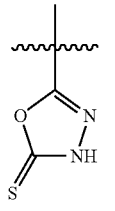 | 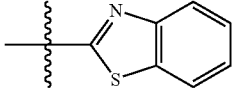 | |
| j | CH₂ | 1 | H | H | 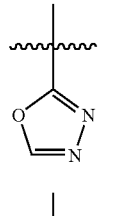 | 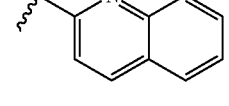 | |
| k | CH₂ | 1 | H | OMe | 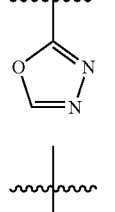 |  | |
| l | CH₂ | 1 | H | H | 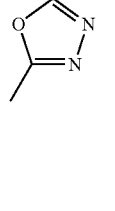 | | |

TABLE 5-continued
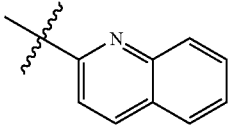
| Ex. #5 | A | b | R¹ | R² | R³ | R⁴ | Parent Ion m/z (MH)⁺ |
|---|---|---|---|---|---|---|---|
| m | CH₂ | 1 | H | OMe | 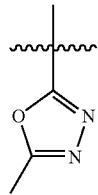 | 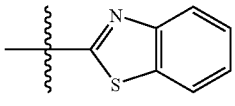 | |
| n | CH₂ | 1 | H | H | 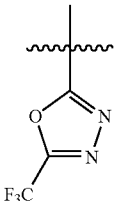 | 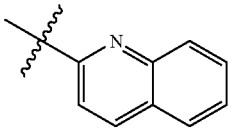 | |
| o | CH₂ | 1 | H | OMe | 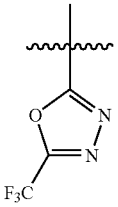 | 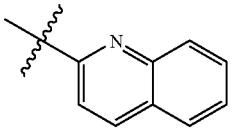 | |
| aa*** | CH₂CH₂ | 0 | H | H | 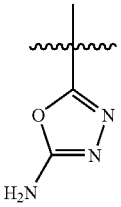 | | |

TABLE 5-continued

| Ex. #5 | A | b | R¹ | R² | R³ | R⁴ | Parent Ion m/z (MH)⁺ |
|---|---|---|---|---|---|---|---|
| ab*** | CH₂CH₂ | 0 | H | H | 2-quinolinyl | 5-thioxo-4H-1,3,4-oxadiazol-2-yl | |
| ac*** | CH₂CH₂ | 0 | H | H | 2-quinolinyl | 1,3,4-oxadiazol-2-yl | |
| ad*** | CH₂CH₂ | 0 | H | H | 2-quinolinyl | 5-methyl-1,3,4-oxadiazol-2-yl | |
| ae*** | CH₂CH₂ | 0 | H | H | 2-quinolinyl | 5-trifluoromethyl-1,3,4-oxadiazol-2-yl | |

*Prepared as racemic mixture;
**Prepared as single enantiomer;
***Compound is achiral

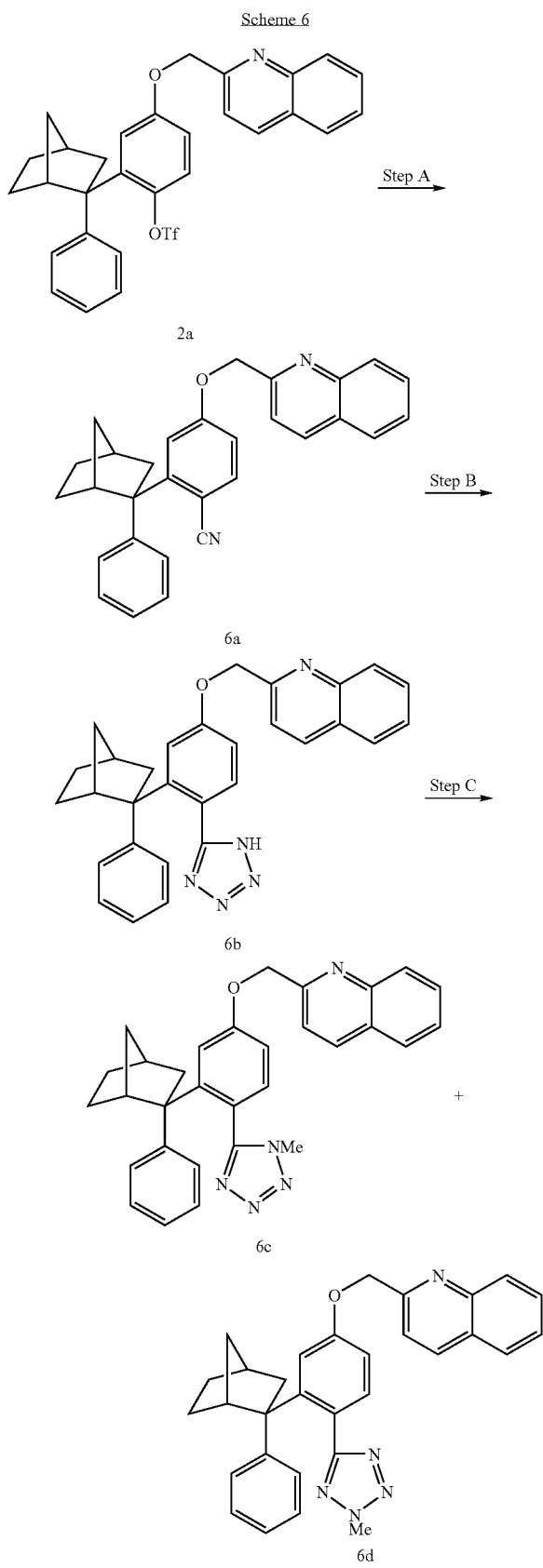

Scheme 6

EXAMPLES 6a, 6b, 6c AND 6d

Step A

Preparation of (±)-2-(2-phenylbicyclo[2.2.1]hept-2-yl)-4-(quinolin-2-ylmethoxy)benzonitrile (6a)

Zinc cyanide (155 mg, 1.32 mmol), tris(dibenzylideneacetone)dipalladium(0) (302 mg, 0.33 mmol), and dppf (457 mg, 0.83 mmol) were added successively to a stirred solution of 2a (913 mg, 1.65 mmol) in NMP (8.5 mL). After degassing the resulting mixture with a gentle stream of dry nitrogen for 90 min, the reaction mixture was heated to 140° C. After 20 h, the reaction mixture was cooled to room temperature, and filtered through a short column of silica gel eluting with EtOAc. The filtrate was washed twice with water, brine, dried (MgSO$_4$) and concentrated in vacuo. Purification of the crude residue by flash chromatography on silica gel (gradient elution; 0-20% EtOAc/hexanes as eluent) gave the title compound as a white foam. R$_f$: 0.35 (4:1 hexane:EtOAc). m/z (ES) 431 (MH)$^+$. $^1$H NMR (500 MHz, CDCl$_3$): δ 0.93-0.98 (m, 1H), 1.28-1.34 (m, 2H), 1.34-1.40 (m, 1H), 1.48-1.58 (m, 1H), 1.61 (br d, 1H), 2.06-2.14 (m, 1H), 2.44 (br t, 1H), 2.86 (dd, J=2.3, 13.3 Hz, 1H), 3.01 (br d, 1H), 5.53 (s, 2H), 6.85 (dd, J=2.3, 8.4 Hz, 1H), 7.12-7.18 (m, 2H), 7.18-7.30 (m, 3H), 7.45 (d, J=8.4 Hz, 1H), 7.53 (d, J=2.5 Hz, 1H), 7.63 (m, 1H), 7.72 (d, J=8.4 Hz, 1H), 7.81 (m, 1H), 7.90 (d, J=8.3 Hz, 1H), 8.16 (d, J=8.5 Hz, 1H), 8.29 (d, J=8.5 Hz, 1H).

Step B

Preparation of (±)-2-{[3-(2-phenylbicyclo[2.2.1]hept-2-yl)-4-(1H-tetrazol-5-yl)phenoxy]methyl}quinoline (6b)

Azidotrimethyltin (82.0 mg, 0.40 mmol) was added to a stirred solution of 6a (40.0 mg, 0.09 mmol) in toluene (0.6 mL) at room temperature and the resulting mixture heated to 140° C. After 72 h, the reaction mixture was cooled to room temperature, and the volatiles were removed in vacuo. The residue was taken up in cold hydrogen chloride/MeOH (1 mL; saturated solution) and stirred for 20 min at room temperature. The reaction mixture was concentrated in vacuo, and the crude residue was purified by flash chromatography on silica gel (gradient elution, 0-10% methanol/methylene chloride as eluent) to furnish the title compound as an off-white foam. R$_f$: 0.15 (1:2 hexane:EtOAc). m/z (ES) 474 (MH)$^+$. $^1$H NMR (500 M, CDCl$_3$): δ 0.89-0.93 (m, 1H), 1.19-1.26 (m, 1H), 1.26-1.40 (m, 2H), 1.46-1.55 (m, 1H), 1.72 (br d, 1H), 1.88 (td, J=2.8, 13.6 Hz, 1H), 2.03 (dd, J=2.3, 13.7 Hz, 1H), 2.34 (br s, 1H), 3.01 (br d, J=3.6 Hz, 1H), 5.55 (s, 2H), 6.94 (dd, J=2.3, 8.4 Hz, 1H), 7.0-7.22 (m, 3H), 7.22-7.32 (m, 3H), 7.62-7.68 (m, 2H), 7.78-7.86 (m, 2H), 7.90-7.96 (m, 1H), 8.20 (m, 1H), 8.37 (m, 1H).

Step C

Preparation of (±)-2-{[4-(2-methyl-1H-tetrazol-5-yl)-3-(2-phenylbicyclo[2.2.1]hept-2-yl)phenoxy]methyl}quinoline (6c) and 2-{[4-(2-methyl-2H-tetrazol-5-yl)-3-(2-phenylbicyclo[2.2.1]hept-2-yl)phenoxy]methyl}quinoline (6d)

Freshly ground anhydrous potassium carbonate (14.0 mg, 0.10 mmol) was added to a stirred solution of 6b (31.0 mg, 0.07 mmol) in DMF (1.0 mL) at room temperature. After 1 h, methyl iodide (6.20 µL, 0.10 mmol) was added via syringe.

After 3 h, the reaction mixture was poured into water and extracted three times with EtOAc. The combined organic extracts were washed repeatedly with water, brine, dried (MgSO$_4$) and concentrated. Purification of the crude residue by flash chromatography on silica gel (gradient elution; 0-20% acetone/hexanes as eluent) afforded in order of elution:

the title compound 6d as an off-white foam. R$_f$: 0.50 (2:1 hexane:EtOAc). m/z (ES) 488 (MH)$^+$. $^1$H NMR (500 MHz, CDCl$_3$): δ 0.72-0.79 (m, 1H), 1.13-1.30 (m, 2H), 1.42-1.50 (m, 2H), 1.96 (br d, 1H), 2.17 (td, J=3.5, 16 Hz, 1H), 2.4 (br s, 1H), 2.44 (dd, J=2.5, 14 Hz, 1H), 2.87 (d, J=3.9 Hz, 1H), 4.11 (s, 3H), 5.49-5.56 (m, 2H), 6.71-6.79 (m, 2H), 6.88 (dd, J=2.7, 8.5 Hz, 1H), 6.94-7.04 (m, 3H), 7.15 (d, J=8.2 Hz, 1H), 7.58-7.61(m, 1H), 7.62 (d, J=2.5 Hz, 1H), 7.76-7.81 (m, 2H), 7.88 (d, J=8.0 Hz, 1H), 8.13 (d, J=8.5 Hz, 1H), 8.27 (d, J=8.5 Hz, 1H).

and the title compound 6c as an off-white foam. R$_f$: 0.45 (2:1 hexane:EtOAc). m/z (ES) 488 (MH)+$^1$H NMR (500 MHz, CDCl$_3$): δ 0.57-0.61 (m, 1H), 1.01-1.05 (m, 1H), 1.18-1.30 (m, 1H), 1.37-1.44 (m, 2H), 1.81 (br d, 1H), 2.29 (td, J=2.9, 14 Hz, 1H), 2.34-2.42 (m, 2H), 2.68 (s, 3H), 2.98 (br s, 1H), 5.50-5.56 (m, 2H), 6.56-6.80 (m, 2H), 6.85 (d, J=8.4 Hz, 1H), 6.92 (dd, J=2.5, 8.2 Hz, 1H), 7.02-7.12 (m, 3H), 7.61(m, 1H), 7.66 (d, J=2.3 Hz, 1H), 7.75-7.82 (m, 2H), 7.89 (d, J=8.0H, 1H), 8.13 (d, J=8.4 Hz, 1H), 8.29 (d, J=8.1 Hz, 1H).

6c was separated into its enantiomers by Chiralpak AD column using 30% IPA/heptane (flow rate=0.5 mL/min, λ=254 nM, retention times: 13.4, 14.1 min).

6d was separated into its enantiomers by Chiralpak AD column using 10% IPA/heptane (flow rate=0.5 mL/min, λ=254 nM, retention times: 28.9, 39.9 min).

Following procedures similar to that described above for Examples 6a-d, the following compounds can be prepared as either single enatiomers or racemic mixtures:

TABLE 6

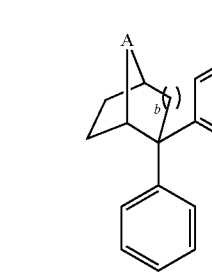

| Ex. #6 | A | b | R$^1$ | R$^2$ | Parent Ion m/z (MH)$^+$ |
|---|---|---|---|---|---|
| e* | CH$_2$ | 1 |  | 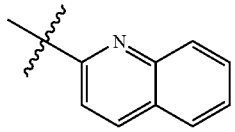 | 524 |
| f* | CH$_2$ | 1 | 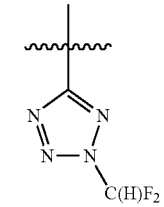 | 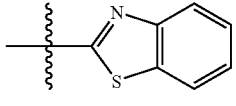 | 524 |
| g | CH$_2$ | 1 | 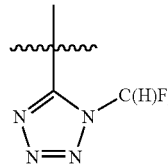 | | |

TABLE 6-continued
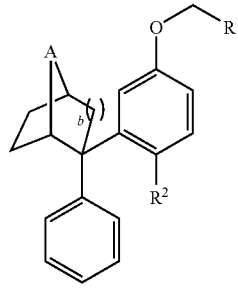
| Ex. #6 | A | b | R¹ | R² | Parent Ion m/z (MH)⁺ |
|---|---|---|---|---|---|
| h | CH₂ | 1 | 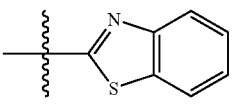 | 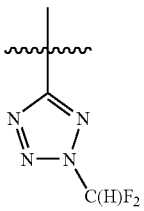 | |
| i* | CH₂ | 1 | 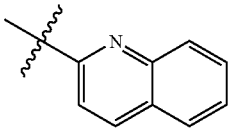 | 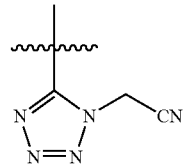 | 513 |
| j* | CH₂ | 1 | 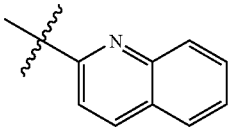 | 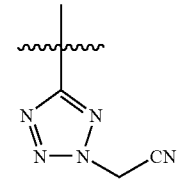 | 513 |
| k | CH₂ | 1 | 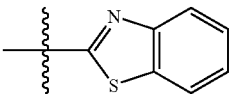 | 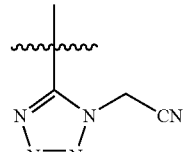 | |
| l | CH₂ | 1 | 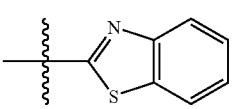 | 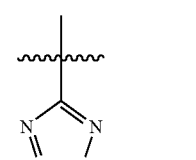 | |
| m* | CH₂ | 1 | 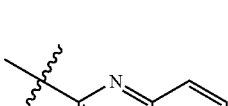 | 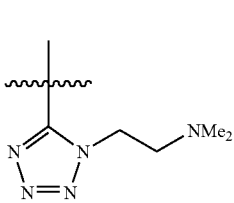 | 545 |

TABLE 6-continued
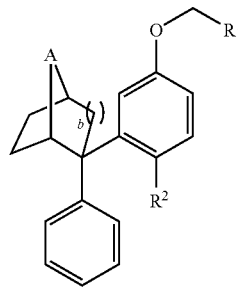
| Ex. #6 | A | b | R¹ | R² | Parent Ion m/z (MH)⁺ |
|---|---|---|---|---|---|
| n* | CH₂ | 1 | 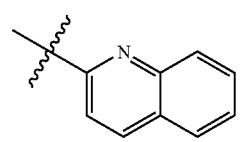 | 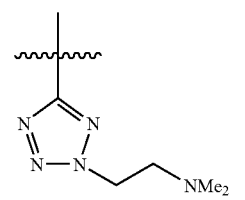 | 545 |
| o | CH₂ | 1 | 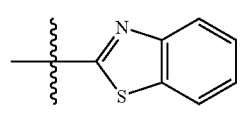 | 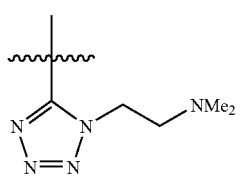 | |
| p | CH₂ | 1 | 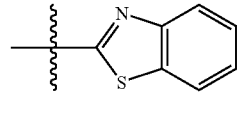 | 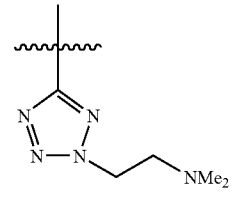 | |
| aa*** | CH₂CH₂ | 0 | 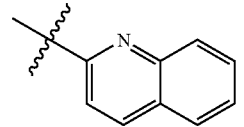 | 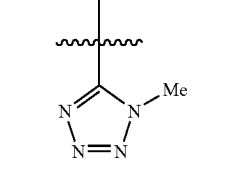 | |
| ab*** | CH₂CH₂ | 0 | 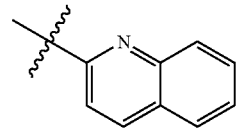 | 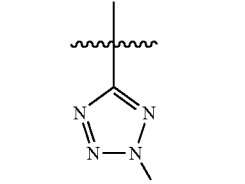 | |

TABLE 6-continued
| Ex. #6 | A | b | R¹ | R² | Parent Ion m/z (MH)+ |
|---|---|---|---|---|---|
| ac*** | CH₂CH₂ | 0 | (quinolin-2-yl) | (1-CHF₂-tetrazol-5-yl) | |
| ad*** | CH₂CH₂ | 0 | (quinolin-2-yl) | (2-CHF₂-tetrazol-5-yl) | |
*Prepared as racemic mixture;
***Compound is achiral
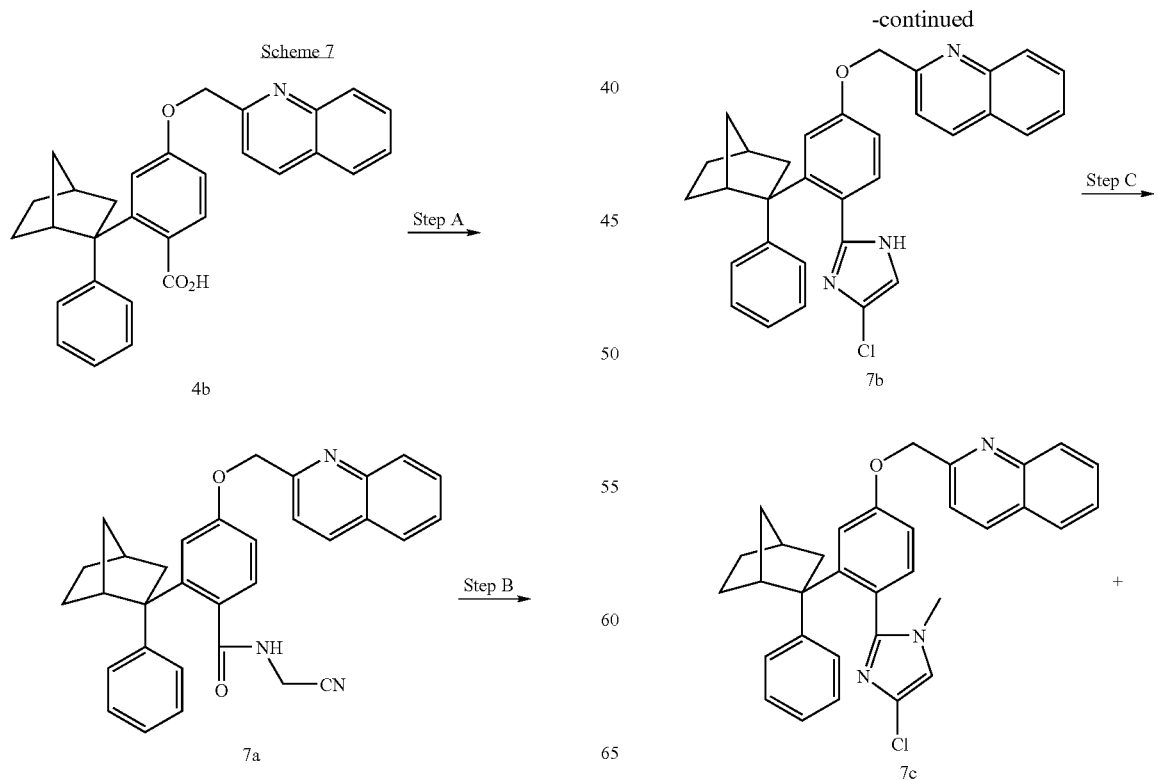

-continued

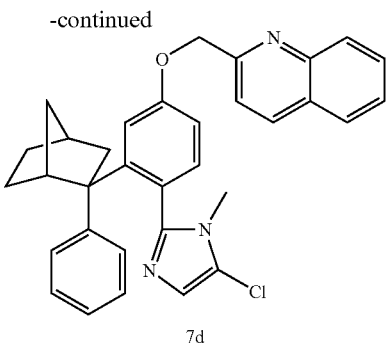

7d

EXAMPLES 7a, 7b, 7c AND 7d

Step A

Preparation of (−)-N-(cyanomethyl)-2-(2-phenlbicyclo[2.2.1]hept-2-yl)-4-(quinolin-2-ylmethoxy)benzamide (7a)

Aminoacetonitrile hydrochloride (17.0 mg, 0.18 mmol), triethylamine (42.0 mg, 0.42 mmol), HATU (70.0 mg, 0.18 mmol), and DMAP (5.10 mg, 0.04 mmol) were added successively to a stirred solution of 4b (75.0 mg, 0.17 mmol) in methylene chloride/DMF (9:1; 1.0 mL) at room temperature. After approximately 15 h, the reaction mixture was poured into water and extracted three times with EtOAc. The combined orgainic extracts were washed twice with 5% citric acid, three times with water, brine, dried (MgSO$_4$) and concentrated in vacuo. Purification of the crude residue by flash chromatography on silica gel (gradient elution; 0-5% methanol/methylene chloride as eluent) afforded the title compound 7a as a white foam. R$_f$: 0.20 (49:1 methylene chloride:methanol). m/z (ES) 488 (MH)+. $^1$H NMR (500 MHz, CDCl$_3$): δ 0.84-0.92 (m, 1H), 1.25-1.36 (m, 2H), 1.37-1.39 (m, 1H), 1.46-1.56 (m, 1H), 1.74 (br d, 1H), 2.05 (dt, J=3.5, 13.2 Hz, 1H), 2.38 (br s, 1H), 2.48 (dd, J=2.3, 13.9 Hz, 1H), 2.86 (d, J=2.5 Hz, 1H), 3.51 (dd, J=5.1, 17.4 Hz, 1H), 3.91 (dd, J=6.2, 17.4 Hz), 4.68 (t, J=5.5 Hz, 1H), 5.53 (m, 2H), 6.83 (dd, J=2.3, 8.3 Hz, 1H), 7.11-7.18 (m, 3H), 7.18-7.32 (m, 3H), 7.52 (d, J=2.3 Hz, 1H), 7.59 (t, J=7 Hz, 1H), 7.72 (d, J=8.5 Hz, 1H), 7.75-7.79 (m, 1H), 7.87 (d, J=8.2 Hz, 1H), 8.11 (d, J=8.4 Hz, 1H), 8.25 (d, J=8.4 Hz, 1H).

Step B

Preparation of (−)-2-{[4-(4-chloro-1H-imidazol-2-yl)-3-(2-phenylbicyclo[2.2.1]hept-2-yl)phenoxy]methyl}quinoline (7b)

Triphenylphosphine (197 mg, 0.75 mmol) was added to a stirred solution of 7a (150 mg, 0.31 mmol) in acetonitrile (1.0 mL) at room temperature. Upon dissolution, carbon tetrachloride (116 mg, 0.75 mmol) was added dropwise via syringe. The resulting mixture was heated to approximately 50° C. and stirred for 2 h during which time the color of the reaction mixture changed from colorless to light brown. After cooling to room temperature, the volatiles were removed in vacuo. The residue was taken up in methylene chloride (1 mL), then saturated aqueous sodium bicarbonate (1 mL) was added, and the resulting biphasic mixture was stirred vigorously for 15 min at room temperature. The organic phase was separated and the aqueous phase was extracted twice with EtOAc. The combined organic extracts were washed with water, brine, dried (MgSO$_4$) and concentrated in vacuo. Purification of the crude residue by flash chromatography on silica gel (gradient elution, 040% EtOAc/hexanes as eluent) furnished the title compound 7b as an off-white foam. R$_f$: 0.70 (1:2 hexane:EtOAc). m/z (ES) 506 (MH)+. $^1$H NMR (500 MHz, CDCl$_3$): δ 0.91-1.02 (m, 1H), 1.22-1.38 (m, 3H), 1.40-1.55 (m, 1H), 1.62-1.68 (br d, 1H), 1.88-2.04 (m, 2H), 2.28-2.36 (br s, 1H), 2.89 (br s, 1H), 5.61 (s, 2H), 6.54 (s, 1H), 6.80-6.96 (m, 2H), 6.96-7.16 (m, 2H), 7.16-7.36 (m, 4H), 7.56-7.60 (m, 1H), 7.60-7.68 (m, 1H), 7.78-7.86 (m, 2H), 7.90-7.96 (m, 1H), 8.18-8.32 (m, 1H), 8.32-8.38 (m, 1H).

Step C

Preparation of (7d): (−)-2-{[4-(4-chloro-1-methyl-1H-imidazol-2-yl)-3-(2-phenylbicyclo[2.2.1]hept-2-yl)phenoxy]methyl}quinoline (7c) and (−)-2-{[4-(5-chloro-1-methyl-1H-imidazol-2-yl)-3-(2-phenylbicyclo[2.2.1]hept-2-yl)phenoxy]methyl}quinoline Freshly ground anhydrous potassium carbonate (5.30 mg, 0.04 mmol) was added to a stirred solution of 7b (13.0 mg, 0.026 mmol) in DMF (1.0 mL) at room temperature. After 1 h, methyl iodide (2.40 μL, 0.04 mmol) was added via syringe and the resulting mixture stirred at room temperature for 3 h. The reaction mixture was poured into water and extracted three times with EtOAc. The combined organic extracts were washed three times with water, brine, dried (MgSO$_4$) and concentrated in vacuo. Purification of the crude residue by flash chromatography on silica gel (gradient elution, 0-20% EtOAc/hexanes as eluent) provided in order of elution:

the title compound 7c. R$_f$: 0.40 (2:1 hexane:EtOAc). m/z (ES) 520 (MH)+. $^1$H NMR (500 MHz, CDCl$_3$): δ 0.60-0.68 (m, 1H), 1.02-1.09 (m, 1H), 1.20-1.44 (m, 3H), 1.80-1.85 (br d, 1H), 2.17 (s, 3H), 2.28-2.46 (m, 3H), 3.0 (br s, 1H), 5.55 (m, 2H), 6.41 (s, 1H), 6.76-6.96 (m, 4H), 6.98-7.16 (m, 3H), 7.59-7.70 (m, 2H), 7.76-7.98 (m, 3H), 8.14-8.26 (m, 1H), 8.28-8.36 (m, 1H); and the title compound 7d. R$_f$: 0.35 (2:1 hexane:EtOAc). m/z (ES) 520 (MH)+. $^1$H NMR (500 MHz, CDCl$_3$): δ 0.58-0.66 (m, 1H), 0.98-1.06 (m, 1H), 1.20-1.44 (m, 3H), 1.80-1.85 (br d, 1H), 2.11 (s, 3H), 2.28-2.42 (m, 3H), 3.0 (br s, 1H), 5.51 (m, 2H), 6.74-6.84 (m, 2H), 6.84-6.96 (m, 2H), 7.00-7.10 (m, 3H), 7.07 (s, 1H), 7.56-7.62 (m, 2H), 7.76-7.82 (m, 2H), 7.90 (d, J=8.2 Hz, 1H), 8.13 (d, J=8.5 Hz, 1H), 8.29 (d, J=8.5 Hz, 1H).

Following procedures similar to that described above for Examples 7a-d, the following compounds can be prepared as either single enantiomers or racemic mixtures:

TABLE 7
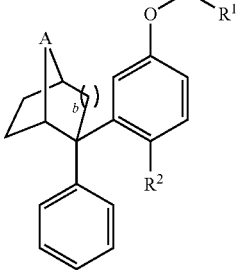
| Ex. #7 | A | b | R¹ | R² |
|---|---|---|---|---|
| e | CH₂ | 1 | 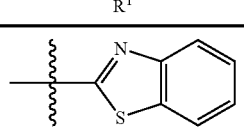 | 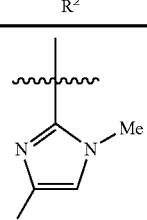 |
| f | CH₂ | 1 | 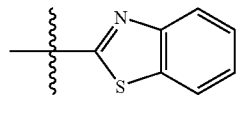 | 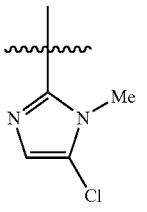 |
| g | CH₂ | 1 | 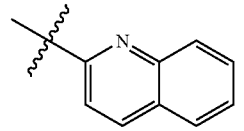 | 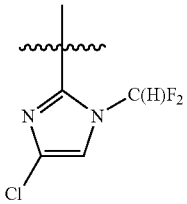 |
| h | CH₂ | 1 | 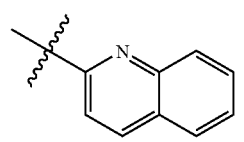 | 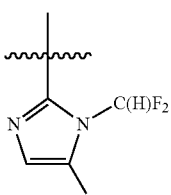 |
| aa*** | CH₂CH₂ | 0 | 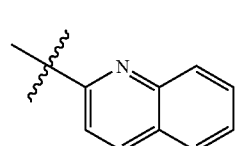 | 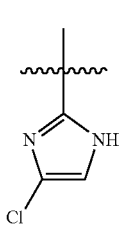 |
| ab*** | CH₂CH₂ | 0 | 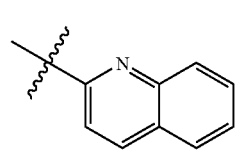 | 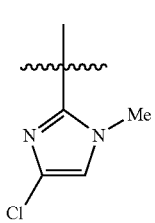 |

TABLE 7-continued
| Ex. #7 | A | b | R¹ | R² |
|---|---|---|---|---|
| ac*** | CH₂CH₂ | 0 | 2-quinolinyl | 5-chloro-1-methyl-imidazol-2-yl |
| ad*** | CH₂CH₂ | 0 | 2-quinolinyl | 4-chloro-1-(difluoromethyl)-imidazol-2-yl |
| ae*** | CH₂CH₂ | 0 | 2-quinolinyl | 5-chloro-1-(difluoromethyl)-imidazol-2-yl |
***Compound is achiral
Scheme 8
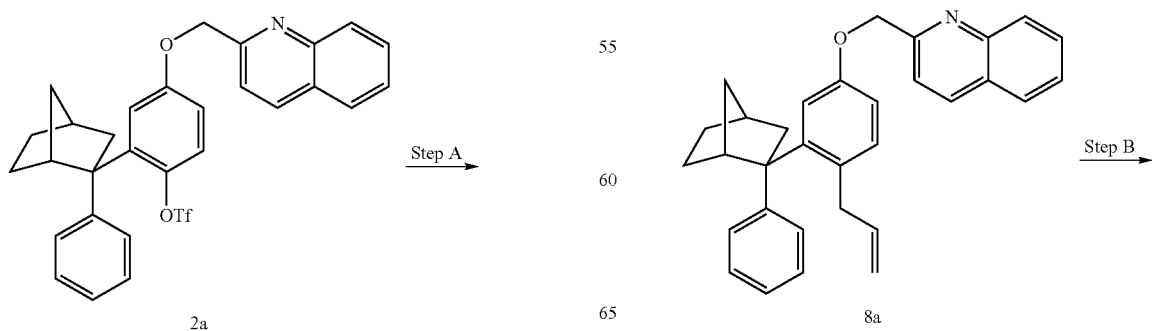

-continued

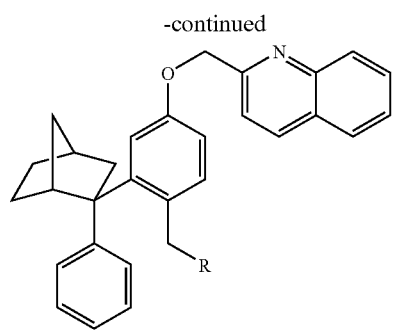

8b R = CO₂H
8c R = CHO

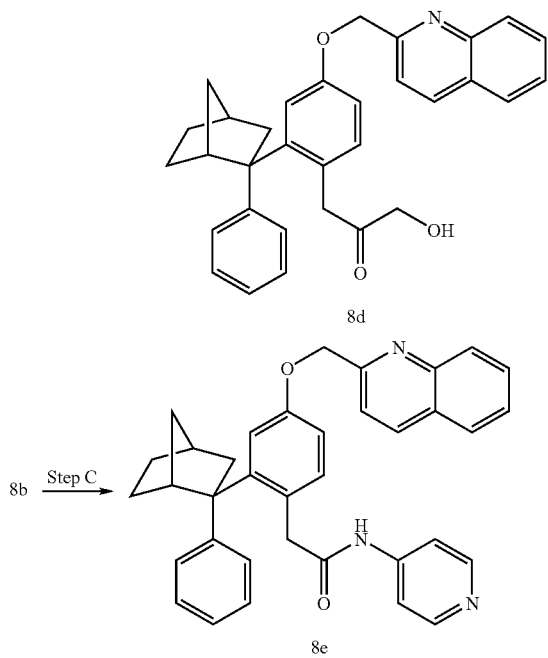

EXAMPLES 8a, 8b AND 8e

Step A

Preparation of (±)-2-{[4-Allyl-3-(2-phenylbicyclo[2.2.1]hept-2-yl)phenoxy]methyl}quinoline (8a)

Dppf (111 mg, 0.15 mmol), lithium chloride (60.0 mg, 1.42 mmol), and allyltributyltin (0.44 mL, 1.42 mmol) were added sequentially to a stirred solution of 2a (500 mg, 0.90 mmol) in NMP (1.5 mL) in a microwave tube at ambient temperature. The reaction mixture was irradiated in a microwave apparatus (300 W Maximum Power) for 60 minutes at 120° C. After removal of the volatiles in vacuo, the residue was treated with saturated aqueous potassium fluoride (33 mL) and the resulting mixture was stirred vigorously at 35° C. for 2 days. After extracting three times with EtOAc, the combined organic extracts were washed with water, brine, dried (MgSO₄), and concentrated in vacuo. Purification of the crude residue by flash chromatography on silica gel (gradient elution; 0-20% EtOAc/hexanes as eluent) furnished the title compound 8a. $R_f$: 0.60 (4:1 hexanes:EtOAc), m/z (ES) 446(MH)⁺.

Step B

Preparation of (±)-[2-(2-Phenylbicyclo[2.2.1]hept-2-yl)-4-(quinolin-2-ylmethoxy)phenyl]acetic acid (8b), (±)-[2-(2-phenylbicyclo[2.2.1]hept-2-yl)-4-(quinolin-2-ylmethoxy)phenyl]acetaldehyde (8c) and (±)-1-hydroxy-3-[2-(2-phenylbicyclo[2.2.1]hept-2-yl)-4-(quinolin-2-ylmethoxy)phenyl]acetone (8d)

Periodic acid (230 mg, 1.01 mmol) was added to a vigorously stirred solution of 8a (100 mg, 0.22 mmol) in acetonitrile/carbon tetrachloride/water (0.8 mL:0.8 mL:2 mL). After 10 min, ruthenium trichloride hydrate (5.60 mg, 0.03 mmol) was added. After 45 min, the reaction mixture was extracted three times with methylene chloride and the combined oraginc extracts were kept to one side. The aqueous phase was acidified with 10% aqueous citric acid and extracted three times with methylene chloride. As before, the combined organic extracts were kept to one side. Finally, the aqueous phase was neutralizd with solid sodium carbonate and extracted three times with methylene chloride. The combined organic phase from all of the extractions was dried (MgSO₄) and concentrated in vacuo. Purification of the crude residue by flash chromatography on silica gel (gradient elution; 0-15% methanol/methylene chloride as eluent) furnished in order of elution:

the α-hydroxy ketone intermediate 8d. $R_f$: 0.85 (1:9 methanol:methylene chloride). m/z (ES) 478(MH)⁺;

the aldehyde intermediate 8c. $R_f$: 0.80 (1:9 methanol:methylene chloride). m/z (S) 448 (MH)⁺; and the title compound 8b. $R_f$: 0.15 (1:9 methanol:methylene chloride). m/Z (ES) 464(MH)⁺.

A solution of sodium chlorite (0.50 g, 12.5 mmol) and sodium dihydrogenphosphate (0.40 g, 3.40 mmol) in water (2 mL) was added to a stirred solution of 8c (vide infra, 90.0 mg, 0.201 mmol) in 2-methyl-2-butene (2.5 mL of a 2M solution in THF) at room temperature. After 2 h, the reaction mixture was extracted three times with EtOAc. The combined organic extracts were washed with water, 10% w/v aqueous sodium thiosulfate, brine, dried (MgSO₄) and concentrated in vacuo. Purification of the crude residue by flash chromatography on silica gel (gradient elution; 0-10% methanol/methylene chloride as eluent) provided 8b, which was identical to the sample obtained above.

Step C

Preparation of (±)-2-[2-(2-phenylbicyclo[2.2.1]hept-2-yl)-4-(quinolin-2-ylmethoxy)phenyl]-N-pyridin-4-ylacetamide (8e)

4-Aminopyridine (29.0 mg, 0.31 mmol), DIPEA (54.0 μL, 0.31 mmol) and PyBOP (57.0 mg, 0.11 mmol) were added successively to a stirred solution of 8b (24.0 mg, 0.05 mmol) in methylene chloride (0.4 mL). After approximately 15 h, the reaction mixture was poured into water and extracted three times with EtOAc. The combined organic extracts were washed five times with 5% aqueous sodium bicarbonate, brine, dried (MgSO₄) and concentrated in vacuo. Purification of the crude residue by flash chromatography on silica gel (gradient elution; 0-5% methanol/methylene chloride as eluent) furnished the title compound 8e, $R_f$: 0.60 (9:1 methylene chloride:methanol), m/z (ES) 540(MH)⁺.

Following procedures similar to that described above for Examples 4a-e, 5a-e. 8a-b and 8e, the following compounds can be prepared (all compounds made in Table 8 were prepared as racemic mixtures):

TABLE 8
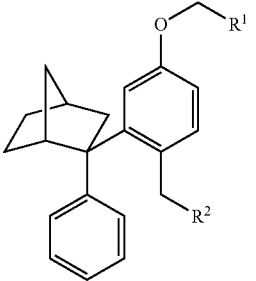
| Ex. #8 | R¹ | R² | Parent Ion m/z (MH)⁺ |
|---|---|---|---|
| f* | 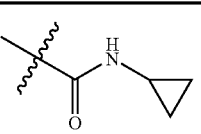 | 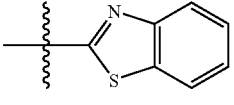 | 509 |
| g* | 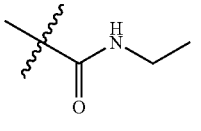 | 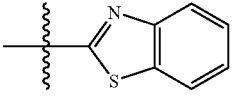 | 497 |
| h* | 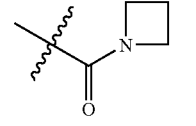 | 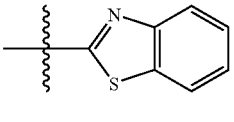 | 509 |
| i* | 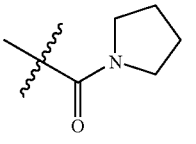 | 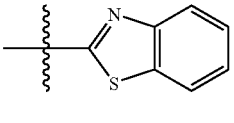 | 523 |
| j* | 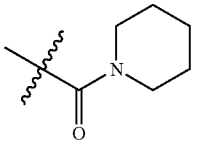 | 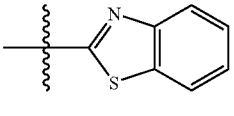 | 537 |
| k* | 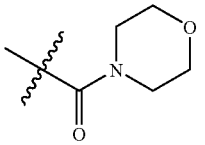 | 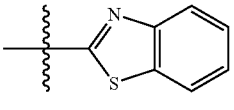 | 539 |
| l* | 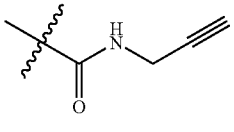 | 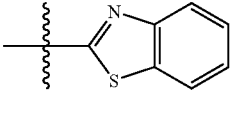 | 507 |
| m* | 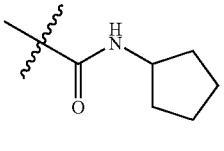 |  | 537 |

TABLE 8-continued
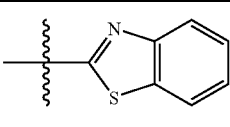
| Ex. #8 | R¹ | R² | Parent Ion m/z (MH)⁺ |
|---|---|---|---|
| n* | 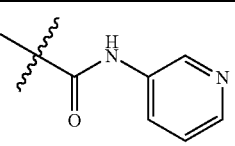 | 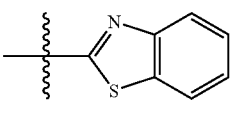 | 546 |
| o* | 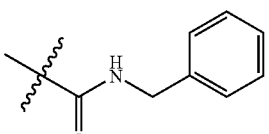 | 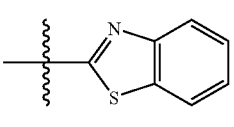 | 559 |
| p | 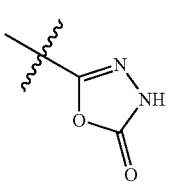 | 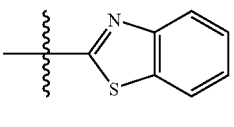 | |
| q | 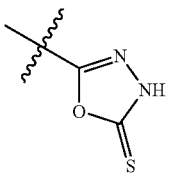 | 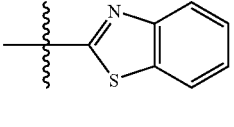 | |
| r | 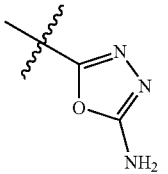 | 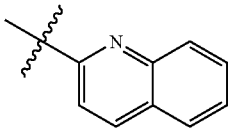 | |
| s* | 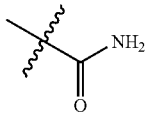 | 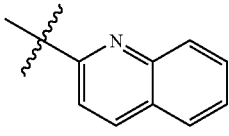 | 463 |
| t* | 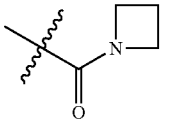 | | 503 |

TABLE 8-continued
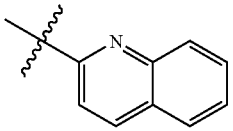
| Ex. #8 | R¹ | R² | Parent Ion m/z (MH)⁺ |
|---|---|---|---|
| u* | 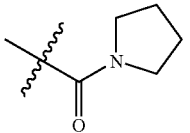 | 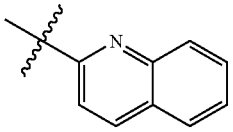 | 517 |
| v* | 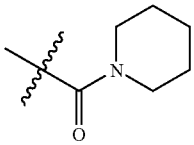 | 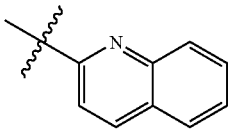 | 531 |
| w* | 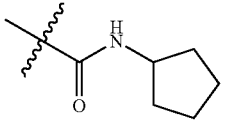 | 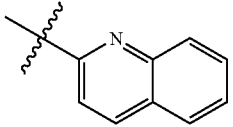 | 531 |
| x* | 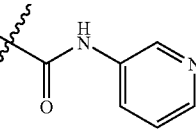 | 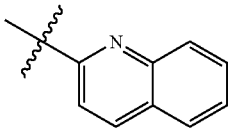 | 540 |
| y* | 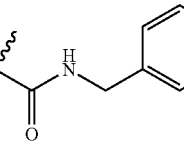 | 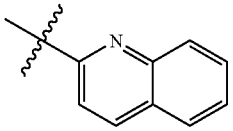 | 553 |
| z* | 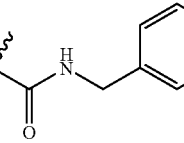 | 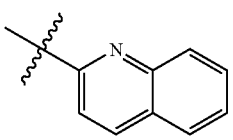 | 554 |
| aa* | 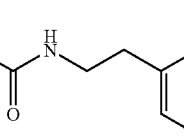 | 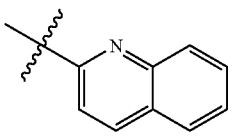 | 568 |
| ab* | 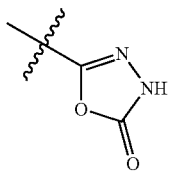 | | 504 |

TABLE 8-continued

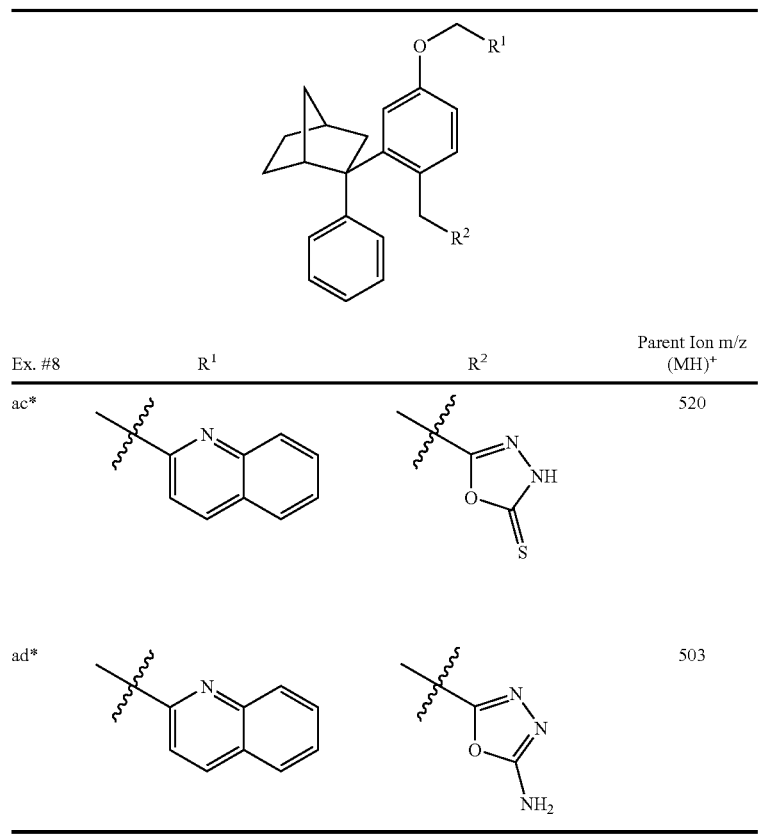

| Ex. #8 | R¹ | R² | Parent Ion m/z (MH)⁺ |
|---|---|---|---|
| ac* | quinolin-2-yl | 5-thioxo-4,5-dihydro-1,3,4-oxadiazol-2-yl | 520 |
| ad* | quinolin-2-yl | 5-amino-1,3,4-oxadiazol-2-yl | 503 |

*prepared as racemic mixture

Scheme 9

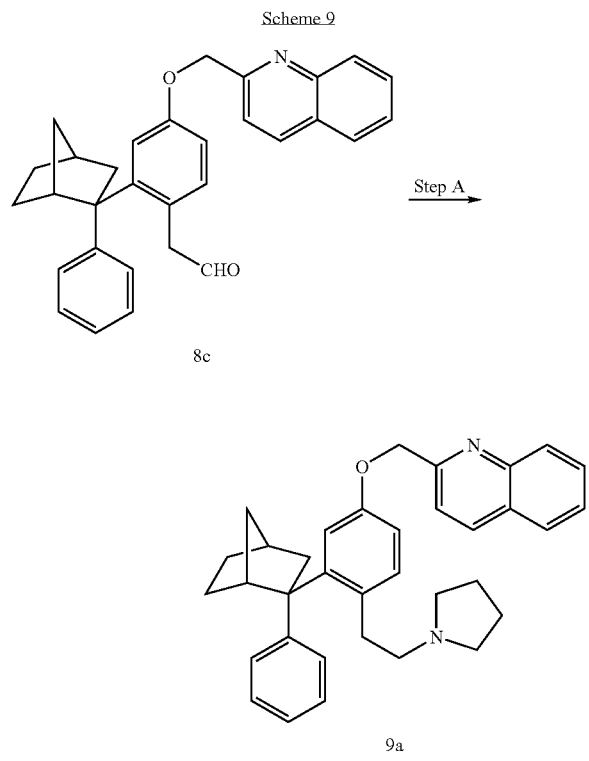

EXAMPLE 9a

Step A

Preparation of (±)-2-{[3-(2-phenylbicyclo[2.2.1]hept-2-yl)-4-(2-pyrrolidin-1-ylethyl)phenoxy]methyl}quinoline (9a)

Sodium triacetoxyborohydride (23.1 mg, 0.11 mmol) was added to a solution of 8c (35.0 mg, 0.08 mmol) and pyrrolidine (6.50 µL, 0.08 mmol) in 1,2-dichloroethane (0.27 mL) at room temperature. After 1 hour, the reaction mixture was poured into 5% aqueous sodium bicarbonate and extracted three times with EtOAc. The combined organic extracts were dried (Na₂SO₄) and concentrated in vacuo. Purification of the crude residue by flash chromatography on silica gel (5-20% methanol/methylene chloride as eluent) afforded the title compound 9a. $R_f$: 0.10 (1:1 hexane:EtOAc). m/z (ES) 503 (MH)⁺.

Following procedures similar to that described above for Examples 9a, the following compounds can be prepared (compounds made in Table 9 were prepared as racemic mixtures):

TABLE 9

| Ex. #9 | R¹ | R² | Parent Ion m/z (MH)⁺ |
|---|---|---|---|
| b | benzothiazol-2-yl | NHCH₃ | |
| c | benzothiazol-2-yl | N(CH₃)₂ | |
| d* | benzothiazol-2-yl | pyrrolidin-1-yl | 509 |
| e | benzothiazol-2-yl | piperidin-1-yl | |
| f | quinolin-2-yl | NHCH₃ | |
| g | quinolin-2-yl | N(CH₃)₂ | |
| h | quinolin-2-yl | piperidin-1-yl | |
| i* | quinolin-2-yl | NHCH₂Ph | 539 |

*prepared as racemic mixture

FLAP Binding Assay

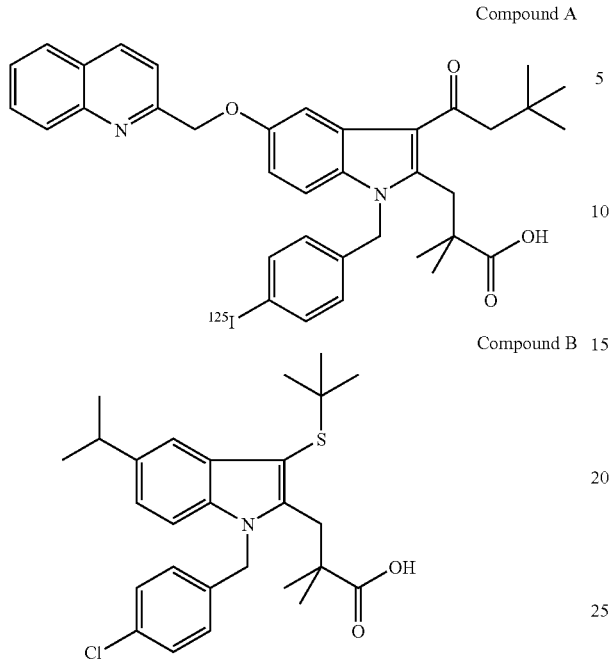

Compound A

Compound B

A 100,000×g pellet from human leukocyte 10,000×g supernatants (1) is the source of FLAP. The 100,000×g pellet membranes were resuspended in Tris-Tween assay buffer (100 mM Tris HCl pH 7.4, 140 mM NaCl, 2 mM EDTA, 0.5 mM dithiothreitol, 5% glycerol, 0.05% Tween 20) to yield a final protein concentration of 50 μg to 150 μg/ml. Aliquots (100 μl) of membrane suspension were added to 12 mm×75 mm polypropylene tubes containing 100 μl Tris-Tween assay buffer, 30,000 cpm of Compound A in 5 μMeOH:assay buffer (1:1), and 2 μl dimethyl sulfoxide or competitor (i.e., the compound to be tested) in dimethyl sulfoxide. Compound B (10 μM final concentration) was used to determine non-specific binding. After a 20 minute incubation at room temperature, tube contents were diluted to 4 ml with cold 0.1 M Tris HCl pH 7.4, 0.05% Tween 20 wash buffer and the membranes were collected by filtration of GFB filters presoaked in the wash buffer. Tubes and filters were rinsed with 2×4 ml aliquots of cold wash buffer. Filters were transferred to 12 mm×3.5 mm polystyrene tubes for determination of radioactivity by gamma-scintillation counting.

Specific binding is defined as total binding minus non-specific binding. Total binding was Compound A bound to membranes in the absence of competitor; non-specific binding was Compound A bound in the presence of 10 uM Compound B. Preparation of Compound A is described in reference 1, below. The $IC_{50}$ values obtained by computer analysis (see reference 2, below) of the experimental data, such that select compounds of the invention demonstrate an $IC_{50}$ in the range of about 1 nM to as high as about 10 μM.

REFERENCES

1. Charleson, S., Prasti, P., Leger, S., Gillard, J. W, Vickers, P. J., Mancini, J. A., Charleson, P., Guay, J., Ford-Hutchinson, A. W., and Evans, J. F. (1992) Characterization of a 5-lipoxygenase-activating protein binding assay: correlation of affinity for 5-lipoxygenase-activating protein with leukotriene synthesis inhibition. Mol Pharmacol 41:873-879.

2. Kinetic, EBDA, Ligand, Lowry: A collection of Radioligand Binding Analysis Programs by G. A. McPherson. Elsevier-BIOSOFT.

While the invention has been described with reference to certain particular embodiments thereof, numerous alternative embodiments will be apparent to those skilled in the art from the teachings described herein. All patents, patent applications and publications cited herein are incorporated by reference in their entirety.

What is claimed:

1. A compound represented by formula I-1:

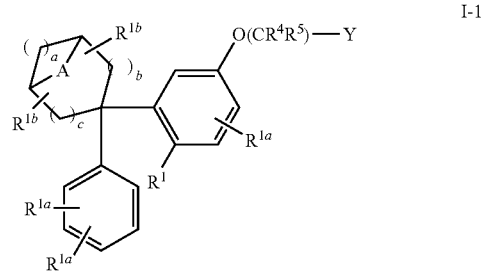

I-1 and the pharmaceutically acceptable salts and esters thereof wherein:

"a" is an integer selected from 1, 2 and 3; and b and c are each integers independently selected from 0, 1 and 2;

"A" represents a methylene or ethylene group;

each $R^{1a}$ is independently selected from the group consisting of: —H, —F, —Cl, —Br, —$C_{1-6}$alkyl, —CN, —OH, —$OC_{1-6}$ alkyl, -fluoro$C_{1-6}$alkyl, -fluoro$C_{1-6}$ alkoxy, —N($R^a$)$_2$, $C_{1-6}$ alkylN($R^a$)$_2$, —NHC(O)$C_{1-4}$alkyl, —C(O)NH$C_{1-4}$alkyl and —C(O)N($C_{1-4}$alkyl)$_2$;

each $R^{1b}$ is independently selected from the group consisting of: —H, —F, —$C_{1-6}$ alkyl, —OH, —$OC_{1-6}$ alkyl, -fluoro$Cl_{1-6}$alkyl, -fluoro$Cl_{1-6}$alkoxy, —N($R^a$)$_2$ and —$C_{1-6}$alkylN($R^a$), or one $R^{1b}$ group can represent oxo and the other is as previously defined;

$R^1$ represents —H or is selected from the group consisting of:

a) halo, —OH, —$CO_2R^a$, —C(O)$NR^aR^b$, —N($R^a$)$_2$ S(O)$_2NR^aR^b$, —NO$_2$, —$SO_2NR^bC(O)R^a$, —$NR^bSO_2R^a$, —$NR^bC(O)R^a$, —C(O)$SO_2NR^aR^b$, —$NR^bC(O)NR^aR^b$, —$NR^bCO_2R^a$, —OC(O)$NR^aR^b$—C(O)$NR^bNR^aR^b$, —CN, —S(O)$_pR^a$ and —$OSO_2R^a$, b) —$C_{1-10}$alkyl, —$C_{2-10}$alkenyl, —$C_{2-10}$alkynyl, —O$C_{1-10}$alkyl, —$OC_{3-10}$alkenyl and —$OC_{3-10}$alkynyl, said groups being optionally substituted with: —OH, —$CO_2R^a$, —C(O)$NR^aR^b$, —C(O)N($R^a$)$C_{1-6}$alkenyl, —C(O)N($R^a$)$C_{1-6}$alkynyl, —N($R^a$)$_2$, —S(O)$_2NR^aR^b$, —$SO_2NR^bC(O)R^a$, —$NR^b$ $SO_2R^a$, —$NR^bC(O)R^a$, —C(O)$SO_2NR^aR^b$, —$NR^bC(O)NR^aR^b$, —$NR^bCO_2R^a$, —OC(O)$NR^aR^b$, —C(O)$NR^bNR^aR^b$, —S(O)$_pR^a$, Aryl, and up to 5 fluoro groups;

c) Aryl optionally substituted with 1-2 members selected from the group consisting of: —F, —Cl, —Br, —$C_{1-6}$alkyl, —$C_{3-6}$cycloalkyl, —CN, —OH, —O$C_{1-6}$alkyl, -fluoro$C_{1-6}$ alkyl, -fluoro$C_{1-6}$alkoxy, —NH$_2$, —NH$C_{1-4}$alkyl, —N($C_{1-4}$alkyl)$_2$, —$C_{1-6}$alkylNH$_2$, —$C_{1-6}$alkyl-NH$C_{1-4}$alkyl, —$C_{1-6}$alkylN($C_{1-4}$alkyl)$_2$, —$C_{1-6}$alkyl-CN, —NHC(O)$C_{1-4}$alkyl, —C(O)NH$C_{1-4}$alkyl and —C(O)N($C_{1-4}$alkyl)$_2$;

each p independently represents an integer selected from 0, 1 and 2;

$R^4$ and $R^5$ are each independently selected from the group consisting of —H, —$C_{1-6}$ alkyl, —$OC_{1-6}$alkyl, —OH, -fluoro, -fluoro$C_{1-6}$alkyl, -fluoro$C_{1-6}$alkoxy, —N($R^a$)$_2$, and $CR^4R^5$ can represent a group selected from carbonyl, thiocarbonyl, C=$NR^a$ and a 3-7 membered cycloalkyl ring, Y is quinolinyl;

each $R^a$ is independently selected from the group consisting of —H and:
(a) —$C_{1-10}$alkyl, —$C_{3-6}$cycloalkyl, —$C_{3-10}$alkenyl, or —$C_{3-10}$alkynyl, optionally substituted with 1-3 fluoro groups or 1-2 members selected from the group consisting of: —OH, —O$C_{1-6}$alkyl, —CN, —NH$_2$, —NH $C_{1-4}$alkyl, and —N($C_{1-4}$alkyl)$_2$;
(b) Aryl or Ar—$C_{1-6}$alkyl—, the aryl portions being optionally substituted with 1-2 of —$C_{1-6}$ alkyl, —CN, —OH, —O$C_{1-6}$ alkyl, -fluoro$C_{1-6}$ alkyl, -fluoro$C_{1-6}$ alkoxy, —$C_{1-6}$alkylNH$_2$, —$C_{1-6}$alkylNH$C_{1-4}$alkyl, —$C_{1-6}$alkylN($C_{1-4}$alkyl)$_2$, —NH$_2$, —NH$C_{1-4}$alkyl, —N($C_{1-4}$alkyl)$_2$, —NHC(O)$C_{1-4}$alkyl, —C(O)NH $C_{1-4}$alkyl, —C(O)N($C_{1-4}$alkyl)$_2$, —CO$_2$H and —CO$_2C_{1-6}$alkyl groups, and 1-3 —F, —Cl or —Br groups; and the alkyl portion of Ar—$C_{1-6}$alkyl—being optionally substituted with —OH, —O$C_{1-6}$alkyl, —NH$_2$, —NH$C_{1-4}$alkyl, —N($C_{1-4}$alkyl)$_2$, and 1-3 fluoro groups;

each $R^b$ is independently selected from the group consisting of: —H, —NH$_2$, and —$C_{1-10}$alkyl optionally substituted with members selected from the group consisting of 1-3 fluoro groups and 1-2 of —OH, —O$C_{1-6}$alkyl, —NH$_2$, —NH$C_{1-4}$alkyl and —N($C_{1-4}$alkyl)$_2$;

and when present in the same moiety, (a) $R^a$ and $R^b$, (b) two $R^a$ groups or (c) two $R^b$ groups can be taken in combination with the atom or atoms to which they are attached and any intervening atoms and represent a 4-7 membered ring containing 0-3 heteroatoms selected from O, S(O)$_p$ and N, and the 4-7 membered ring may be optionally substituted with a member selected from the group consisting of —$C_{1-6}$alkyl, —$C_{2-6}$acyl and oxo.

2. The compound of claim 1 of structural formula Ia-1:

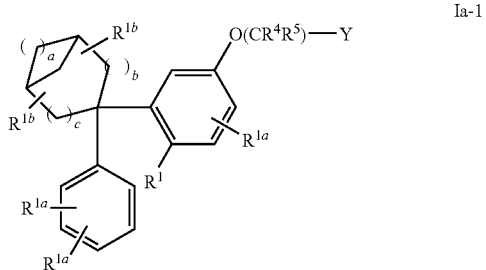

Ia-1 and the pharmaceutically acceptable salts and esters thereof, wherein "a" is an integer selected from 1, 2 and 3; and b and c are each integers independently selected from 0, 1 and 2; provided that the sum of "a"+b+c is from 1 to 5.

3. The compound of claim 1 of structural formula Ib-1:

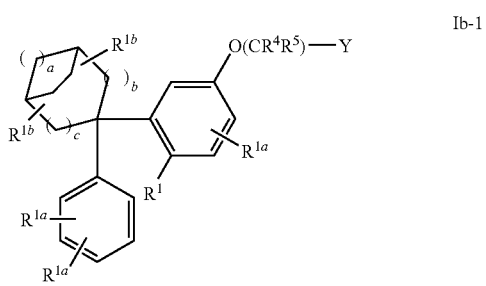

Ib-1 and the pharmaceutically acceptable salts and esters thereof wherein: "a" is an integer selected from 2 and 3; and b and c are integers independently selected from 0 and 1; provided that the sum of "a"+b+c is from 2 to 4.

4. The compound of claim 3 wherein "a" is 2, and b and c are integers selected from 0 and 1.

5. The compound of claim 1 wherein of the three $R^{1a}$ groups shown in the generic structural drawing of formula I-1, two $R^{1a}$ groups represent —H and one $R^{1a}$ group is selected from the group consisting of: —F, —Cl, —$C_{1-6}$ alkyl, —CN, —O$C_{1-6}$ alkyl, -fluoro$C_{1-6}$ alkyl, -fluoro $C_{1-6}$alkoxy, —N($R^a$)$_2$, —$C_{1-6}$alkylN($R^a$)$_2$, —NHC(O) $C_{1-4}$alkyl, —C(O)NH$C_{1-4}$alkyl and —C(O)N($C_{1-4}$alkyl)$_2$.

6. The compound of claim 1 wherein both $R^{1b}$ groups represent —H.

7. The compound of claim 1 wherein $R^{1b}$ represents a member selected from the group consisting of:
a)   —C(O)NR$^a$R$^b$, —N(R$^a$)$_2$, —S(O)$_2$NR$^a$R$^b$, —SO$_2$NR$^b$C(O)R$^a$, —NR$^b$SO$_2$R$^a$, —NR$^b$C(O)R$^a$, —CN, —S(O)$_p$R$^a$ and —OSO$_2$R$^a$; and
b) —$C_{1-10}$alkyl, —$C_{3-6}$alkenyl, —$C_{3-6}$alkynyl, —O$C_{1-10}$alkyl, —O$C_{3-6}$alkenyl and —O$C_{3-6}$alkynyl, said groups being optionally substituted with a member selected form the group consisting of: —CO$_2$R$^a$, —C(O)NR$^a$R$^b$, —C(O)N(R$^a$)C$_{1-6}$alkenyl, —C(O)N (R$^a$)C$_{1-6}$alkynyl, —N(R$^a$)$_2$, —S(O)$_2$NR$^a$R$^b$, —SO$_2$NR$^b$C(O)R$^a$, —NR$^b$SO$_2$R$^a$, NR$^b$C(O)R$^a$, —S(O)$_p$R$^a$, Aryl, and up to 5 fluoro groups.

8. The compound of claim 1 wherein —(CR$^4$R$^5$)—represents —CH$_2$—.

9. The compound of claim 1 of structural formula Ic-1:

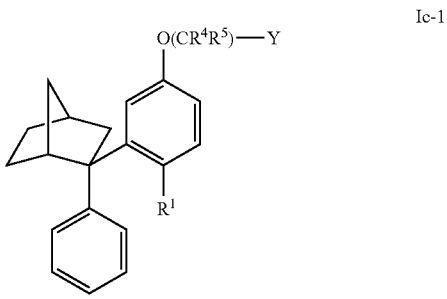

Ic-1 wherein $R^4$ and $R^5$ are both —H;
$R^1$ is selected from the group consisting of:
a) —OC(O)NR$^a$R$^b$, and —C(O)NR$^a$R$^b$; and
b) $C_{1-3}$alkyl substituted with a member selected from: —C(O)—NR$^a$R$^b$.

10. A pharmaceutical composition comprised of a therapeutically effective amount of a compound of claim 1 and a pharmaceutically acceptable carrier.

* * * * *

UNITED STATES PATENT AND TRADEMARK OFFICE
CERTIFICATE OF CORRECTION

PATENT NO.       : 7,629,467 B2                                   Page 1 of 1
APPLICATION NO.  : 10/565604
DATED            : December 8, 2009
INVENTOR(S)      : Chu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 446 days.

Signed and Sealed this

Second Day of November, 2010

David J. Kappos
*Director of the United States Patent and Trademark Office*